(12) United States Patent
Sharma et al.

(10) Patent No.: US 7,354,923 B2
(45) Date of Patent: Apr. 8, 2008

(54) PIPERAZINE MELANOCORTIN-SPECIFIC COMPOUNDS

(75) Inventors: Shubh D. Sharma, Cranbury, NJ (US); Yi-Qun Shi, East Brunswick, NJ (US); Zhijun Wu, Plainsboro, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 467 days.

(21) Appl. No.: 10/762,079

(22) Filed: Jan. 21, 2004

(65) Prior Publication Data

US 2004/0157264 A1 Aug. 12, 2004

Related U.S. Application Data

(63) Continuation-in-part of application No. PCT/US02/25574, filed on Aug. 12, 2002.

(60) Provisional application No. 60/474,497, filed on May 30, 2003, provisional application No. 60/441,139, filed on Jan. 17, 2003, provisional application No. 60/311,404, filed on Aug. 10, 2001.

(51) Int. Cl.
*A61K 31/497* (2006.01)
*C07D 403/04* (2006.01)

(52) U.S. Cl. .................. 514/252.13; 544/366

(58) Field of Classification Search ............. 514/235.8, 514/254.01, 254.05, 252.13; 544/366
See application file for complete search history.

(56) References Cited

U.S. PATENT DOCUMENTS

| | | | |
|---|---|---|---|
| 4,148,923 A | 4/1979 | Giudicelli et al. | |
| 4,239,763 A | 12/1980 | Milavec et al. | |
| 4,626,549 A | 12/1986 | Molloy et al. | |
| 4,680,289 A | 7/1987 | Applezweig | |
| 4,711,957 A | 12/1987 | Lai et al. | |
| 4,766,125 A | 8/1988 | Van Daele et al. | |
| 4,937,267 A | 6/1990 | Holloway et al. | |
| 4,943,578 A | 7/1990 | Naylor et al. | |
| 4,968,684 A | 11/1990 | Van Daele et al. | |
| 4,997,836 A | 3/1991 | Sugihara et al. | |
| 5,120,713 A | 6/1992 | Mugica | |
| 5,292,726 A | 3/1994 | Ashton et al. | |
| 5,344,830 A | 6/1994 | Mills et al. | |
| 5,348,955 A | 9/1994 | Greenlee et al. | |
| 5,464,788 A | 11/1995 | Bock et al. | |
| 5,550,131 A | 8/1996 | Sugihara et al. | |
| 5,574,031 A | 11/1996 | Abramo et al. | |
| 5,599,809 A | 2/1997 | Hickey et al. | |
| 5,672,602 A | 9/1997 | Burkholder et al. | |
| 5,736,539 A | 4/1998 | Graham et al. | |
| 5,753,445 A | 5/1998 | Fillit et al. | |
| 5,753,653 A | 5/1998 | Bender et al. | |
| 5,798,359 A | 8/1998 | Shue et al. | |
| 5,804,578 A | 9/1998 | Chakravarty et al. | |
| 5,856,326 A | 1/1999 | Anthony et al. | |
| 5,968,938 A | 10/1999 | Williams et al. | |
| 6,020,334 A | 2/2000 | Fukushi et al. | |
| 6,033,656 A | 3/2000 | Mikami et al. | |
| 6,127,424 A | 10/2000 | Martin et al. | |
| 6,162,805 A | 12/2000 | Hefti | |
| 6,191,117 B1 | 2/2001 | Kozachuk | |
| 6,207,665 B1 | 3/2001 | Bauman et al. | |
| 6,207,699 B1 | 3/2001 | Rothman | |
| 6,214,831 B1 | 4/2001 | Yokoo et al. | |

(Continued)

FOREIGN PATENT DOCUMENTS

| | | |
|---|---|---|
| WO | WO 98/10653 | 3/1998 |
| WO | WO 00/05373 | 2/2000 |
| WO | WO 01/21647 | 3/2000 |
| WO | WO 00/40247 | 7/2000 |

(Continued)

OTHER PUBLICATIONS

Adan, Roger A., et al., "Identification of Antagonist for Melanocortin MC3, MC4, and Mc5 Receptors", *European Journal of Pharmacology*, Section 269 (1994), (1994),331-337.
Door, Robert T., et al., "Evaluation of Melanotan-II, A Superpotent Cyclic Melanotropic Peptide in a Pilot Phase Clinical Study", *Life Science*, vol. 58, No. 20, (1996),1777-1784.
Grant, G A., "Synthetic Peptides: A Users Guide", *GA Grant, editor, W.H. Freeman & Co.*, New York 1992, (1992),11-24

(Continued)

*Primary Examiner*—James O. Wilson
*Assistant Examiner*—Ebenezer Sackey
(74) *Attorney, Agent, or Firm*—Morgan, Lewis & Bockius LLP

(57) ABSTRACT

Melanocortin receptor-specific piperazine or ketopiperazine compounds having the structure:

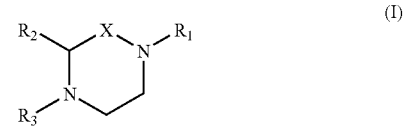

(I)

and stereoisomer and pharmaceutically acceptable salts thereof, where X is $CH_2$ or $C=O$, $R_1$, $R_2$, and $R_3$ are as described in the specification, preferably where $R_3$ is a D-amino acid with at least one substituted or unsubstituted phenyl or naphthyl aromatic ring, and where $R_3$ optionally further includes an amine capping group, a second amino acid residue or a second amino acid residue with an amine capping group, which compounds are agonists, antagonists or mixed agonists and antagonists at one or more melanocortin receptors, and having utility in the treatment of melanocortin receptor-related disorders and conditions. Methods of synthesis of compounds of structure (I), pharmaceutical compositions containing a compound of structure (I) and methods relating to the use thereof are also disclosed.

50 Claims, No Drawings

U.S. PATENT DOCUMENTS

| | | |
|---|---|---|
| 6,294,539 B1 | 9/2001 | Lou et al. |
| 6,140,354 A1 | 10/2001 | Dax et al. |
| 6,316,470 B1 | 11/2001 | Kover et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,959 B1 | 8/2002 | Cooper et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,699,873 B1 | 3/2004 | Maguire et al. |
| 6,734,175 B2 | 5/2004 | Hadcock et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0032238 A1 | 3/2002 | Priepke et al. |
| 2002/0037837 A1 | 3/2002 | Takada et al. |
| 2002/0052383 A1 | 5/2002 | Bakthavatchalam et al. |
| 2002/0065277 A1 | 5/2002 | Hadcock et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blimberg et al. |
| 2002/0128270 A1 | 9/2002 | Neya et al. |
| 2002/0137664 A1 | 9/2002 | Bakashi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055247 A1 | 3/2003 | Cosford et al. |
| 2003/0060473 A1 | 3/2003 | Neya et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Baumann et al. |
| 2003/0158209 A1 | 8/2003 | Dyke et al. |
| 2003/0166637 A1 | 9/2003 | Lehmann-Lintz et al. |
| 2003/0181441 A1 | 9/2003 | Mcclure et al. |
| 2003/0191136 A1 | 10/2003 | Bakthavatchalam et al. |
| 2003/0195212 A1 | 10/2003 | Lundstedt et al. |
| 2004/0024211 A1 | 2/2004 | Boyce et al. |
| 2004/0053933 A1 | 3/2004 | Pontillo et al. |

FOREIGN PATENT DOCUMENTS

| | | |
|---|---|---|
| WO | WO 00/74679 | 12/2000 |
| WO | WO 01/10842 | 2/2001 |
| WO | WO 01/12176 | 2/2001 |
| WO | WO 01/18210 | 3/2001 |
| WO | WO 01/21634 | 3/2001 |
| WO | WO 01/23392 | 4/2001 |
| WO | WO 01/30343 | 5/2001 |
| WO | WO 02/00259 | 6/2001 |
| WO | WO 01/55106 | 8/2001 |
| WO | WO 01/55107 | 8/2001 |
| WO | WO 01/55109 | 8/2001 |
| WO | WO 01/91752 | 12/2001 |
| WO | WO 02/00654 | 1/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 A1 | 2/2003 |
| WO | WO 03/066587 | 2/2003 |
| WO | WO 03/020724 | 3/2003 |
| WO | WO 03/031410 | 4/2003 |
| WO | WO 03/053927 | 7/2003 |
| WO | WO 03/061660 | 7/2003 |
| WO | WO 03/092690 | 11/2003 |
| WO | WO 03/093234 | 11/2003 |

OTHER PUBLICATIONS

Hadley, M E., et al., "Discovery and Development of Novel Melanogenic Drugs: Melanotan-I and -II", *Ronald. T. Borchardt, et al. editors; Integration of Pharmaceutical Discovery and Development: Case Histories, Plenum Press*, New York (1998), (1998),575-595.

Hruby, V J., et al., "Emerging Approaches in the Molecular Design of Receptor-Selective Peptide Ligands: Conformational, Topographical and Dynamic, (1990) Considerations", *Biochemical Journal*, (1990) 268, (1990),249-262.

Toniolo, C , "Conformationally Restricted Peptides Through Short-Range Cyclizations", *International Journal Peptide Protein Research*, 35, (1990), (1990),287-300.

PIPERAZINE MELANOCORTIN-SPECIFIC COMPOUNDS

CROSS-REFERENCE TO RELATED APPLICATIONS

This application is a continuation-in-part application of International Application No. PCT/US02/25574, International Publication No. WO 03/013571, entitled "Peptidomimetics of Biologically Active Metallopeptides", filed on Aug. 12, 2002, which claimed the benefit of the filing of of U.S. Provisional Patent Application Ser. No. 60/311,404, entitled "Receptor-Specific Peptides Derived from Biologically Active Metallopeptides", filed on Aug. 10, 2001, and the specification thereof of each is incorporated herein by reference.

This application claims the benefit of the filing of U.S. Provisional Patent Application Ser. No. 60/474,497, entitled "Substituted Piperazine Compounds Specific for Melanocortin Receptors", filed on May 30, 2003 and U.S. Provisional Patent Application Ser. No. 60/441,139, entitled "Ring Core Compounds Specific for Melanocortin Receptors", filed on Jan. 17, 2003, and the specification thereof of each is incorporated herein by reference.

BACKGROUND OF THE INVENTION

1. Field of the Invention (Technical Field)

The present invention relates to piperazine and ketopiperazine molecules with three biologically relevant pendant groups that bind to one or more melanocortin receptors and are agonists, antagonists or mixed agonist-antagonists.

2. Description of Related Art

Note that here and elsewhere the specification refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of tissues.

In general, compounds specific for MC1-R are believed to be useful for treatment of melanoma and melanin-associated disorders. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and other food intake and metabolism-related purposes and disorders. Compounds specific for MC3-R and MC4-R, among other melanocortin receptors, can be used as agents for treatment of sexual dysfunction, including male erectile dysfunction. Other melanocortin receptor-specific compounds, such as MC1-R agonists, can be used as tanning agents to increase melanin production. Compounds specific for MC1-R, MC3-R and MC5-R may be useful in regulation of inflammatory processes.

WO 02/085925, "Melanocortin Receptor Ligands", to The Proctor & Gamble Company, discloses ketopiperazine structures and methods of synthesis thereof, but does not disclose piperazine structures, methods to synthesize piperazine structures, or methods to synthesize optically pure structures, and further does not disclose structures with a pendant group consisting of a single D-Phe residue, or a derivative or homolog thereof, optionally with an amine capping group.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

BRIEF SUMMARY OF THE INVENTION

In one embodiment, the invention provides a compound having the structure:

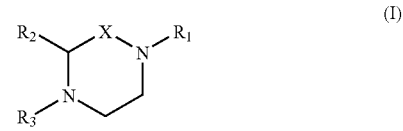

(I)

or a stereoisomer or pharmaceutically acceptable salt thereof, wherein $R_1$ is -$L_1$-J or, if X is $CH_2$, is H or -$L_1$-J;

$R_2$ is $(CH_2)_y$W or, if X is $CH_2$, is H or -$L_1$-J, on the proviso that not $R_1$ and $R_2$ are not both H;

$R_3$ is -$L_2$-Q;

$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings include 5 or 6 ring atoms;

W is a heteroatom unit with at least one cationic center, hydrogen bond donor or hydrogen bond acceptor wherein at least one atom is N;

$L_2$ is a linker selected from the group consisting of

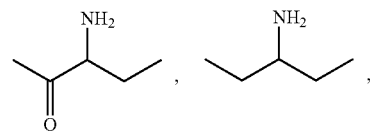

-continued

Q is an aromatic carbocyclic ring selected from the group consisting of phenyl, substituted phenyl, naphthyl and substituted naphthyl;

$R_4$ is H, —$R_5$ or —$R_5$—$R_6$;

$R_5$ is an amino acid residue or an amine capping group, provided that if $R_6$ is present, $R_5$ is an amino acid residue;

$R_6$ is H or an amine capping group;

X is $CH_2$ or C=O; and y is at each occurrence independently from 1 to 6.

In another embodiment, the invention provides a compound having the structure:

$$
\begin{array}{c}
\text{(II)}
\end{array}
$$

or a stereoisomer or pharmaceutically acceptable salt thereof, wherein $R_1$ is -$L_1$-J;

$R_2$ is $(CH_2)_y$—W;

$R_3$ is -$L_2$-Q;

$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings include 5 or 6 ring atoms;

W is a heteroatom unit with at least one cationic center, hydrogen bond donor or hydrogen bond acceptor wherein at least one atom is N;

$L_2$ is a linker selected from the group consisting of

Q is an aromatic carbocyclic ring selected from the group consisting of phenyl, substituted phenyl, naphthyl and substituted naphthyl;

$R_4$ is H, —$R_5$ or —$R_5$—$R_6$;

$R_5$ is an amino acid residue or an amine capping group, provided that if $R_6$ is present, $R_5$ is an amino acid residue;

$R_6$ is H or an amine capping group; and y is at each occurrence independently from 1 to 6;

wherein the carbon atom marked with an asterisk can have any stereochemical configuration.

In another embodiment, the invention provides a compound having the structure:

$$
\begin{array}{c}
\text{(III)}
\end{array}
$$

or a stereoisomer or pharmaceutically acceptable salt thereof, wherein $R_1$ is -$L_1$-J;

$R_2$ is $(CH_2)_y$—W;

$R_6$ is H or an amine capping group;

$R_{7a}$ and $R_{7b}$ are optional ring substituents, and when one or both are present, are the same or different and independently hydroxyl, halogen, alkyl, or aryl groups attached directly or through an ether linkage;

$L_1$ is a linker selected from the group consisting of —$(CH_2)_y$—, —O—$(CH_2)_y$—, —O—, —NH—

—(CH$_2$)$_y$—, —(C=O)(CH$_2$)$_y$—, —(C=O)—O—(CH$_2$)$_y$—, and —CH$_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings include 5 or 6 ring atoms;

W is a heteroatom unit with at least one cationic center, hydrogen bond donor or hydrogen bond acceptor wherein at least one atom is N; and y is at each occurrence independently from 1 to 6;

wherein the carbon atoms marked with an asterisk can have any stereochemical configuration.

In yet another embodiment, the invention provides a compound having the structure:

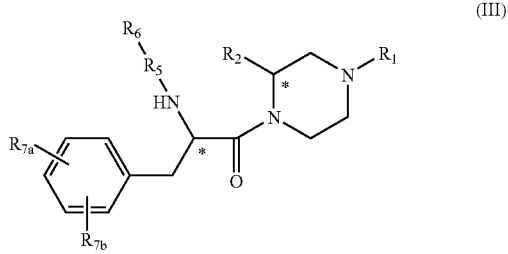

(III)

or a stereoisomer or pharmaceutically acceptable salt thereof, wherein

R$_1$ is -L$_1$-J;

R$_2$ is (CH$_2$)$_y$—W;

R$_5$ is an amino acid residue;

R$_6$ is H or an amine capping group;

R$_{7a}$ and R$_{7b}$ are optional ring substituents, and when one or both are present, are the same or different and independently hydroxyl, halogen, alkyl, or aryl groups attached directly or through an ether linkage;

L$_1$ is a linker selected from the group consisting of —(CH$_2$)$_y$—, —O—(CH$_2$)$_y$—, —O—, —NH—(CH$_2$)$_y$—, —(C=O)(CH$_2$)$_y$—, —(C=O)—O—(CH$_2$)$_y$—, and —CH$_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings include 5 or 6 ring atoms;

W is a heteroatom unit with at least one cationic center, hydrogen bond donor or hydrogen bond acceptor wherein at least one atom is N; and y is at each occurrence independently from 1 to 6;

wherein the carbon atoms marked with an asterisk can have any stereochemical configuration.

In any of the foregoing compounds, J can be a substituted or unsubstituted ring structure selected from the group consisting of

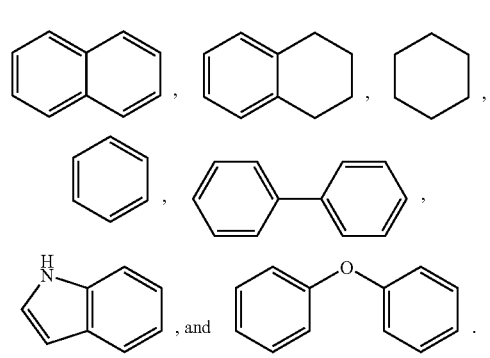

Thus at least one ring comprising J can be functionalized with one or more halogen, alkyl or aryl groups.

In any of the foregoing compounds, R$_1$ can be selected from the group consisting of

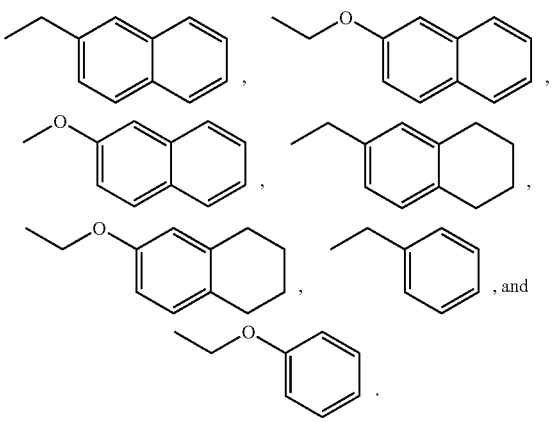

Alternative, R$_1$ can be selected from the group consisting of

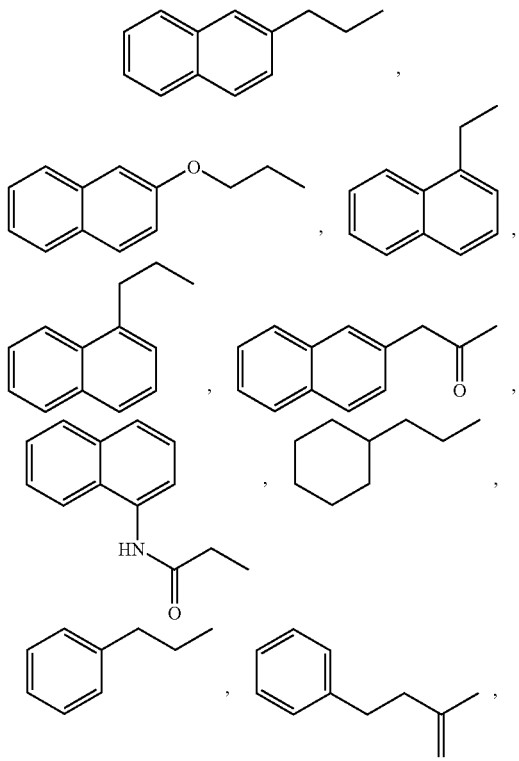

-continued

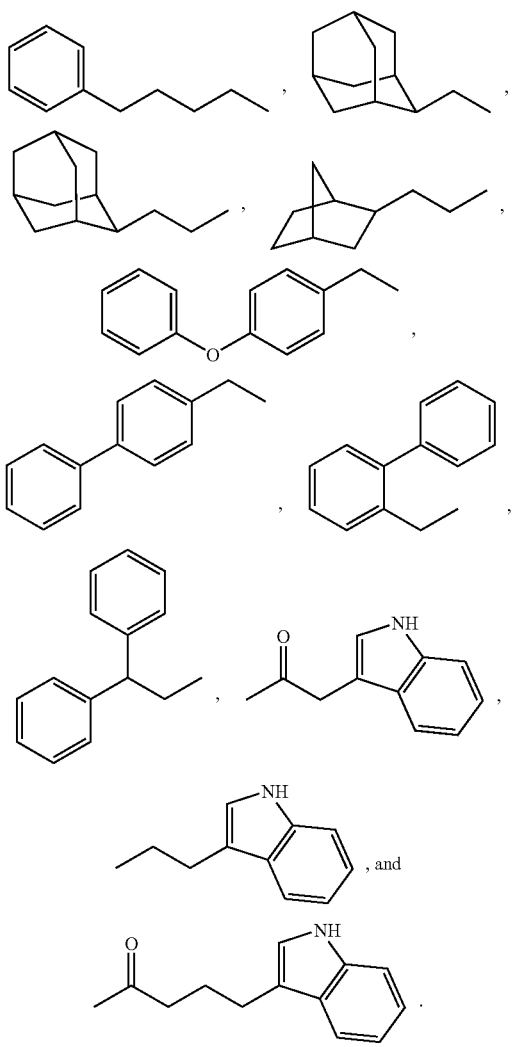

In a referred embodiment, W includes a cationic center and is selected from the group consisting of NH$_2$ and NH(C=NH)NH$_2$.

In an alternative embodiment, W is selected from the group consisting of —NHCOCH$_3$, —CONHCH$_3$, —NH(C=NH)NHMe, —NH(C=NH)NHEt, —NH(C=NH)NHPr, —NH(C=NH)NHPr—I, —NH(C=NH)NH$_2$, —NH(C=O)OCH$_3$, —NH(C=O)CH$_3$, NH(C=O)NH$_2$, —NH(C=O)NHCH$_3$,

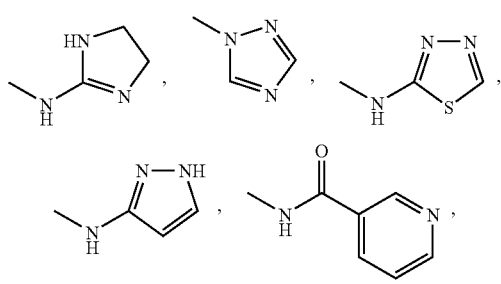

-continued

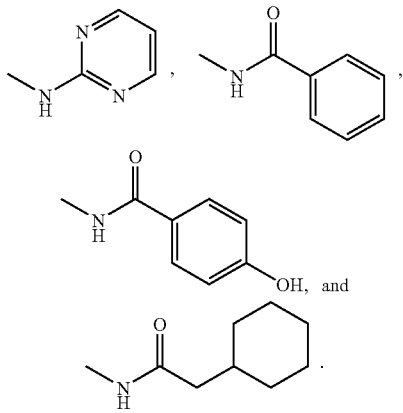

In any of the foregoing compounds, R$_2$ can be selected from the group consisting of

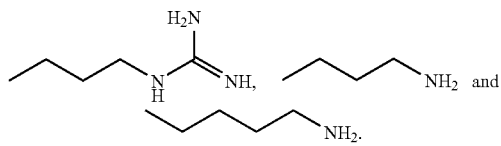

Where Q is provided in the foregoing compounds, Q can be

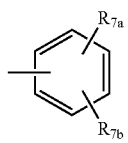

wherein R$_{7a}$ and R$_{7b}$ are optional ring substituents, and when one or both are present, are the same or different and independently hydroxyl, halogen, alkyl, or aryl groups attached directly or through an ether linkage. If R$_{7a}$ oe R$_{7b}$ are an alkyl group, they can be —CH$_3$ or —OCH$_3$.

In any of the foregoing compounds, R$_5$ or R$_6$ can be an amine capping group selected from the group consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc and 8-Aoc.

In any of the foregoing compounds, R$_3$ is preferably a D-amino acid with an aromatic carbocyclic ring selected from the group consisting of phenyl, substituted phenyl, naphthyl and substituted naphthyl, or further includes an amine capping group, or further is a member of a dipeptide, optionally further including an amine capping group. The D-amino acid can be selected from the group consisting of Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-CF$_3$), and Phe(3,4-di-OMe). Alternatively the D-amino acid can be selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl- Phenyl), Ser(p-Cl-Phenyl), Lys(Z), Lys(Z-2'Br), Lys(Bz), Thr(Bzl), Tic, Tiq, Cys(Bzl), Tyr(2,6-DiCl-Bzl) and Tyr (Bzl).

The second amino acid residue in the dipeptide, where provided, can be an L-amino acid, preferably selected from the group consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBZA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer (Bzl), Ser(O-2-Naphthyl), Ser(O-Phenyl), Ser(O-4-Cl-Phenyl), Ser(O-2-Cl-Phenyl), Thr(Bzl), Tic, Beta-homoThr (Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

In another embodiment the present invention provides a compound that is an agonist of a melanocortin receptor, including MC1-R, MC3-R, MC4-R, or MC5-R. The compound can also be an antagonist of a melanocortin receptor, including MC1-R, MC3-R, MC4-R, or MC5-R.

The invention further includes a method for altering a disorder or condition associated with the activity of a melanocortin receptor, comprising administering to a patient a therapeutically effective amount a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

A primary object of the present invention is provide piperazine and ketopiperazine compounds, with at least three biologically-relevant pendant groups, that are specific for one or more melanocortin receptors.

Another object of the present invention is to provide piperazine and ketopiperazine compounds where one pendant group consists of a single phenylalanine amino acid residue, or a derivative or homolog thereof, an optionally an amine capping group.

Another object of the present invention is to provide a method for synthesis of piperazine compounds without an oxo pendant group, and including three biologically-relevant pendant groups.

Another object of the present invention is to provide piperazine and ketopiperazine compounds that are useful for the treatment of eating disorders such as obesity and associated impairment of energy homeostasis.

Another object of the present invention is to provide a pharmaceutical compound useful for the treatment of disorders or conditions such as anorexia and cachexia.

Yet another object of the present invention is to provide melanocortin receptor specific compounds that are useful the treatment of sexual dysfunction including erectile dysfunction and female sexual dysfunction.

A further object of the present invention is to provide compounds that are specific for at least one of melanocortin receptors MC1-R, MC3-R, MC4-R, or MC5-R and which are agonists or antagonists.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the compounds and combinations particularly pointed out in the appended claims.

DETAILED DESCRIPTION OF THE INVENTION

Definitions. Certain terms used in this invention, and as used in the specification and claims, are defined as follows:

The terms "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, and any "derivative" of an amino acid side chain moiety, as the term "derivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The following abbreviations for amino acids or amino acid side chain moieties have the meanings given, it being understood that any amino acid listed may be in the L- or D-configuration:

Abu—gamma-amino butyric acid
2-Abz—2-amino benzoic acid
3-Abz—3-amino benzoic acid
4-Abz—4-amino benzoic acid
Achc—1-amino-cyclohexane-1-carboxylic acid
Acpc—1-amino-cyclopropane-1-carboxylic acid
12-Ado—12-amino dodecanoic acid
Aib—alpha-aminoisobutyric acid
Aic—2-aminoindane-2-carboxylic acid
6-Ahx—6-amino hexanoic acid
Amb—4-(aminomethyl)-benzoic acid Amc—4-(aminomethyl)-cyclohexane carboxylic acid
7'-amino-heptanoyl—NH$_2$-(CH$_2$)$_6$CO—
8-Aoc—8-amino octanoic acid
Arg(Tos)—N$^G$-para-tosyl-arginine
Asp(anilino)—beta-anilino-aspartic acid
Asp(3-Cl-anilino)—beta-(3-chloro-anilino)-aspartic acid
Asp(3,5-diCl-anilino)—beta-(3,5-dichloro anilino)-aspartic acid
Atc—2-aminotetralin-2-carboxylic acid
11-Aun—11-amino undecanoic acid
AVA—5-amino valeric acid
Beta-hHyp(Bzl)—Beta-(O-benzyl)-homohydroxyproline
Beta-hSer(Bzl)—Beta-(O-benzyl)-homoserine
Bip—biphenylalanine
Bzl—benzyl
Bz—benzoyl
Cha—cyclohexylalanine
Chg—cyclohexylglycine
Cmpi—4-caboxymethyl-piperazine
Dip—3,3-diphenylalanine
Disc—1,3-dihydro-2H-isoindolecarboxylic acid
Dpr(beta-Ala)—N$^{beta}$-(3-aminopropionyl)-alpha,beta-diaminopropionic acid
Et—ethyl
GAA—epsilon-guanidino acetic acid
GBzA—4-guanidino benzoic acid
B-Gpa—3-guanidino propionic acid
GVA(Cl)—beta-chloro-epsilon-guanidino valeric acid
Heptanoyl—CH$_3$—(CH$_2$)$_5$CO—
hPhe—homophenylalanine
hSer—homoserine
Hyp—hydroxy proline
hHyp—homo hydroxy proline
Hyp(Bzl)—O-benzyl-hydroxyproline
Hyp(2-naphthly)—O-2' naphthyl-hydroxyproline
Hyp(Phenyl)—phenyl-hydroxyproline
Idc—indoline-2-carboxylic acid
Igi—indanylglycine
Inp—isonipecotic acid
Lys(Z)—N-epsilon-benzyloxycarbonyl-lysine
Me——methyl
Nal 1—3-(1-naphthyl)alanine
Nal 2—3-(2-naphthyl)alanine
(N-Bzl)Nal 2—N-benzyl-3-(2-naphthyl) alanine
2-Naphthylacetyl—2-naphthyl-CH$_2$CO—
(Nlys)Gly—N-(4-aminobutyl)-glycine
(N-PhEt)Nal 2—N(2-phenylethyl)-3-(2-naphthyl) alanine
OcHx—cyclohexyl ester
Phg—phenylglycine
pF-Phe—para-fluoro-phenylalanine
Phe(4-Br)—4-bromo-phenylalanine
Phe(4-CF$_3$)—4-trifluoromethyl-phenylalanine
Phe(4-Cl)—4-chloro-phenylalanine
Phe(3-Cl)—3-chloro-phenylalanine
Phe(2-Cl)—2-chloro-phenylalanine
Phe(2,4-diCl)—2,4,-dichloro-phenylalanine
Phe(2,4-diF)—2,4-difluoro-phenylalanine
Phe(3,4-diCl)—3,4,-dichloro-phenylalanine
Phe(5-Cl)—5-chloro-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylalanine
Phe(4-OMe)—4-methoxy-phenylalanine
Phe(4-NC)—4-cyano-phenylalanine
Phe(4-NO$_2$)—4-nitro-phenylalanine
Pip—pipecolic acid
Pr—propyl
Pr—I—isopropyl
3-Pya—3-pyridylalanine
Pyr—pyroglutamic acid
Qal(2')—beta-(2-quinolyl)-alanine
Sal—3-styrylalanine
Sar—sarcosine
Ser(Bzl)—O-benzyl-serine
Ser(2-Naphthyl)—O-2-Naphthyl-serine
Ser(Phenyl)—O-2-Phenyl-serine
Ser(4-Cl-Phenyl)—O-4-Cl-Phenyl-serine
Ser(2-Cl-Phenyl)—O-2-Cl-Phenyl-serine
Ser(p-Cl-Bzl)—O-4-Cl-Benzyl-serine
Thr(Bzl)—O-Benzyl-threonine
Tic—1,2,3,4-tetrahydroisoquinoline-3-carboxylic acid
Tiq—1,2,3,4-tetrahydroisoquinoline-1-carboxylic acid
Tle—tert-butylalanine
Tpi—1,2,3,4-tetrahydronorharman-3-carboxylic acid
Tyr(Bzl)—O-benzyl-tyrosine
Tyr(2,6-DiCl-Bzl)—O-(2,6 dichloro)benzyl-tyrosine
Z—benzyloxycarbonyl Conventional amino acid residues have their conventional meaning as given in Chapter 2400 of the *Manual of Patent Examining Procedure,* 7$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

In the specification and the claims, the term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthyl, 1-naphthyl, and 2-naphthyl, derivatives thereof, and the like.

The term "aralkyl" includes a radical—$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO—$.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl including groups such as hexyl, hexanoyl, heptanoyl, acetyl, cinnamoyl, phenylacetyl, cyclohexylacetyl, naphthylacetyl, benzyl, benzoyl, cinnamoyl, 12-Ado, 7'-amino heptanoyl, 6-Ahx, Amc, and 8-Aoc.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

AcOH acetic acid
Boc tertiary butyloxycarbonyl
Cbz benzyloxycarbonyl
DCM dichloromethane
DEAD diethyl azodicarboxylate
DIC 1,3-diisopropylcarbodiimide
DMF N,N-dimethylformamide
DMSO dimethyl sulfoxide
EtOAc ethylacetates
Fmoc 9-fluorenylmethoxycarbonyl
HEPES 4-(2-hydroxyethyl )1-piperazineethanesulfonic acid
HOAt 1-hydroxy-7-azabenzotriazole
IBCF isobutyl chloroformate
LAH lithium aluminum hydride
NMM N-methyl-morpholine
NMP 1-methyl-2-pyrrolidinone
TBTU 2-(1 H-Benzotriazole-1-yl)-1,1,3,3-tetramethyluronium tetrafluoroborate
TEA triethylamine
TFA trifluoroacetic acid
THF tetrahydrofuran
TPP triphenylphosphine "Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, that can interact with a melanocortin receptor and initiate a pharmacological response characteristic of the melanocortin receptor. By a melanocortin receptor "antagonist" is meant a drug or a compound, including a compound of this invention, that opposes the melanocortin receptor-associated responses normally induced by a melanocortin receptor agonist agent.

By "binding affinity" is meant the ability of a compound or drug to bind to its biological target.

In a preferred embodiment, the invention provides a compound of the general structure:

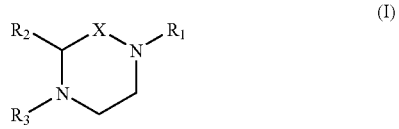

or a stereoisomer or pharmaceutically acceptable salt thereof, where $X$ is $CH_2$, O, C=O, C=S, S, S=O, or $SO_2$;

$R_1$ is an amino acid side chain moiety including at least one aryl, aralkyl or heteroaryl ring, and preferably comprising a fused bicyclic ring;

$R_2$ is a hydrogen bonding or cationic amino acid side chain moiety; and $R_3$ is an amino acid or dipeptide, optionally further including an amine capping group, wherein at least one amino acid residue includes a substituted or unsubstituted aryl or aralkyl, preferably wherein the at least one amino acid residue including a substituted or unsubstituted aryl or aralkyl is a D-amino acid residue.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic compound of this invention can accordingly be used as a therapeutic chemoprevention agent for combating harmful sun or UV exposure that induces neoplastic activity in skin melanocytes.

In another embodiment compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with a maturity-onset obesity syndrome associated with hyperphagia, hyperinsulinemia and hyperglycemia.

In yet another embodiment, compounds of this invention can be used as therapeutic agents for treatment of sexual dysfunction, including treatment of both male erectile dysfunction and female sexual dysfunction. In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

In general, the actual quantity of compound of this invention administered to a patient will vary between fairly wide ranges depending upon the mode of administration, the formulation used, and the response desired. This may readily be determined by one of ordinary skill in the art through means such as pharmacokinetic studies, plasma half-life studies, dose escalation studies, and the like.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce the desired therapeutic effect.

In general, the compounds of this invention are highly active, with dose responses as low as 0.01 μg/kg, generally with optimal or peak dose responses between about 0.01 μg/kg and 25 μg/kg, depending on the specific compound and the route of administration. For example, the compound can be administered at 0.01, 0.05, 0.1, 0.5, 1, 5, 10, 50, 100, or 500 μg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction. In an especially preferred embodiment of combination therapy the sexual dysfunction is erectile dysfunction. In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a compound of this invention and 2) a compound that is a melanocortin receptor agonist. The present invention further provides pharmaceutical compositions that comprise 1) a compound of this invention; 2) a compound that is a melanocortin receptor agonist; and 3) a third compound useful for the treatment of sexual dysfunction. The present invention further provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777-1784 (1996); and R. A. H. Adan, Identification of Antagonists for Melanocortin MC3, MC4, and MC5 Receptors. *Eur. J. Pharmacol.*, 269:331-337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or U.S. 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buproprion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2, 5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3, 4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™. Capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists for example certain compounds in U.S. Pat. No. 4,626,549 which is incorporated by reference herein, α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

Synthetic Schemes. Distinct and separate methods for synthesis of piperazines and ketapiperazines are required. In general, piperazine molecules as described herein cannot be obtained from the ketopiperazine molecules or synthetic schemes as described herein. One obvious limitation to employing ketopiperazine synthetic schemes to synthesize piperazine molecules is that the presence of other reactive groups, such as amide, halogen and aromatic functional groups, can interfere with the process of reducing a ketopiperazine to a piperazine. Thus three separate and different methods for the synthesis of piperazines were developed and are disclosed herein. Similarly, three separate methods for the synthesis of ketopiperazines were also developed and are disclosed here.

The general strategy for either class of compounds includes developing a linear intermediate using chiral building blocks such as amino acid derivatives. The linear intermediate is cyclized using a Mitsunobo reaction strategy or by spontaneous cyclization through reactive groups such as a reaction between an amine and an aldehyde function. In these cyclizations, the driving force for intramolecular reaction versus intermolecular reaction is the thermodynamic favored reaction forming a six-membered ring structure.

Scheme 1, 2, 5 and 6 presented hereafter are examples of a Mitsunobo reaction mediated cyclizations. Scheme 3A and 3B are example of an aldehyde-amine reaction cyclization. Both methodologies incorporate conditions that do not involve inversion or racemization of chiral centers.

The methods disclosed herein thus allow for the synthesis of piperazine as well as ketopiperazine molecules with the diverse $R_1$ and $R_2$ functionalities disclosed herein. All the schemes further provide a facile approach to obtain compounds that differ at $R_3$ since this group is introduced after the cyclic intermediate has been synthesized.

The invention is further illustrated by the following non-limiting examples.

EXAMPLE 1

Procedure for the Synthesis of piperazin-2-one Compounds

Piperazine-2-one compounds described in this invention were prepared by several methods described here. It would become evident to those skilled in this art that these methods can be modified by employing alternate protecting groups and using flexibility to couple an amino acid derivative at a later stage of the sequence of reactions shown here. In general, the following three different routes (Schemes 1-A, 1-B, and 1-C) were developed to synthesize various examples of this class of compounds disclosed in this application.

Method 1-A (Scheme-1-A): To a solution of compound 1A-1 and 1-hydroxy-7-azabenzotriazole (1 equivalent) in dry N, N-dimethylformamide was added 1-(3-dimethylaminopropyl)-3-ethylcarbodiimide hydrochloride (2 equivalents). After the mixture was stirred at room temperature for half an hour, ethanolamine (2 equivalents) was added. The reaction mixture was stirred for 16 hours. It was then poured into water and extracted twice with ethyl acetate. The organic layer was washed twice by 1 N hydrochloric acid, twice with 1 N sodium hydroxide, brine and dried over sodium sulfate. After evaporating the solvent, the product (1A-2) was purified on silica gel column using 10% methanol in methylene chloride as an eluant.

To compound 1A-2 (1 equivalent) and sodium borohydride (5 equivalents) taken in dioxane was slowly added acetic acid (5 equivalents). The mixture was refluxed for 2 hours and then quenched with water. The solvent was evaporated under reduced pressure and the residue was taken in ether. The product was extracted from ether by 1 N hydrochloric acid. The pH value of the aqueous solution was adjusted using 1 N potassium hydroxide to around pH 11 and the product was extracted three times in ether. The organic layer was dried over sodium sulfate and solvent was evaporated. The compound 1A-3 thus obtained was used in the next step without further purification.

Fmoc-Orn(Boc)-OH (1 equivalent), 1-hydroxy-7-azabenzotriazole (1 equivalent) and 1,3-diisopropylcarbodiimide (1 equivalent) in N,N-dimethylformamide solution was stirred for half an hour. To this solution was added compound 1A-3 and the mixture stirred overnight. After evaporating solvent, the desired compound was obtained by purification over a silica gel column. This compound was treated with 20% diethylamine in ethyl acetate overnight. Compound 1A-4 was obtained after evaporation of solvent.

Compound 1A-4 was dissolved in dry tetrahydrofuran with triphenylphosphine (3 equivalents). To this solution was slowly added diethyl azodicarboxylate (3 equivalents) in tetrahydrofuran. The reaction was stirred for an additional 12 hours. After the solvent was evaporated the product (1A-5) was purified on silica gel column using ethyl acetate/methanol (4/1=v/v) as the eluant.

Compound 1A-5 was dissolved in acetonitrile. To this solution was added Z-OSu (1.5 equivalents). The mixture was stirred overnight. After evaporation of solvent the residue was purified on a column to give the desired compound. This compound was treated by TFA/DCM (50/50) for 1 hour and solvent removed to give compound 1A-6.

Compound 1A-6 was dissolved in acetonitrile and neutralized by triethylamine. To this solution was added additional 2 equivalents of triethylamine and 1,3-bis(t-butoxycarbonyl)-2-methyl-2-thiopseudourea (1 equivalent) and silver nitrate (1 equivalent). The mixture was stirred for 1 hour. After filtration and evaporation of solvent the desired compound was purified on a silica gel column. This compound was subject to overnight treatment of 1 atmosphere hydrogen in the presence of a catalytic amount of palladium on carbon (10%) in methanol. After filtration, the filtrate was evaporated to yield compound 1A-7, which was used without further purification.

Compound 1A-7 was coupled with a desired Fmoc- or Boc-N-protected amino acid derivative (2 equivalents) using 1-hydroxy-7-azabenzotriazole (2 equivalents) and 1,3-diisopropylcarbodiimide (2 equivalents) in N,N-dimethylformamide solution overnight at room temperature. Flash chromatograph (2:1 ethyl acetate-hexane) gave the product with protecting groups. As applicable, the N-protecting Fmoc group was removed by treatment with 20% diethyl amine in ethyl acetate or the N-protecting Boc group was removed by treatment with 30% trifluoroacetic acid in methylene chloride for 1 hour. The final pure compound 1A-8 was obtained by purification on HPLC.

For some compounds, the above procedure was performed using Boc-Arg(Cbz)$_2$-OH instead of Fmoc-Orn(Boc)-OH. The Boc-group was removed by treatment with 30% trifluoroacetic acid in methylene chloride for 1 hour. The solvent was evaporated, the residue treated with 20% sodium hydroxide and the product extracted in ethylacetate. The organic layer was washed with water and dried. After evaporation of solvent the residue was purified on a silica gel column. After a cyclization reaction and coupling with the desired N-protected amino acids as described above, the protected compound was purified on silica gel column. The protecting groups were removed by treatment with 30% HBr in acetic acid. The final compounds were purified by HPLC.

For the synthesis of some compounds, Z-Arg(Boc)$_2$-OH or Fmoc-Arg(Boc)$_2$-OH was used instead of Fmoc-Orn(Boc)-OH. Therefore, the steps for compound 1A-6 and 1A-7 were not necessary. The corresponding protecting groups in the molecule were removed as described previously.

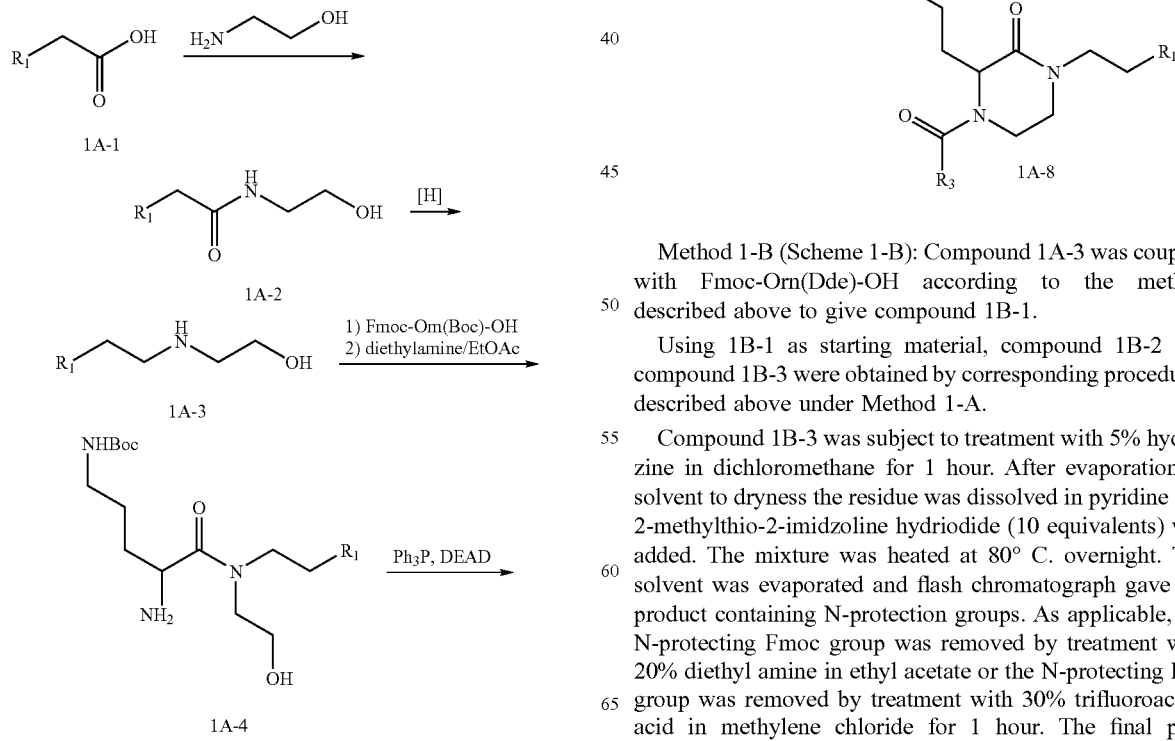

Method 1-B (Scheme 1-B): Compound 1A-3 was coupled with Fmoc-Orn(Dde)-OH according to the method described above to give compound 1B-1.

Using 1B-1 as starting material, compound 1B-2 and compound 1B-3 were obtained by corresponding procedures described above under Method 1-A.

Compound 1B-3 was subject to treatment with 5% hydrazine in dichloromethane for 1 hour. After evaporation of solvent to dryness the residue was dissolved in pyridine and 2-methylthio-2-imidzoline hydriodide (10 equivalents) was added. The mixture was heated at 80° C. overnight. The solvent was evaporated and flash chromatograph gave the product containing N-protection groups. As applicable, the N-protecting Fmoc group was removed by treatment with 20% diethyl amine in ethyl acetate or the N-protecting Boc group was removed by treatment with 30% trifluoroacetic acid in methylene chloride for 1 hour. The final pure compound 1B-4 was obtained by purification on HPLC.

Compound 1B-3 was used for reactions such as acylation or sulfonylation after removing the 1-(4,4-dimethyl-2,6-dioxo-cyclohexylidene)-3-methyl-butyl(Dde) group.

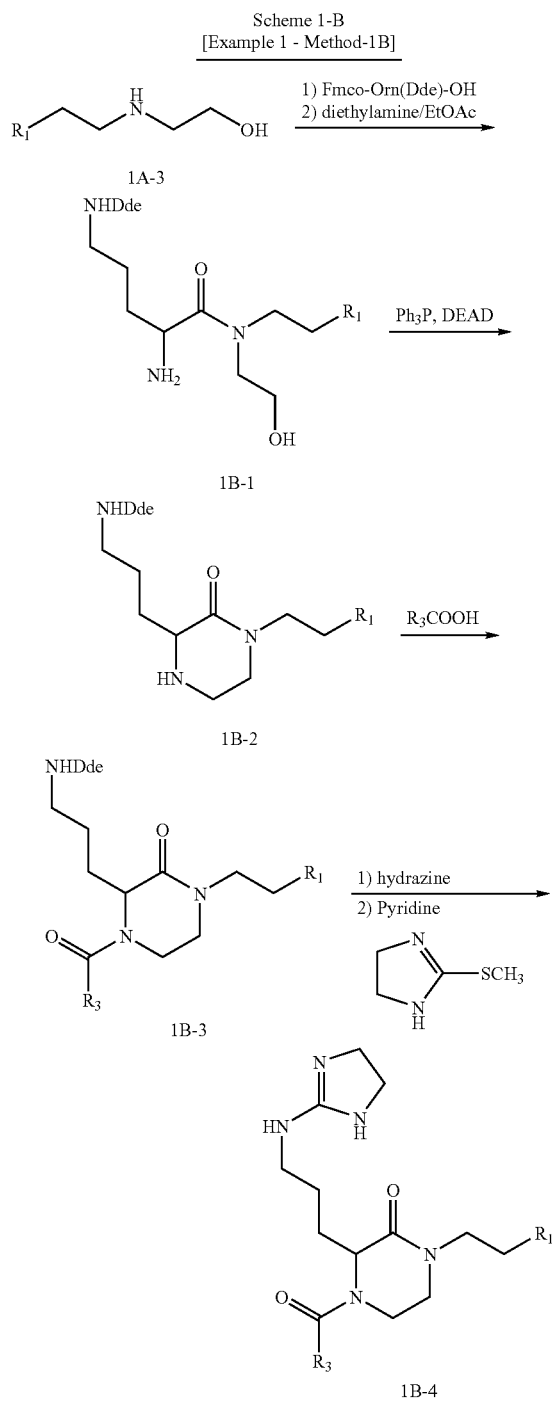

Method 1-C (Scheme 1-C): Compound 1A-3 was coupled with compound 1C-1 (2 equivalents) using 1-hydroxy-7-azabenzotriazole (2 equivalents) and 1,3-diisopropylcarbodiimide (2 equivalents) in N,N-dimethylformamide overnight at room temperature. Flash chromatography gave the desired compound which was treated with 20% diethylamine in ethyl acetate to give compound 1C-2.

Compound 1C-4 was obtained from compound 1C-3 essentially by the corresponding method described above under Method 1-A.

Compound 1C-4 was dissolved in methanol and a catalytic amount of palladium on charcoal (10%) was added. This mixture was stirred under 1 atmosphere hydrogen overnight. After removing solvent the residue was dissolved in dichloromethane containing triethyl amine (2 equivalents) and methanesulfonyl chloride (2. equivalents) was added at 0° C. The reaction was carried out for 30 minutes at 0° C. and additional 1 hour at room temperature. The solvent was evaporated, the residue taken in water, and compound was extracted from water in ethyl acetate. The organic layer was washed with brine and dried over sodium sulfate. After removing solvent the residue was dissolved in DMF and mixed with 2-amino-1,3,4-thiadiazole (4 equivalents). The mixture was heated at 80° C. for 5 hours. The solvent was evaporated and flash chromatograph gave the product containing N-protecting groups. As applicable, the N-protecting Fmoc group was removed by treatment with 20% diethyl amine in ethyl acetate or the N-protecting Boc group was removed by treatment with 30% trifluoroacetic acid in methylene chloride for 1 hour. The final pure compound 1C-5 was obtained by purification on HPLC.

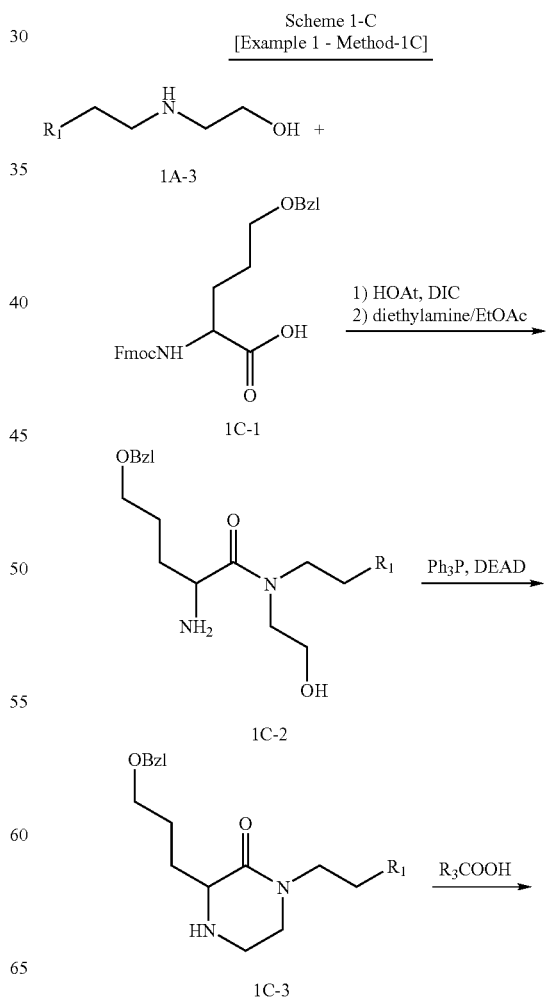

-continued

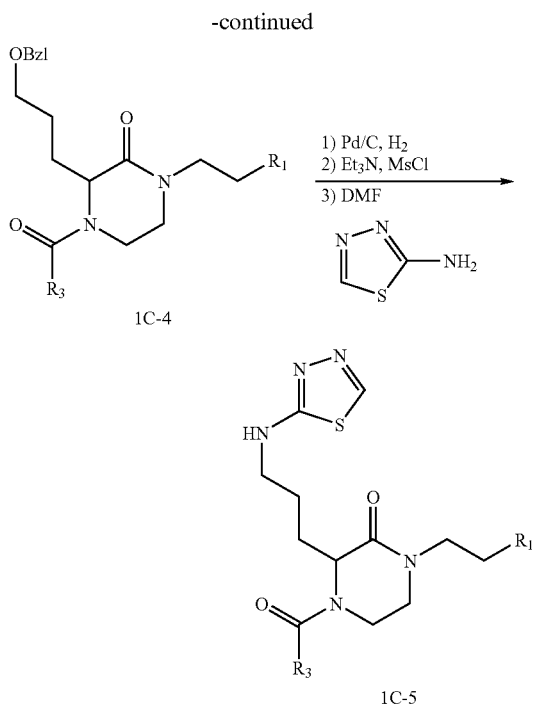

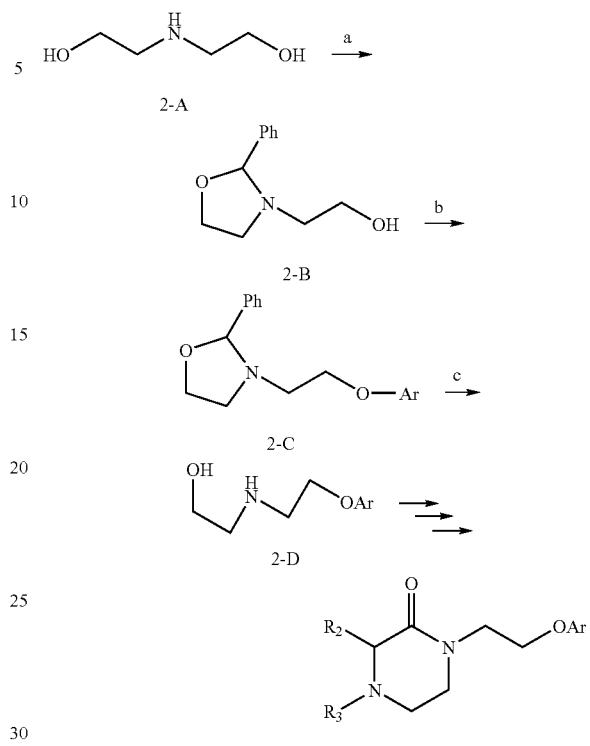

a. Benzaldehyde/benzene; b. ArOH/Ph$_3$P/DEAD/toluene; c. conc. HCl

EXAMPLE 2

Procedures for the Syntheses of piperazin-2-one Compounds

Scheme 2 describes general synthetic route for these compounds. In a round-bottom flask equipped with a Dean-Stark trap, a mixture of diethanolamine (2-A, 1 equivalent) and benzaldehyde (1 equivalent) in benzene was refluxed azetropically for 4 hours, followed by evaporation of the solvent. The product (2-C) was obtained as colorless oil, which was used for the next reaction without further purification.

Compound 2-B (1 equivalent) and 2-naphthol (1.3 equivalents) and triphenylphosphine (1.5 equivalents) were dissolved in 80 mL of toluene. To the solution was added dropwise a solution of diethyl azodicarboxylate (1.1 equivalents) in toluene at 0° C. under nitrogen. After the addition, the reaction mixture was stirred at room temperature overnight. Upon completion of the reaction as monitored with thin layer chromatography, 1 mL of concentrated hydrochloric acid was added to the reaction mixture and the resulting reaction mixture was stirred at 50° C. for 1 hour. The precipitate thus formed was collected by filtration and washed twice with dichloromethane. The collected white solid was dissolved in 20 mL of 1 N sodium hydroxide and the solution was extracted with ethyl acetate (4×30 mL). The combined organic layers were washed with water three times and brine once and dried over magnesium sulfate, and the solvent was evaporated in vacuo to afford the product (2-D) as a white crystalline solid.

The final compound 2-E was obtained by essentially following the procedure described above in Method 1-A.

EXAMPLE 3

Additional Procedures for the Syntheses of piperizin-2-one Compounds

Method 3-A (Scheme 3-A): Weinreb AM resin (1.5 mmol, Novobiochem) was swollen in dichloromethane for one hour. The Fmoc group was removed by treatment with 20% piperidine in 1-methyl-2-pyrrolidinone. The resin was washed with 1-methyl-2-pyrrolidinone three times and dichloromethane three times.

2-bromo-acetic acid (7.5 mmol, Aldrich) and 1-hydroxy-7-azabenzotriazole (7.5 mmol, Aldrich) were dissolved in 10 mL of dry N,N-dimethylformamide. To this solution 1,3-diisopropylcarbodiimide (7.5 mmol) was added slowly. After stirring for 30 minutes, this solution was added into the resin. The mixture was put on a shaker and shaken for 20 hours.

The resin was then washed twice with N,N-dimethylformamide and twice with dichloromethane. To the resin was added ArCH$_2$CH$_2$NH$_2$ (75 mmol) (or an amine similarly related as a precursor for introduction of R$_1$ group in the final molecule of the general formula) in about 16 mL of dimethyl sulfoxide, and the mixture was agitated for 24 hours. It was then washed twice with each of the following: dimethyl sulfoxide, N,N-dimethylformamide, and dichloromethane.

The secondary amine thus formed on the resin was coupled with Z-Lys(Boc)-OH (15 mmol) by using 1-hydroxy-7-azabenzotriazole (15 mmol) and DIC (15 mmol) in 25 mL of dichloromethane/N,N-dimethylformamide (v/v =4/1) as described above. The reaction was carried out for 24 hours. The resin was washed twice with each of the following: N,N-dimethylformamide, dichloromethane, methanol, and ether. The resin was dried under vacuum overnight.

This dried resin was swollen in 20 mL of dry tetrahydrofuran for one hour under nitrogen. To it a solution of lithium aluminum hydride in tetrhydrofuran (1.875 mmol) was added slowly at 0° C. After stirred for additional 1 hour, the reaction was quenched by addition of aqueous potassium hydrogen sulfate (1.25 eq.). The resin was removed by filtration and washed with dichloromethane a few times. The combined organic solution was evaporated, residue taken in brine and compound extracted in ether. The ether layer was dried over sodium sulfate. After removing ether the residue was dried under vacuum to give a crude aldehyde compound (3A-1), which was verified by mass analysis. This crude compound was dissolved in 10 mL methanol and stirred under hydrogen (1 atm.) over a catalytic amount of 5% palladium on barium sulfate for 2 days. The reaction was followed by mass spectrometry for the disappearance of aldehyde and appearance of piperazin-2-one (3A-2). This crude compound was used in the next step reaction without purification.

The piperazin-2-one (3A-2) was coupled with desired amino acids (2 equivalents) by use of 1-hydroxy-7-azabenzotriazole (2 equivalent) and 1,3-diisopropylcarbodiimide (2 equivalents) in N,N-dimethylformamide solution overnight at room temperature. Flash chromatograph (2:1 ethyl acetate-hexane) gave the product containing N-protection groups. As applicable, the N-protecting Fmoc group was removed by treatment with 20% diethyl amine in ethyl acetate or the N-protecting Boc group was removed by treatment with 30% trifluoroacetic acid in methylene chloride for 1 hour. In each case the final pure compound (3A-3) was obtained by purification by HPLC.

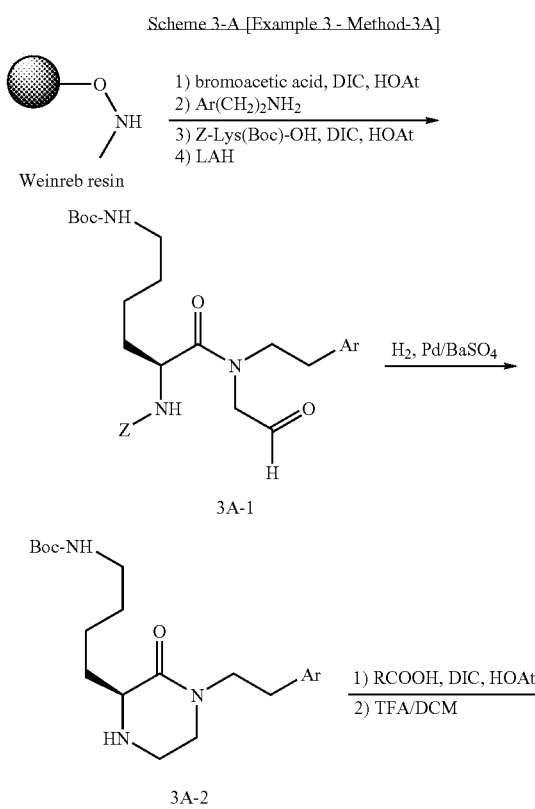

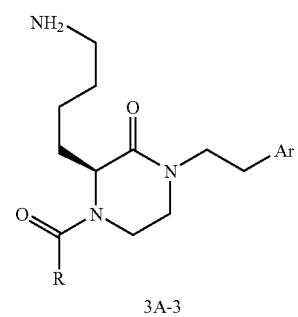

3A-3

Method 3-B (Scheme 3-B): 2-Indoleacetic acid, N-methylmorpholine (1 equivalent) and TBTU (1 equivalent) were dissolved in dichloromethane. After stirring for 15 min. allylamine (1 equivalent) was added. The reaction was stirred overnight. The solvent was evaporated and the residue taken in 1 N sodium hydroxide and extracted with ethyl acetate. The organic layer was washed by water, brine and dried over magnesium sulfate. After removing solvent the residue was purified on column to give compound 3B-1.

Compound 3B-1 was dissolved in THF and refluxed with lithium aluminum hydride (2.5 equivalents) for 24 hours. The reaction was quenched by potassium hydrogen sulfate and solvent was removed. The compound was extracted in ether and washed with 1 N HCl and brine. The organic layer was dried over sodium sulfate. After removing solvent compound 3B-2 was obtained for the next step reaction without further purification.

To a solution of Z-Arg(BOc)$_2$-OH and HOAt in DMF was added DIC slowly at 0° C. The reaction was stirred for 30 minutes and compound 3B-2 was added. The mixture was stirred for 24 hours and solvent was removed. The residue was purified on a column to give the desired compound. This compound was dissolved in dichloromethane and mixed with di-t-butyldicarbonate (1 equivalent) and 4-dimethylaminopyridine (0.1 equivalent). The reaction was carried out overnight. After removing solvent the residue was purified on a column to give compound 3B-3.

Compound 3B-3 was dissolved in dioxane/water (3/1 v/v) and sodium periodate (2 equivalents) was added. To the mixture was added osmium tetraoxide (0.03 equivalent) and the mixture was stirred for 6 hours. It was extracted with ethyl acetate and washed with brine. After evaporation of solvent the residue was purified on a column to give compound 3B-4.

Compound 3B-6 was obtained through compounds 3B-4 and 3B-5 by the method described for Method 3-A.

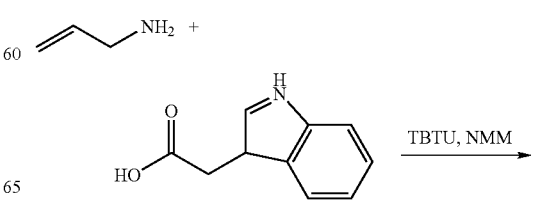

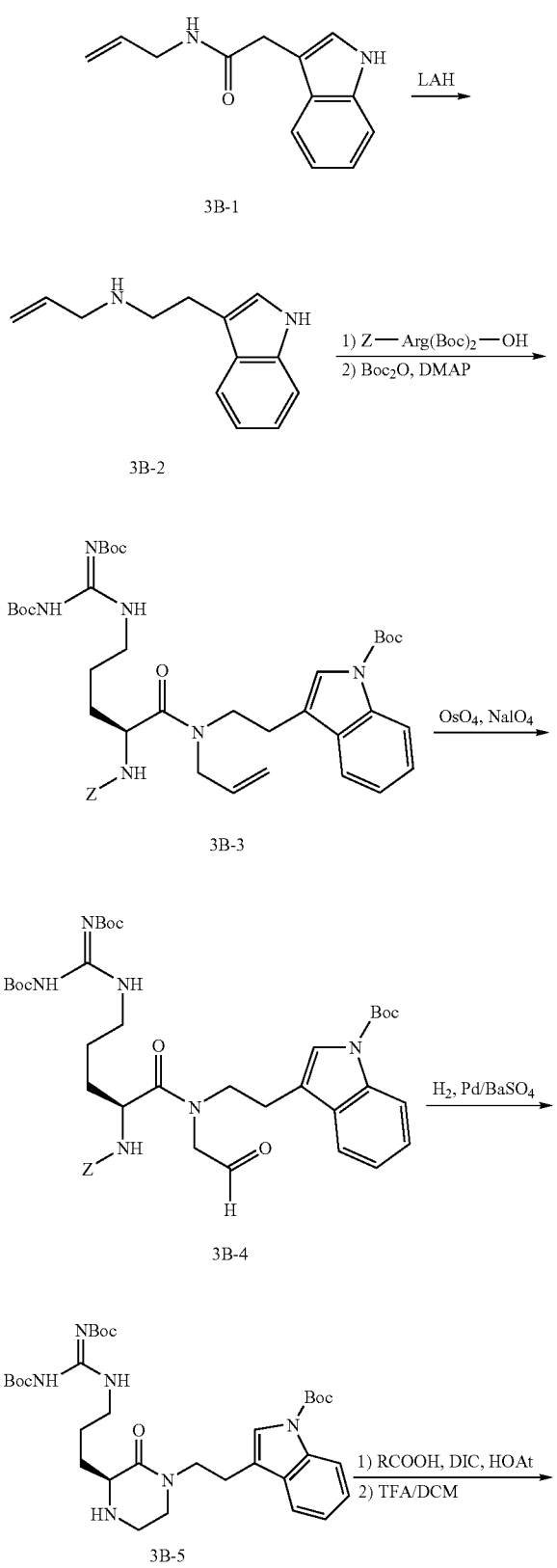

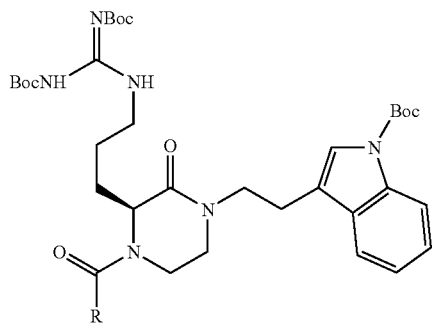

3B-6

EXAMPLE 4

Procedures for the Syntheses of Piperazine Compounds

Scheme 4 describes the general method for synthesizing these compounds. A mixture of 2-naphthylacetic acid, 1-hydroxy-7-azabenzotriazole and 1,3-diisopropylcarbodiimide (one equivalent each) in N,N-dimethylformamide was stirred for 30 min at 0° C. To this mixture was added 1-Boc-piperazine (1 equivalent) and the reaction was continued for 16 hours. The solvent was evaporated and product was purified on a silica gel column. This product was treated with 30% trifluoroacetic acid in methylene chloride for 1 hour. After evaporation of solvent the product 4-1 was precipitated out in ether, which was collected by filtration. The white powder was dried and used in next reaction according to methods 4-A and 4-B as follows.

Method 4-A (Scheme 4): Compound 4-1 was coupled with a desired Fmoc or Boc N-protected amino acid (2 equivalents) by use of 1-hydroxy-7-azabenzotriazole (2 equivalents) and 1,3-diisopropylcarbodiimide (2 equivalents) in N,N-dimethylformamide overnight at room temperature. Flash chromatograph (2:1 ethyl acetate-hexane) gave the product containing an appropriate N-protected group. As applicable, the N-protecting Fmoc group was removed by treatment with 20% diethyl amine in ethyl acetate or the N-protecting Boc group was removed by treatment with 30% trifluoroacetic acid in methylene chloride for 1 hour. In each case the final pure compound (4A-1) was obtained by purification by HPLC.

Methods 4-B (Scheme 4): Compound 4-1 was dissolved in methylene chloride and the solution was washed with 1 N sodium hydroxide. The organic layer was dried over sodium sulfate and the solvent was removed under vacuum. To this residue taken in dry tetrahydrofuran was added lithium aluminum hydride (1 N in tetrahydrofuran, 2 equivalents). The mixture was stirred at room temperature for 30 minutes, and refluxed for 24 hours. The reaction then was quenched by addition of water. The solid was removed by filtration and the product (4B-1) was obtained after evaporation of solvent. This compound (4B-1) was used without further purification.

The compound was reacted with a desired Fmoc or Boc N-protected amino acid essentially as described above under method 4-A to obtain compound (4B-2).

Scheme 4 [Example 4 - Methods-A and B

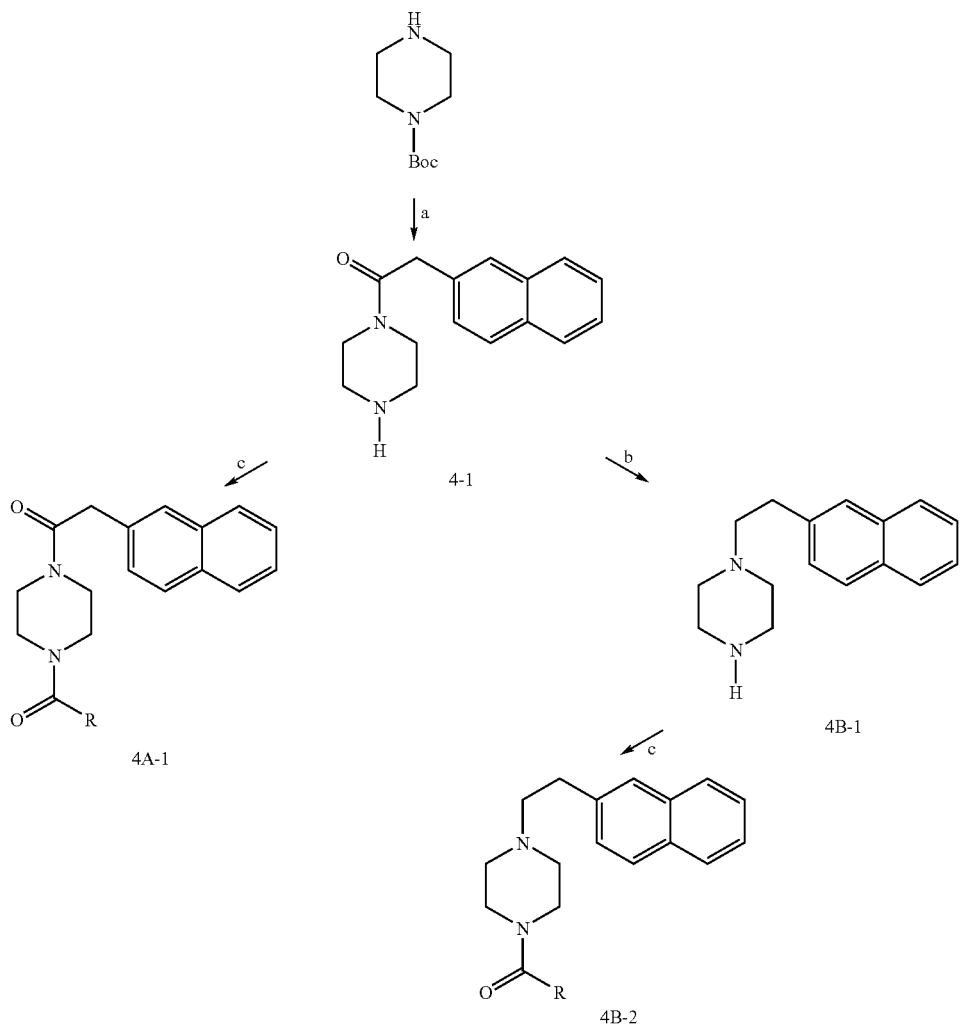

Reagents: (a) i) 2-naphthylacetic acid, HOAt, DIC, DMF; ii) TFA, DCM; (b) LAH, THF; (c) RCOOH, DIC, HOAt, DMF.

EXAMPLE 5

Additional Procedures for the Syntheses of Piperazine Compounds

Method 5-A (Scheme 5-A): Compound 5A-1 (1 equivalent) and N-methyl morpholine (1 equivalent) in dry dichloromethane was added to 2-(1H-benzotriazole-1-yl)-1,1,3,3-tetramethyluronium tetrafluoroborate (1 equivalent). The mixture was stirred at room temperature for 30 minutes. A mixture of N,O-dimethylhydroxyamine hydrochloride (1.5 equivalents) and N-methyl-morpholine (1.5 equivalents) in dichloromethane was stirred for 30 minutes. These two mixtures were combined and stirred at room temperature for 18 hours. The organic solvent was evaporated and the residue loaded on a flash chromatograph column and eluted with ethyl acetate/hexane (2/1) to give an N,O-dimethylhydroxyamide product. This product was dissolved in dry tetrahydrofuran at 0° C. and lithium aluminum hydride (1 M in tetrahydrofuran, 1.2 equivalents) was added slowly. After 30 minutes the reaction was quenched by addition of aqueous potassium hydrogen sulfate (1.2 equivalents). Tetrahydrofuran was removed under reduced pressure and ether was added. The solution was washed by 1 N hydrochloric acid (2 times), aqueous sodium hydrogen carbonate, and brine. After drying over sodium sulfate, the solvent was removed under vacuum to give compound 5A-2. Compound 5A-2 was used for the next step reaction without further purification.

Compound 5A-2 was mixed with sodium triacetoxyborohydride (1.2 equivalents) and ethanolamine (1.2 equivalents) in the presence of activated 4A molecular sieves (1 gram) in dry tetrahydrofuran. The mixture was stirred at room temperature for 6 hours and to it was added N-(benzyloxycarbonyloxy)succinimide (2 equivalents). It was stirred for additional 24 hours. After filtration and evaporation of solvent the desired product (5A-3) was purified on silica gel column.

Compound 5A-3 was treated with 20% diethylamine in ethyl acetate for 12 hours and the solvent was evaporated to dryness. The residue and triphenylphosphine (3 equivalents) were dissolved in dry tetrahydrofuran. To this solution was added diisopropyl azodicarboxylate (3 equivalents) in tetrahydrofuran slowly at 0° C. The reaction was carried out for 16 hours at room temperature. After evaporation of solvent, the residue was purified on silica gel column to afford product 5A-4.

Compound 5A-4 was coupled with a desired Fmoc or Boc N-protected amino acid derivative (2 equivalents) using 1-hydroxy-7-azabenzotriazole (2 equivalents) and 1,3-diisopropylcarbodiimide (2 equivalents) in N,N-dimethylformamide overnight at room temperature. Flash chromatograph gave the product containing a corresponding N-protecting group. As applicable, the N-protecting Fmoc group was removed by treatment with 20% diethyl amine in ethyl acetate or the N-protecting Boc group was removed by treatment with 30% trifluoroacetic acid in methylene chloride for 1 hour. In each case the final pure compound (5A-5) was obtained by purification by HPLC.

Scheme 5-A [Example 5 - Method - 5A]

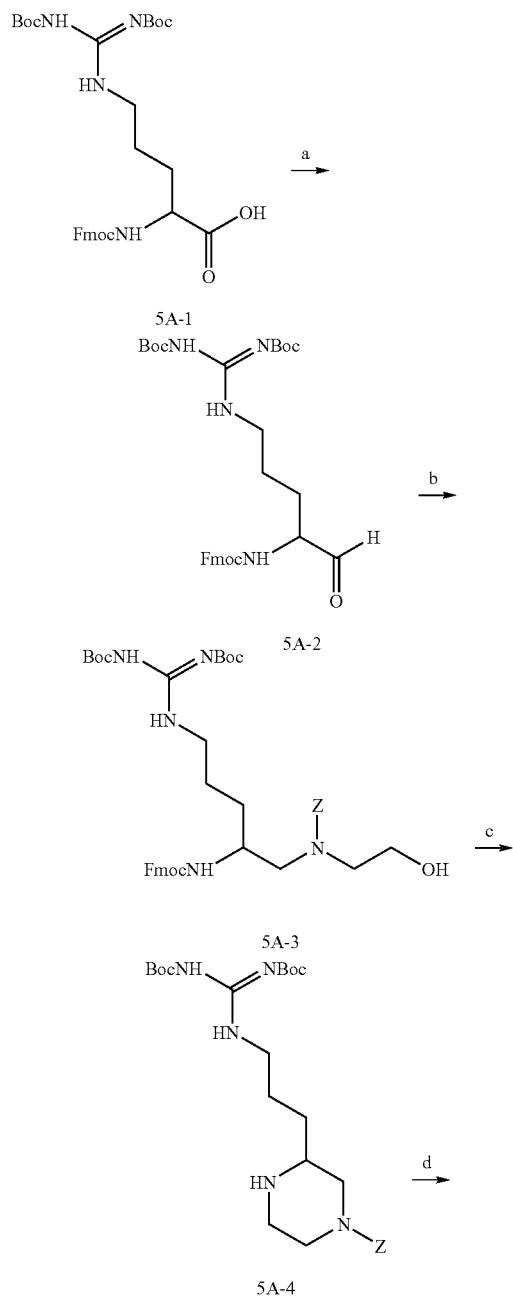

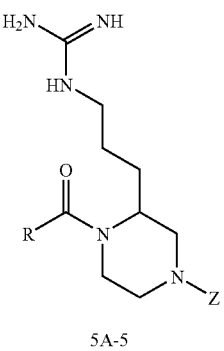

Reagents: (a) i) NHMeOMe·HCl, TBTU, NMM; ii) LAH, THF; (b) i) 4A molecular sieves, Na(AcO)₃BH, NH₂(CH₂)₂OH, THF; ii) Z-OSu; (c) i) 20% Et₂NH/EtOAc; ii) Ph₃P, DIAD, THF; (c) i) RCOOH, HOAt, DIC, DMF; ii) TFA/DCM Method 5-B (Scheme 5-B): Compound 5A-2 was mixed with sodium triacetoxyborohydride (1.2 equivalents) and RCH₂CH₂NHCH₂CH₂OH (1.2 equivalents) in the presence of activated 4 Å molecular sieves (1 gram) in dry tetrahydrofuran. The mixture was stirred at room temperature for 6 hours. After filtration and evaporation of solvent the desired product (5B-1) was purified on silica gel column.

Compound 5B-1 was treated with 20% diethylamine in ethyl acetate for 12 hours and the solvent was evaporated to dryness. The residue and triphenylphosphine (3 equivalents) were dissolved in dry tetrahydrofuran. To this solution was added diisoproryl azodicarboxylate (3 equivalents) in tetrahydrofuran slowly at 0° C. The reaction was carried out for 16 hours at room temperature. The product 5B-2 was purified on a silica gel column after evaporation of solvent.

Compound 5B-2 was coupled with a desired Fmoc or Boc N-protected amino acid (2 equivalents) by use of 1-hydroxy-7-azabenzotriazole (2 equivalents) and 1,3-diisopropylcarbodiimide (2 equivalents) in N,N-dimethylformamide overnight at room temperature. Flash chromatography gave the product containing corresponding N-protected group. As applicable, the N-protecting Fmoc group was removed by treatment with 20% diethyl amine in ethyl acetate or the N-protecting Boc group was removed by treatment with 30% trifluoroacetic acid in methylene chloride for 1 hour. In each case the final pure compound (5B-3) was obtained by purification by HPLC.

Scheme 5-B [Example 5 - Method - 5B]

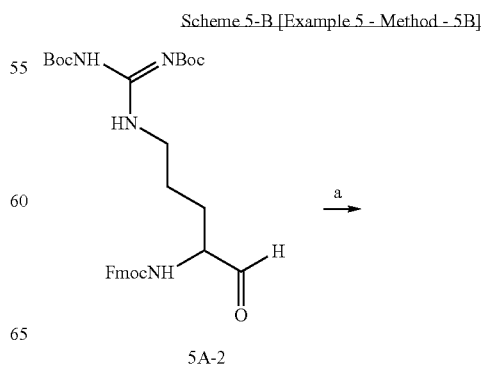

-continued

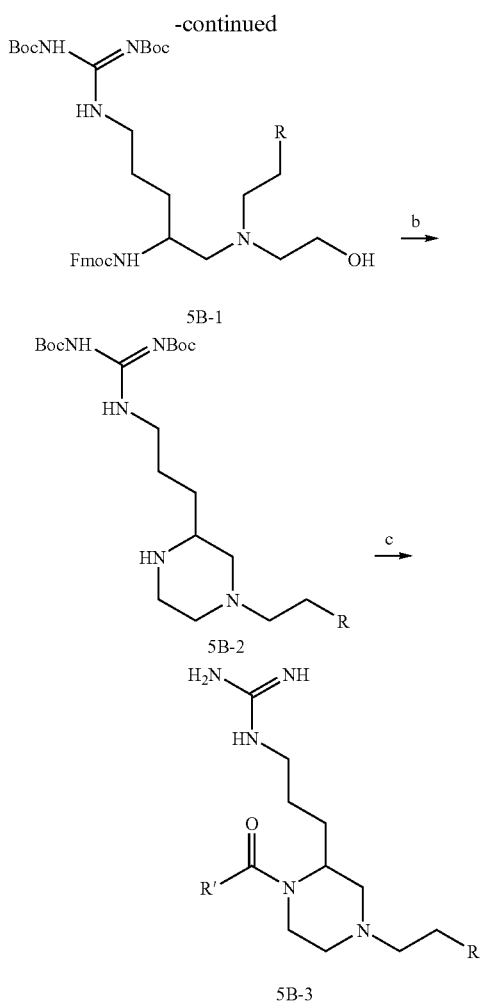

Reagents: (a) 4A molecular sieves, Na(AcO)₃BH, RCH₂CH₂NH(CH₂)₂OH, THF; (b) i) 20% Et₂NH/EtOAc; ii) Ph₃P, DIAD, THF; (c) i) R'COOH, HOAt, DIC, DMF; ii) TFA/DCM Method 5-C (Scheme 5-C): At room temperature to a mixture of starting material 5C-1 (5.0 g, 11.00 mmol), the amine (3.33 g, 22.00 mmol), and NMM (1.57 mL, 14.3 mmol) in ethyl acetate (80 mL) was added 2-(1H-benzotriazole-1-yl)-1,1,3,3-tetramethyluronium tetrafluoroborate (TBTU) (4.6 g, 14.3 mmol) in portions. The reaction mixture was stirred at room temperature overnight. The reaction mixture was diluted with ethyl acetate and washed with 1 N HCl (2 times) and H₂O (to neutral pH) and brine. After drying over MgSO₄ and the solvent was evaporated to afford a crude product 5C-2 which was used in the next reaction without further purification.

Compound 5C-2 was dissolved in ethyl acetate (20 mL) and 5 mL of Et₂NH added. The reaction mixture was stirred at room temperature for 4 hours followed by removal of solvent. Fresh amount of ethyl acetate was added and the solvent was again removed under reduced pressure. The procedure was repeated again. The resulting crude product was used in the next reaction without further purification.

To a solution of the above crude product in ethyl acetate (100 mL) at room temperature, Ph₃P (4.32 g, 16.50 mmol) and DIAD (2.67 g, 13.2 mmol) was added. The reaction mixture was stirred at room temperature for 3 hours followed by addition of Fmoc-OSu (4.4 g, 13.2 mmol) and 4 mL of ethanol. The resulting reaction mixture was stirred at room temperature for 30 minutes followed by evaporation and purification on a silica gel column (eluant: hexanes: AcOEt=4:1 to 1:1) to afford the product 5C-3 as a white solid (6.1 g).

To a solution of compound 5C-3 (1.8 g, 1.75 mmol) in 5 mL of THF at 0° C. was added dropwise BH₃-THF (5.3 mL, 5.25 mmol) under nitrogen. The reaction mixture was stirred at room temperature overnight followed by quenching with 10 mL of 1 N HCl and 9 mL of 0.2 M KMnO₄. After stirring at room temperature for 60 minutes, the reaction mixture was neutralized with 8 mL of saturated NaHCO₃ (~pH 6) and evaporated in vacuo to remove THF. The concentrated mixture was extracted three times with ethyl acetate and combined organic layers were washed with H₂O, brine, dried over MgSO₄ and evaporated in vacuo. The product 5C-4 was obtained as a solid, 1.22 g (69%).

At room temperature under nitrogen, to a mixture of compound 5C-4 (1.1 g, 1.98 mmol) and Pd black (300 mg) in ethyl acetate/iso-propanol (24 mL/24 mL) was added 88% HCO₂H (12.0 mL). The reaction mixture was stirred at room temperature overnight followed by filtration and the filtrate was evaporated. The crude product was dissolved in ethyl acetate and washed with saturated NaHCO₃ (2 times), H₂O (1 time), brine, dried over MgSO₄ and evaporated to yield 920 mg (100%) of the purified product.

To a solution of the product (170 mg, 0.37 mmol) and naphthylethyl aldehyde (62 mg, 0.37 mmol) in 15 mL of iso-propanol was added 0.25 mL of 2.5 N H₂SO₄ in iso-propanol. To this solution was added 1.0 M NaCNBH₃ in THF. The reaction mixture was stirred at room temperature for 1 hour followed by evaporation. The residue was dissolved in ethyl acetate and washed with H₂O (twice), brine, and dried over MgSO₄ and evaporated. The product 5C-5 was obtained as a colorless oil, 210 mg (93%), and was pure enough for the next reaction without further purification.

Compound 5C-6 was obtained by the methods used in Scheme 1 for introducing a guanidine group, removing the Fmoc group and coupling with a desired amino acid.

Scheme 5 [Example 5 - Method - 5-C]

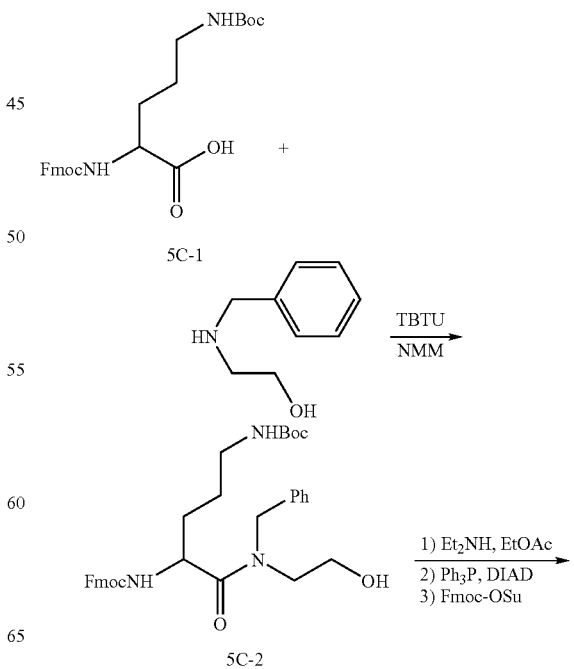

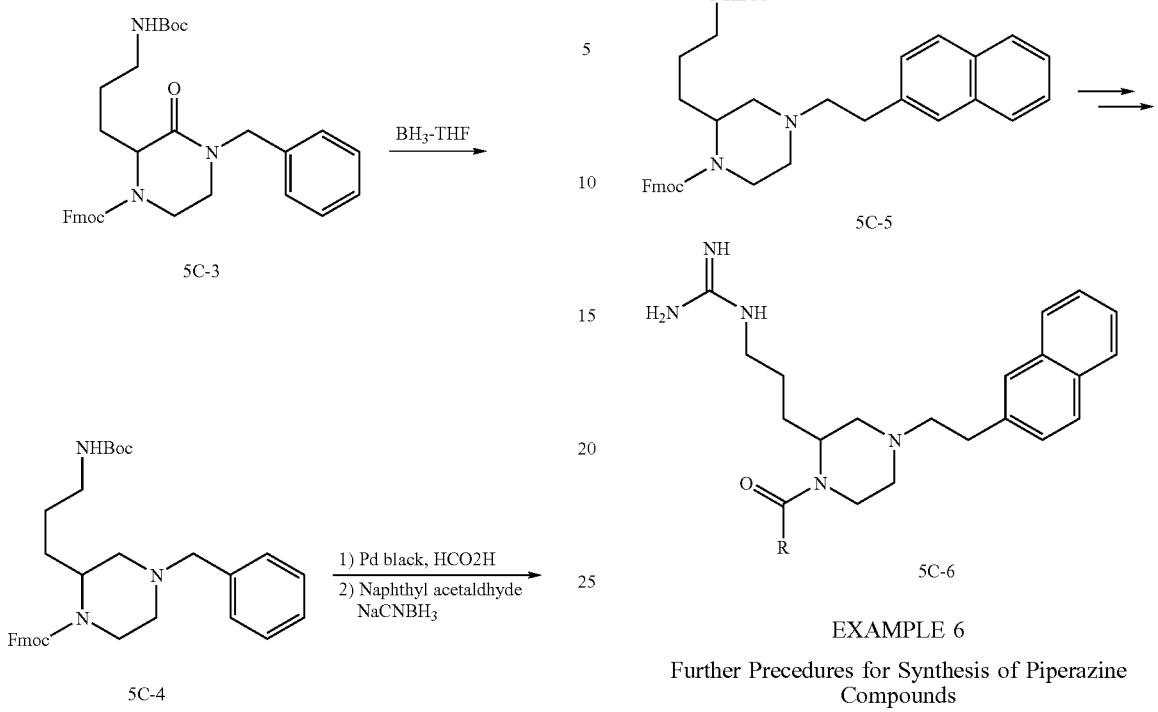
EXAMPLE 6
Further Precedures for Synthesis of Piperazine Compounds
The general method is shown in scheme-6 below.
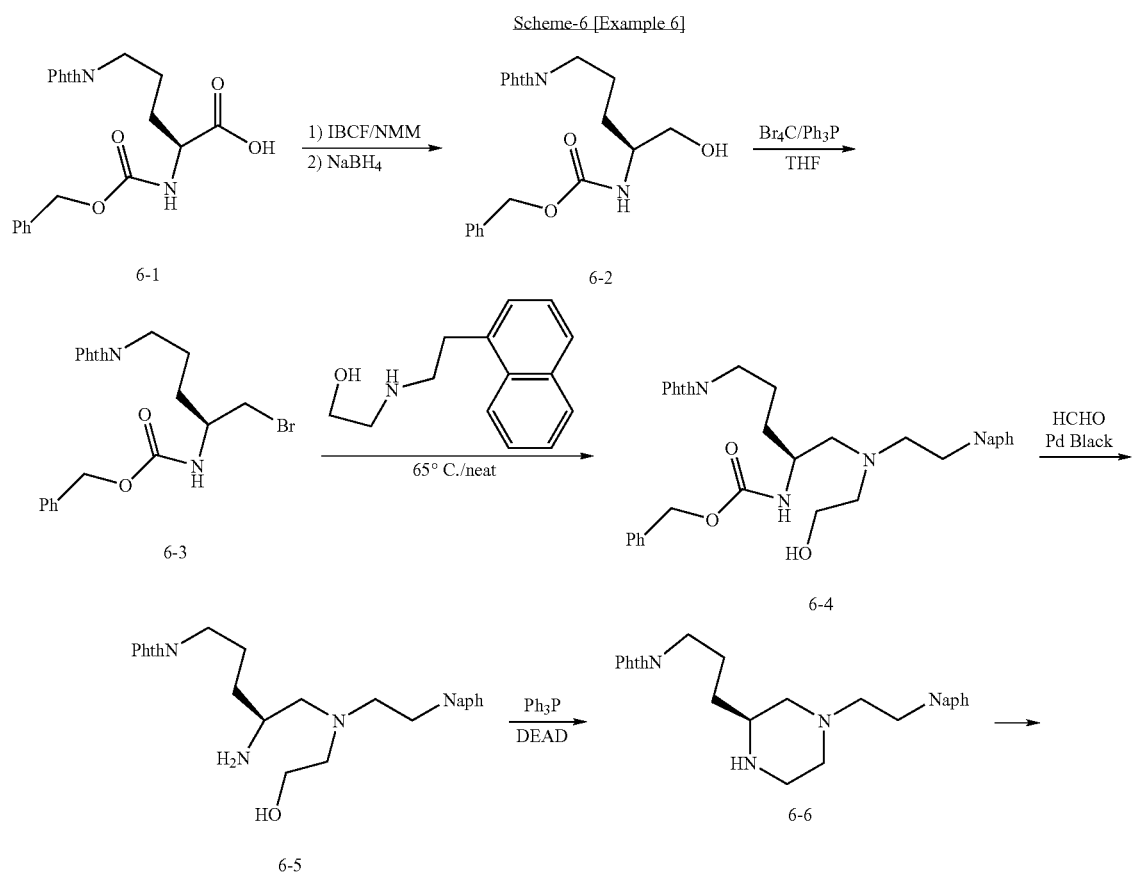

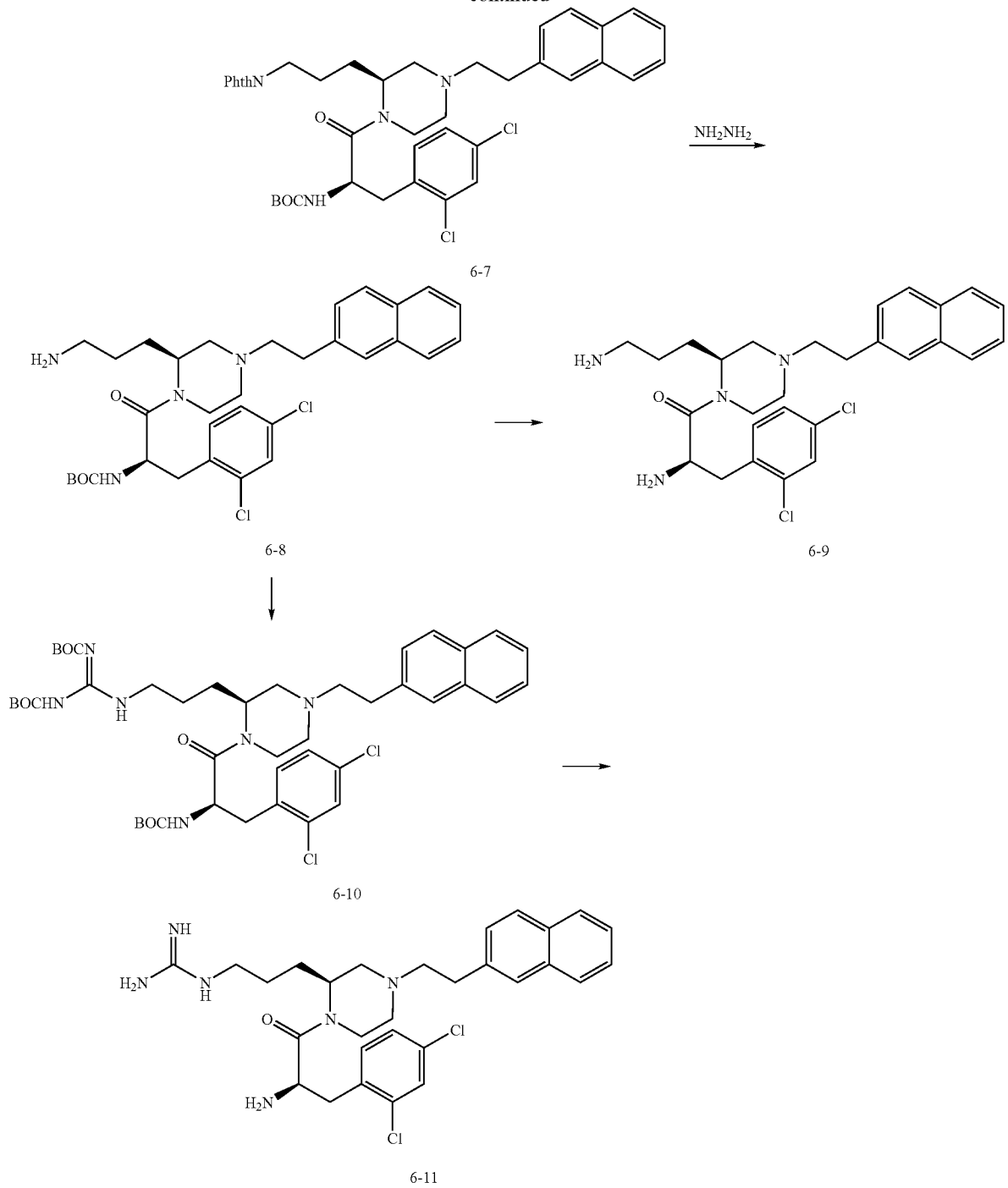

2-Benzyloxycarbonylamino-5-phthalimido-pentanoic acid (6-1) was synthesized from a mixture of Z-ornithine (1.33 g, 5.0 mmol), N-carethoxy-phthalimide (1.10 g, 5.0 mmol), and TEA (1.0 mL, 6.0 mmol) in 10 mL of dry THF refluxed overnight. The solvent was evaporated in vacuo, the residue was dissolved in ethyl acetate, and washed successively with 1 N HCl, water, brine, dried (MgSO$_4$) and evaporated in vacuo to afford the crude product (2.2 g), which was used for the next reaction without further purification.

The crude product (6-1) was dissolved in 5 mL of THF and to the solution was added NMM (0.44 mL). The solution was cooled down to −15° C. with a salt-ice bath, and IBCF (0.52 mL, 1 equivalents) was added. After 10 minutes, the reaction mixture was filtered to remove formed solid salt. The solid was washed twice with adequate amounts of THF. The filtrate was cooled to −10° C. and to it was added NaBH$_4$ (0.23 g, 1.50 equivalents) in 2 mL of water. The reaction mixture was stirred for another 15 minutes, and then concentrated in vacuo. The residue was dissolved in ethyl acetate and washed successively with 10% citric acid, saturated NaHCO$_3$, H$_2$O and saturated NaCl, and then dried (MgSO$_4$) and concentrated in vacuo. The crude product was purified with column chromatography eluted with 1:1 EtOAc:hexanes. The purified product [4-Phthalimido-1-hydroxymethyl-butyl]-carbamic acid benzyl ester (6-2) was obtained as a white solid, 1.1 g (58%).

At −20° C. under N$_2$ to the suspension of 6-2 (253 mg, 0.66 mmol) and TPP (260 mg, 1.5 equivalents) in toluene was added tetrabromocarbon (242 mg, 1.1 equivalents) and the reaction mixture was stirred at room temperature overnight. The reaction mixture was concentrated in vacuo and the crude product was purified by column chromatography eluted with hexanes and EtOAc (2:1). The purified product [1-Bromomethyl-4-phthalimido-butyl]-carbamic acid benzyl ester (6-3) was obtained as a white solid, 263 mg (99%).

A mixture of 6-3 (400 mg, 0.90 mmol) and the amine (400 mg, 1.86 mmol) in 2 mL of DCM was stirred at 65° C. The solvent was evaporated and the dried reaction mixture was heated at 65° C. for 2 hours. The formed crude product was purified with column chromatography and eluted with hexanes (ethyl acetate 1:2). The product (4-Phthalimido-1-{[(2-hydroxy-ethyl)-(2-naphthalen-2-yl-ethyl)-amino]-methyl}-butyl)-carbamic acid benzyl ester (6-4) was obtained as a white solid, 260 mg (50%).

At room temperature under nitrogen a mixture of 6-4 (240 mg, 0.41 mmol) and palladium black (80 mg) in 21 mL of 4% HCHO in methanol was stirred vigorously for 1 hour. The reaction mixture was filtered and the filtrate was neutralized with saturated NaHCO$_3$. The methanol was evaporated and the residue was dissolved in ethyl acetate and washed successively with saturated NaHCO$_3$, water and saturated NaCl, then dried (MgSO$_4$) and evaporated. The product, 2-{4-Amino-5-[(2-hydroxy-ethyl)-(2-naphthalen-2-yl-ethyl)-amino]-pentyl}-isoindole-1,3-dione (6-5) was collected as a white solid, 160 mg (88%).

At 0° C. under nitrogen to the mixture of 6-5 (150 mg, 0.34 mmol) and TPP (133 mg, 1.5 equivalents) in 10 mL of anhydrous THF was added diethyl azodicarbonate (65 mg, 1.1 equivalents) in 1 mL of anhydrous THF. After stirring at room temperature for 4 hours, the reaction mixture was evaporated in vacuo and the crude was purified with column chromatography. The product, 2-{3-[4-(2-Naphthalen-2-yl-ethyl)-piperazin-2-yl]-propyl}-isoindole-1,3-dione (6-6) was obtained as a yellowish solid, 42 mg (29%).

To a mixture of 6-6 (42 mg, 0.10 mmol) and BOC-D-2,4-dichlorophenylalanine (66 mg, 2 eq) in 0.4 mL of 0.5 M HOAt in DMF and 0.5 mL of anhydrous DMF was added diisopropylcarboimide (24 mg, 2 equivalents). The reaction mixture was stirred at room temperature overnight. The solvent was evaporated in vacuo and the crude was purified with column chromatography (eluted with hexanes, ethyl acetate 1:2). The purified product, {1-(2,4-Dichloro-benzyl)-2-[2-[3-phthalimido-propyl]-4-(2-naphthalen-2-yl-ethyl)-piperazin-1-yl]-2-oxo-ethyl}-carbamic acid tert-butyl ester (6-7) was obtained as white solid, 30 mg (40%).

A solution of 6-7 (30 mg) in 10 mL of 0.2 M hydrazine in methanol was stirred at room temperature for 19 hours. Mass spectroscopy showed no starting material left in the reaction mixture. The reaction mixture was evaporated and co-evaporated three times with methanol and once with ethyl acetate, then dried under high vacuum for 2 days. The crude product, [2-[2-(3-Amino-propyl)-4-(2-naphthalen-2-yl-ethyl)-piperazin-1-yl]-1-(2,4-dichloro-benzyl)-2-oxo-ethyl]-carbamic acid tert-butyl ester (6-8), (~30 mg) was used for the next reaction without further purification.

10 mg of the crude product 6-8 was treated with 3 mL of 33% TFA in DCM at room temperature for 2.5 hours. The solvents were removed by evaporation and the crude product was purified by HPLC (10-90-60, in an acetonitrile-water gradient flow). After lyophilization of the collected fractions, the product 2-Amino-1-[2-(3-amino-propyl)-4-(2-naphthalen-2-yl-ethyl)-piperazin-1-yl]-3-(2,4-dichloro-phenyl)-propan-1-one 6-9 was obtained as white solid, 2.1 mg (purity >90% by HPLC).

Alternatively, 20 mg (0.033 mmol) of the crude product 6-8 was reacted with 1,3-bis(tert-butoxycarbonyl)-2-methyl-2-thiopseudourea (10 mg, 1.1 equivalents) and silver nitrate (6 mg, 1.1 eq) and NMM (2.2 equivalents) in 5 mL of acetonitrile at room temperature for 24 hours, followed by evaporation to remove the solvent and column chromatography purification to produce 4.5 mg of the product [2-[2-[3-(N',N"-Di-tert-butoxycarbonyl-guanidino)-propyl]-4-(2-naphthalen-2-yl-ethyl)-piperazin-1-yl]-1-(2,4-dichloro-benzyl)-2-oxo-ethyl]-carbamic acid tert-butyl ester (6-10). Product 6-10 (4.5 mg) was treated with 33% TFA in DCM at room temperature for 2 hours and the reaction mixture was concentrated and purified with HPLC to give 1.05 mg {1-(2,4-Dichloro-benzyl)-2-[2-(3-guanidino-propyl)-4-(2-naphthalen-2-yl-ethyl)-piperazin-1-yl]-2-oxo-ethyl}-carbamic acid tert-butyl ester (6-11).

EXAMPLE 7

Competitive Inhibition Assay

A competitive inhibition binding assay was conducted using membranes prepared from hMC3-R, hMC4-R, hMC5-R, and B-16 mouse melanoma cells (containing MC1-R) using 0.4 nM $^{125}$I—NDP-α-MSH (New England Nuclear, Boston, Mass., USA) in 50 mM HEPES buffer containing 1 mM MgCl$_2$, 2 mM CaCl$_2$, and 5 mM KCl, at pH 7.2. The assay tube also contained a chosen concentration of the test compound of this invention, typically a 1 µM concentration, for determining its efficacy in inhibiting the binding of $^{251}$I—NDP-α-MSH to its receptor. Non-specific binding was measured by complete inhibition of binding of $^{125}$I—NDP-α-MSH in the assay with the presence of 1 µM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 µM α-MSH. The cpm obtained in presence of test compounds were normalized with respect to 100% specific binding to determine the percent inhibition of $^{125}$I—NDP-α-MSH binding. Each assay was conducted in triplicate and the actual mean values are described.

EXAMPLE 8

EC$_{50}$ Determination in Functional Activity Assay

The Ki (nM) of certain compounds of the invention were determined. Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, were plated in 96 well plates at a density of $0.5\times10^5$ cells per well. Cells were incubated with the test compounds in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software.

EXAMPLE 9

Functional Status

The agonist/antagonist status with respect to MC1-4, MC4-R, and MC5-R of certain compounds of the invention was determined. Antagonistic activity was determined by measuring the inhibition of α-MSH-induced cAMP levels following exposure to the compounds as in the preceding examples.

EXAMPLE 10

Penile Erection Induction

The ability of compounds to induce penile erection (PE) in male rats was evaluated with selected compounds. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with compounds at a variety of doses via intravenous (IV) or intracerebroventricular (ICV) routes. Immediately after treatment, rats were placed into individual polystyrene cages (27 cm long, 16 cm wide, and 25 cm high) for behavioral observation. Rats were observed for 30 minutes IV or 90 minutes ICV, and the number of yawns, grooming bouts and PEs were recorded in 10-minute bins.

EXAMPLE 11

ICV Food Intake and Body Weight Change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed ICV with vehicle or selected compounds (1-3 nmol). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 12

IV Food Intake and Body Weight Change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed IV with vehicle or selected compounds (0.5-3 mg/kg). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 13

Determination of Mass and Nuclear Magnetic Resonance Analysis

The mass values were determined using a Waters Micro-Mass ZQ device utilizing a positive mode. Mass determinations were compared with calculated values and expressed in the form of mass weight plus one (M+1).

Proton NMR data was obtained using a Bruker 300 MHz spectrometer. The spectra were obtained after dissolving compounds in a deuteriated solvent such as chloroform, dimethyl sulfoxide, or methanol as appropriate.

EXAMPLE 14

A compound of the following structure:

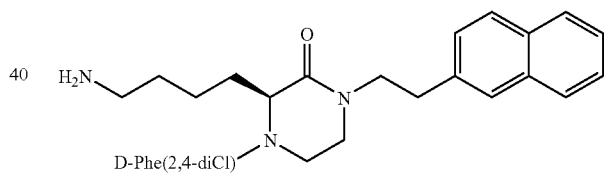

was synthesized by the method of Example 1. The molecular weight was determined to be 541.4 ESI-MS(M+1) by the method of Example 13. ($^1$H NMR, $CD_3OD$) δ: 1.0-1.8 (m, 6H), 2.6-3.3 (m, 8H), 3.4-4.1 (m, 4H), 4.4-4.7 (m, 2H), 7.1-8.0 (m, 10H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 9%    | 3%    | 62%   | 4%    |

EXAMPLE 15

A compound of the following structure:

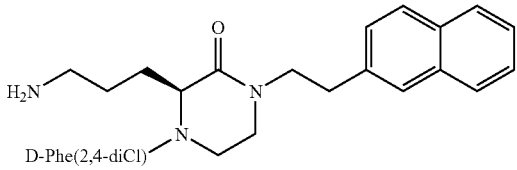

was synthesized by the method of Example 1. The molecular weight was determined to be 527.2 ESI-MS(M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 2% | 0% | 43% | 1% |

EXAMPLE 16

A compound of the following structure:

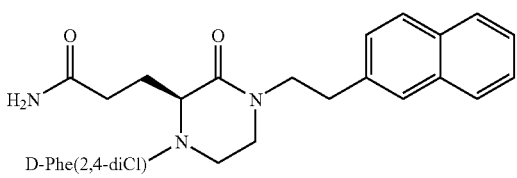

was synthesized by the method of Example 1. The molecular weight was determined to be 541.2 ESI-MS(M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 0% | 0% | 0% |

EXAMPLE 17

A compound of the following structure:

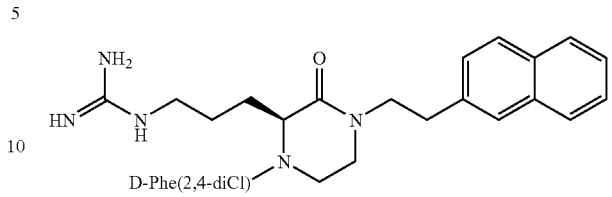

was synthesized by the method of Example 1. The molecular weight was determined to be 568.9 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 22% | 47% | 95% | 35% |

In a cAMP assay as in Example 9 for determination of agonist/antagonist status, it was determined that the compound was an antagonist as to MC1-R and an agonist as to MC4-R and MC5-R.

EXAMPLE 18

A compound of the following structure:

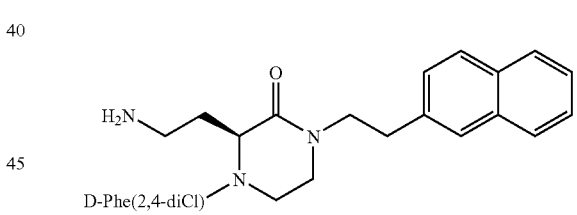

was synthesized by the method of Example 1. The molecular weight was determined to be 512.8 ESI-MS(M+1) by the method of Example 13. ($^1$H NMR, $CD_3OD$) δ: 1.9 (m, 2H), 2.9-3.3 (m, 8H), 3.5-4.0 (m, 4H), 4.4-5.0 (m, 2H), 7.2-7.9 (m, 10H). Competitive inhibition testing of the compound follow the methods of Example 7 yielded the following results (average of triplicates with actual mean values described):

Inhibition at 1 μM

| MC1-R | MC3-R | MC4-R | MC5-R |
|---|---|---|---|
| 28% | 11% | 55% | 23% |

EXAMPLE 19

A compound of the following structure:

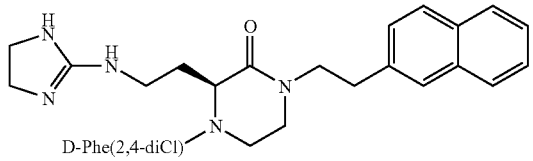

was synthesized by a method similar to that of Example 1. The molecular weight was determined to be 580.9 ESI-MS (M+1) by the method of Example 13. ($^1$H NMR, CD$_3$OD) δ: 1.75 (m, 2H), 2.9-3.3 (m, 8H), 3.4-4.1 (m, 8H), 4.4-5.0 (m, 2H), 7.2-7.9 (m, 10H). Competitive inhibitition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 24% | 14% | 68% | 27% |

EXAMPLE 20

A compound of the following structure:

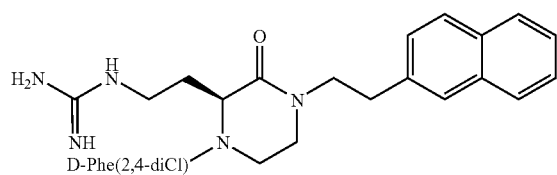

was synthesized by a method similar to that of Example 1. The molecular weight was determined to be 554.7 ESI-MS (M+1) by the method of Example 13. ($^1$H NMR, CD$_3$OD) δ: 1.9 (m, 2H), 2.9-3.3 (m, 8H), 3.4-4.1 (m, 4H), 4.3-5.0 (m, 2H), 7.2-7.9 (m, 10H). Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 21% | 13% | 81% | 24% |

EXAMPLE 21

A compound of the following structure:

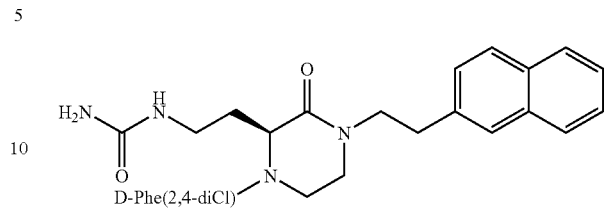

was synthesized by a method similar to that of Example 1. The molecular weight was determined to be 555.8 ESI-MS (M+1) by the method of Example 13. ($^1$H NMR, CD$_3$OD) δ: 1.8 (m, 2H), 2.9-3.3 (m, 8H), 3.4-4.05 (m, 4H), 4.4-5.0 (m, 2H), 7.1-7.9 (m, 10H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
| --- | --- | --- | --- |
| 11% | 0% | 9% | 5% |

EXAMPLE 22

A compound of the following structure:

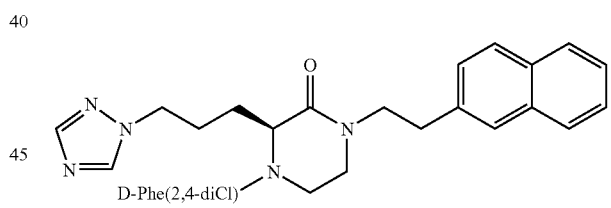

was synthesized by a method similar to that of Example 1. The molecular weight was determined to be 579.2 ESI-MS (M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
| --- | --- | --- | --- |
| 7% | 0% | 0% | 3% |

EXAMPLE 23

A compound of the following structure:

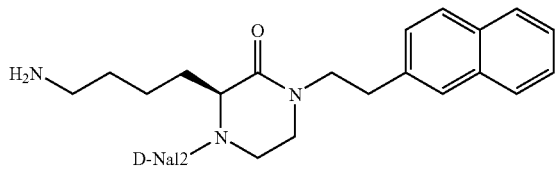

was synthesized by the method of Example 1. The molecular weight was determined to be 523.2 ESI-MS(M+1) by the method of Example 13. Competitive inhibition testing of the compound against following the methods of Example 7 yielded the following results (average of triplicates with actual mean values described):

Inhibition at 1 μM

| MC1-R | MC3-R | MC4-R | MC5-R |
| --- | --- | --- | --- |
| 26% | 14% | 72% | 30% |

EXAMPLE 24

A compound of the following structure:

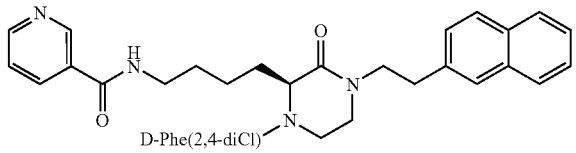

was by a method similar to that of Example 1. The molecular weight was determined to be 645.9 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 4% | 6% | 23% | 13% |

EXAMPLE 25

A compound of the following structure:

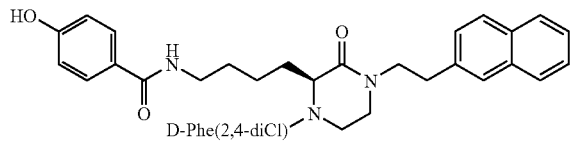

was synthesized by a method similar to that of Example 1. The molecular weight was determined to be 660.8 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 3% | 6% | 12% | 26% |

EXAMPLE 26

A compound of the following structure:

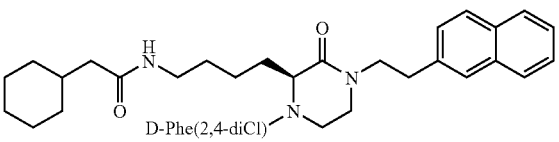

was synthesized by a method similar to that of Example 1. The molecular weight was determined to be 664.9 ESI-MS (M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
| --- | --- | --- | --- |
| 0% | 4% | 6% | 2% |

EXAMPLE 27

A compound of the following structure:

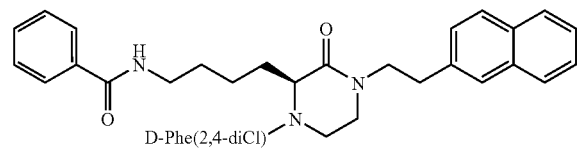

was synthesized by a method similar to that of Example 1. The molecular weight was determined to be 664.9 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 3% | 6% | 14% | 16% |

EXAMPLE 28

A compound of the following structure:

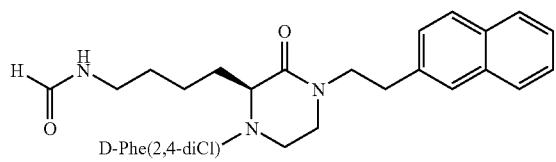

was synthesized by a method similar to that of Example 1. The molecular weight was determined to be 568.9 ESI-MS (M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 8% | 0% | 30% | 6% |

EXAMPLE 29

A compound of the following structure:

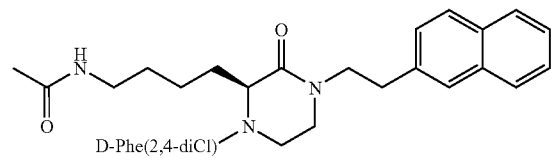

was synthesized by a method similar to that of Example 1. The molecular weight was determined to be 582.9 ESI-MS (M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 17% | 3% | 26% | 0% |

EXAMPLE 30

A compound of the following structure:

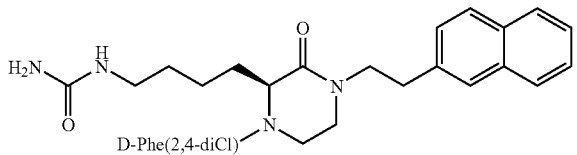

was synthesized by a method similar to that of Example 1. The molecular weight was determined to be 583.9 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 43% | 15% | 49% | 14% |

EXAMPLE 31

A compound of the following structure:

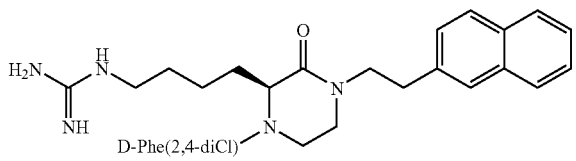

was synthesized by a method similar to that of Example 1. The molecular weight was determined to be 582.9 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 66% | 68% | 96% | 42% |

EXAMPLE 32

A compound of the following structure:

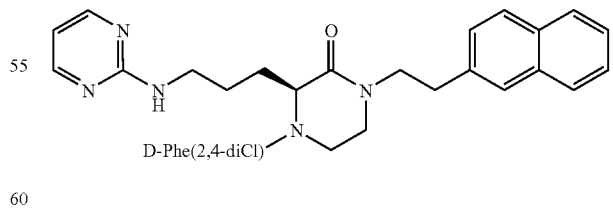

was synthesized by a method similar to that of Example 1. The molecular weight was determined to be 605.8 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 3%    | 9%    | 12%   | 19%   |

EXAMPLE 33

A compound of the following structure:

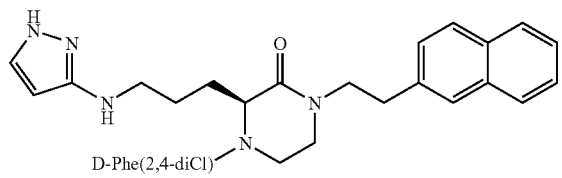

was synthesized by a method similar to that of Example 1. The molecular weight was determined to be 593.1 ESI-MS (M+1) by the method of Example 13. ($^1$H NMR, CD$_3$OD) δ: 1.7 (m, 2H), 2.9-3.3 (m, 8H), 3.4-4.1 (m, 4H), 4.4-5.0 (m, 2H), 7.2-7.9 (m, 12H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 20%   | 8%    | 3%    | 12%   |

EXAMPLE 34

A compound of the following structure:

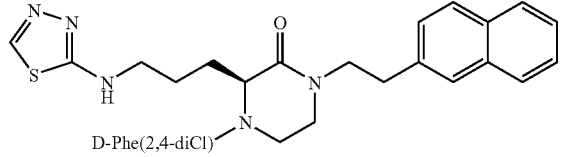

was synthesized by a method similar to that of Example 1. The molecular weight was determined to be 611.0 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 28%   | 31%   | 70%   | 32%   |

EXAMPLE 35

A compound of the following structure:

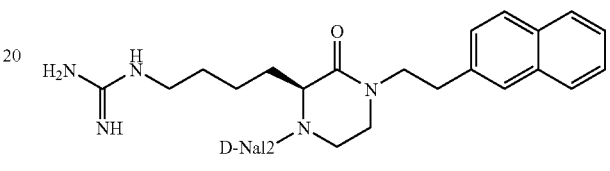

was synthesized by a method similar to that of Example 1. The molecular weight was determined to be 565.3 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 60%   | 73%   | 97%   | 57%   |

EXAMPLE 36

A compound of the following structure:

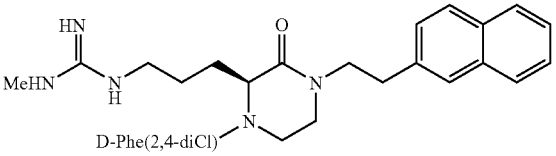

was synthesized by a method similar to that of Example 1. The molecular weight was determined to be 582.6 ESI-MS (M+1) by the method of Example 13. ($^1$H NMR, CD$_3$OD) δ: 1.1-1.8 (m, 4H), 2.85 (s, 1H), 2.9-3.3 (m, 8H), 3.35-4.1 (m, 4H), 4.4-5.0 (m, 2H), 7.1-7.9 (m, 10H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 19% | 43% | 93% | 27% |

EXAMPLE 37

A compound of the following structure:

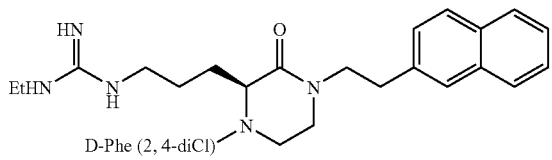

was synthesized by a method similar to that of Example 1. The molecular weight was determined to be 596.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 14% | 35% | 91% | 24% |

EXAMPLE 38

A compound of the following structure:

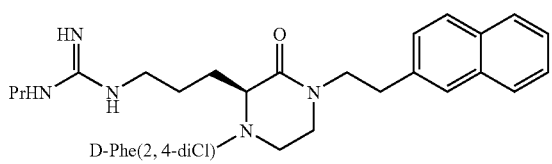

was synthesized by a method similar to that of Example 1. The molecular weight was determined to be 610.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 13% | 34% | 88% | 26% |

EXAMPLE 39

A compound of the following structure:

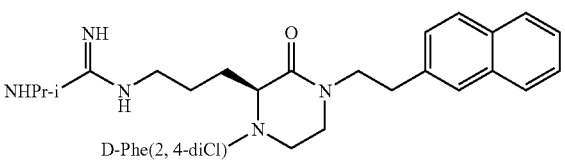

was synthesized by a method similar to that of Example 1. The molecular weight was determined to be 610.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 37% | 40% | 85% | 28% |

EXAMPLE 40

A compound of the following structure:

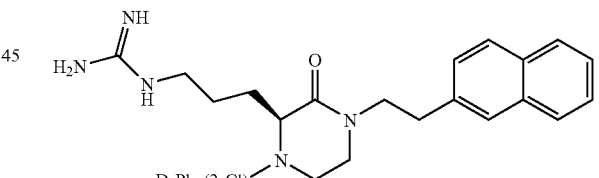

was synthesized by the general method of Example 6. The molecular weight was determined to be 534.4 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 3% | 2% | 69% | 5% |

EXAMPLE 41

A compound of the following structure:

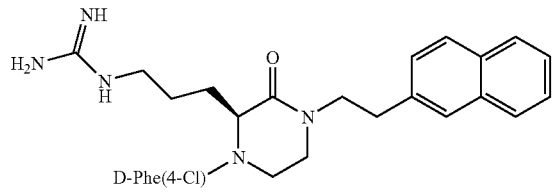

was synthesized by a method similar to that of Example 1. The molecular weight was determined to be 534.5 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 34% | 38% | 87% | 29% |

The Ki was determined by the method of Example 8, with the following results:

Ki (nM)

| MC1-R | MC3-R | MC4-R | MC5-R |
|---|---|---|---|
| 214 | 892 | 79 | 1448 |

In a cAMP assay as in Example 9 for determination of agonist/antagonist status, it was determined that the compound was an agonist as to MC1-R, MC3-R, MC4-R, and MC5-R.

EXAMPLE 42

A compound of the following structure:

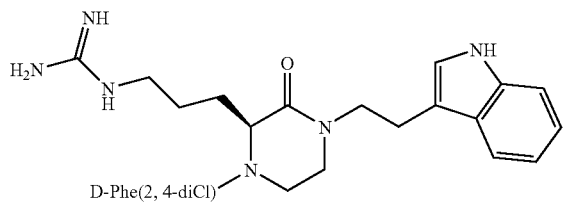

was synthesized by a method similar to that of Example 1. The molecular weight was determined to be 557.5 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 7% | 57% | 96% | 35% |

EXAMPLE 43

A compound of the following structure:

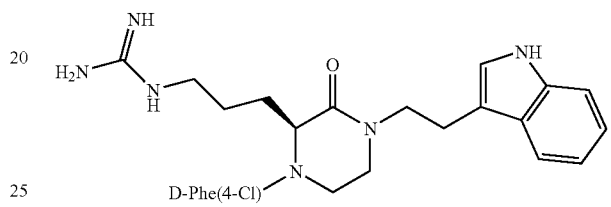

was synthesized by a method similar to that of Example 1. The molecular weight was determined to be 523.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 10% | 28% | 68% | 43% |

EXAMPLE 44

A compound of the following structure:

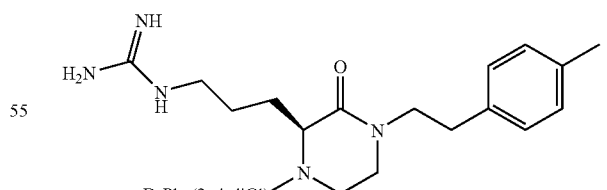

was synthesized by a method similar to that of Example 1. The molecular weight was determined to be 532.4 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 11%   | 42%   | 78%   | 34%   |

EXAMPLE 45

A compound of the following structure:

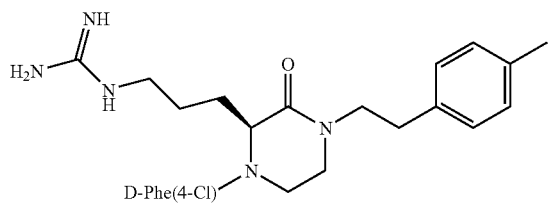

was synthesized by a method similar to that of Example 1. The molecular weight was determined to be 498.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 9%    | 9%    | 49%   | 17%   |

EXAMPLE 46

A compound of the following structure:

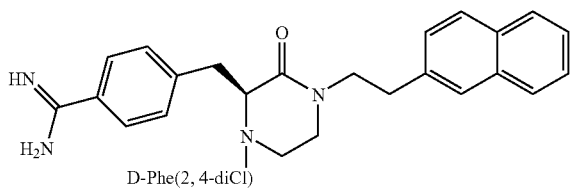

was synthesized by a method similar to that of Example 1. The molecular weight was determined to be 601.5 ESI-MS (M+1) by the method of Example 13. Competitive inhibition testing of the compound 5 following the methods of Example 7 yielded the following results (average of triplicates with actual mean values described; experimental results less than 0% reported as 0%):

Inhibition at 1 μM

| MC1-R | MC3-R | MC4-R | MC5-R |
|-------|-------|-------|-------|
| 5%    | 0%    | 31%   | 21%   |

EXAMPLE 47

A compound of the following structure:

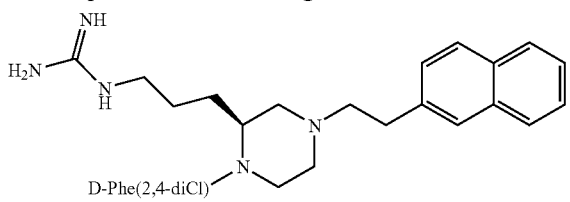

was synthesized by the general method of Example 6. The molecular weight was determined to be 512.0 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 6%    | 87%   | 99%   | 75%   |

The Ki was determined by the method of Example 8, with the following results:

Ki (nM)

| MC1-R | MC3-R | MC4-R | MC5-R |
|-------|-------|-------|-------|
| 1198  | 97    | 3     | 259   |

In a cAMP assay as in Example 9 for determination of agonist/antagonist status, it was determined that the compound was an agonist as to MC4-R.

In PE studies of male rats as in Example 10, IV administration at dose levels of 0.1 to 100 μg/Kg produced no observed effect above baseline.

EXAMPLE 48

A compound of the following structure:

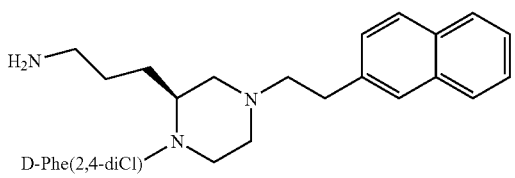

was synthesized by the general method of Example 6. The molecular weight was determined to be 554.1 ESI-MS(M+1) by the method of Example 13. Competitive inhibition testing of the compound against α-MSH—NDP following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 33% | 81% | 39% |

EXAMPLE 49

A compound of the following structure:

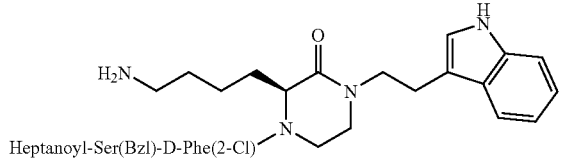

Heptanoyl-Ser(Bzl)-D-Phe(2-Cl)

was synthesized by the method of Example 3. The molecular weight was determined to be 785.0 ESI-MS(M+1) by the method of Example 13. ($^1$H NMR, CD$_3$OD) δ: 0.8-1.9 (m, 17H), 2.25 (m, 2H), 2.75-3.25 (m, 8H), 3.35-4.05 (m, 6H), 4.55 (m, 3H), 4.9 (m, 1H), 5.3 (m, 1H), 6.9-7.6 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 96% | 51% | 99% | 82% |

EXAMPLE 50

A compound of the following structure:

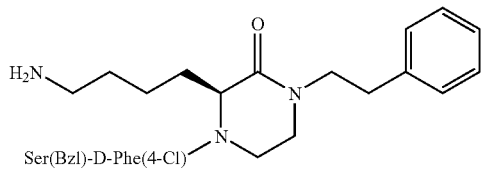

Ser(Bzl)-D-Phe(4-Cl)

was synthesized by the method of Example 3. The molecular weight was determined to be 634.5 ESI-MS(M+1) by the method of Example 13. ($^1$H NMR, CD$_3$OD) δ: 1.2 (m, 2H), 1.55-1.75 (m, 4H), 2.75-3.25 (m, 8H), 3.5 (m, 1H), 3.65 (m, 1H), 3.55-4.15 (m, 5H), 4.55 (m, 2H), 4.75 (m, 1H), 5.15 (m, 1H), 7.15-7.45 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 46% | 39% | 40% | 14% |

EXAMPLE 51

A compound of the following structure:

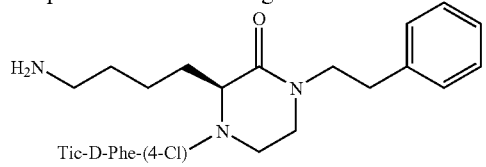

Tic-D-Phe-(4-Cl)

was synthesized by the method of Example 3. The molecular weight was determined to be 616.3 ESI-MS(M+1) by the method of Example 13. ($^1$H NMR, CD$_3$OD) δ: 1.2 (m, 2H), 1.55-1.85 (m, 4H), 2.8-3.25 (m,10H), 3.55-4.25 (m, 5H), 4.4 (m, 2H), 4.8 (m,1H), 5.2 (m, 1H), 7.15-7.45 (m, 13H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 68% | 21% | 66% | 16% |

EXAMPLE 52

A compound of the following structure:

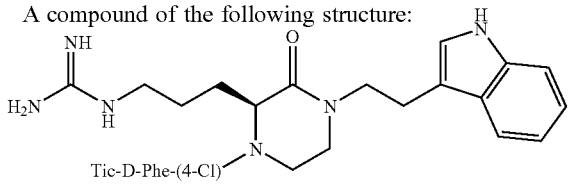

Tic-D-Phe-(4-Cl)

was synthesized by a method similar to that of Example 3. The molecular weight was determined to be 683.6 ESI-MS (M+1) by the method of Example 13. ($^1$H NMR, d$_6$-DMSO) δ: 1.4 (m, 2H), 1.65 (m, 1H), 1.85 (m, 1H), 2.8-3.5 (m, 10H), 3.7 (m, 2H), 4.05-4.4 (m, 5H), 4.75 (m, 1H), 5.15 (m, 1H), 7.15-7.45 (m, 13H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 96% | 88% | 99% | 89% |

The Ki was determined by the method of Example 8, with the following results:

Ki (nM)

| MC1-R | MC3-R | MC4-R | MC5-R |
|---|---|---|---|
| 3 | 77 | 2 | 52 |

EXAMPLE 53

A compound of the following structure:

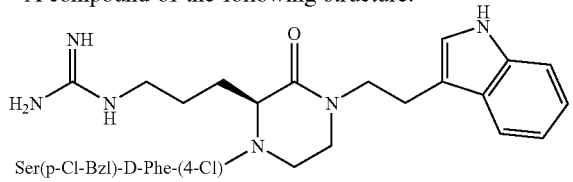

Ser(p-Cl-Bzl)-D-Phe-(4-Cl)

was synthesized by a method similar to that of Example 3. The molecular weight was determined to be 735.6 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 81% | 64% | 94% | 90% |

EXAMPLE 54

A compound of the following structure:

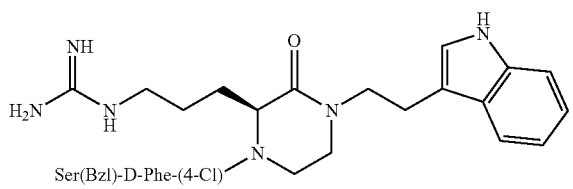

Ser(Bzl)-D-Phe-(4-Cl)

was synthesized by a method similar to that of Example 3. The molecular weight was determined to be 701.8 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 86% | 55% | 96% | 81% |

EXAMPLE 55

A compound of the following structure:

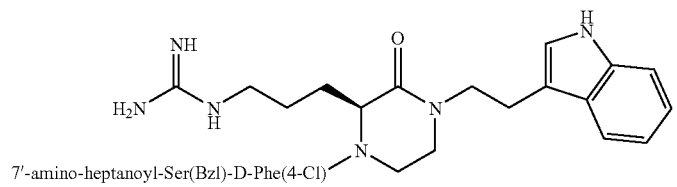

7'-amino-heptanoyl-Ser(Bzl)-D-Phe(4-Cl)

was synthesized by a method similar to that of Example 3. The molecular weight was determined to be 829.0 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
| --- | --- | --- | --- |
| 96% | 97% | 99% | 94% |

The Ki was determined by the method of Example 8, with the following results:

Ki (nM)

| MC1-R | MC3-R | MC4-R | MC5-R |
| --- | --- | --- | --- |
| 4 | 17 | 2 | 32 |

EXAMPLE 56

A compound of the following structure:

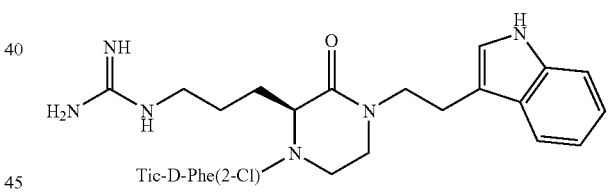

Tic-D-Phe(2-Cl)

was synthesized by a method similar to that of Example 3. The molecular weight was determined to be 684.1 ESI-MS (M+1) by the method of Example 13. ($^1$H NMR, CD$_3$OD) δ: 1.4-1.9 (m, 4H), 2.7-3.3 (m, 10H), 3.45 (m, 1H), 3.55 (m, 1H), 3.8-4.2 (m, 3H), 4.4 (m, 2H), 4.8-5.45 (m, 2H), 6.9-7.6 (m, 13H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 95%   | 50%   | 99%   | 62%   |

EXAMPLE 57

A compound of the following structure:

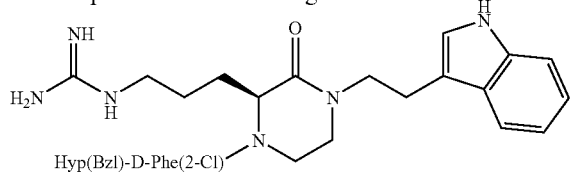

Hyp(Bzl)-D-Phe(2-Cl)

was synthesized by a method similar to that of Example 3. The molecular weight was determined to be 728.3 ESI-MS (M+1) by the method of Example 13. ($^1$H NMR, CD$_3$OD) δ: 1.4-1.9 (m, 4H), 2.6 (m, 2H), 2.95-3.25 (m, 10H), 3.4-3.55 (m, 4H), 3.7-4.2 (m, 2H), 4.3-4.45 (m, 2H), 4.8-5.45 (m, 2H), 6.9-7.6 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 91%   | 59%   | 99%   | 85%   |

EXAMPLE 58

A compound of the following structure:

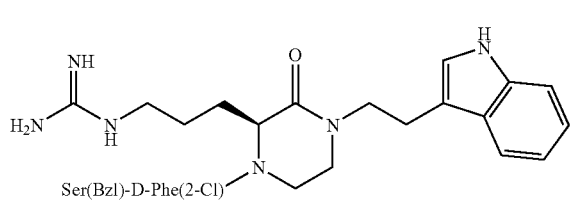

Ser(Bzl)-D-Phe(2-Cl)

was synthesized by a method similar to that of Example 3. The molecular weight was determined to be 702.2 ESI-MS (M+1) by the method of Example 13. ($^1$H NMR, CD$_3$OD) δ: 1.4-1.9 (m, 4H), 2.85-3.25 (m, 8H), 3.35-3.7 (m, 4H), 3.75-4.15 (m, 3H), 4.5 (m, 2H), 4.8-5.35 (m, 2H), 6.9-7.6 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 87%   | 40%   | 98%   | 71%   |

EXAMPLE 59

A compound of the following structure:

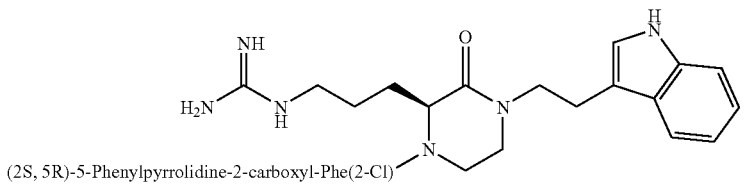

(2S, 5R)-5-Phenylpyrrolidine-2-carboxyl-Phe(2-Cl)

was synthesized by a method similar to that of Example 3. The molecular weight was determined to be 698.1 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 62%   | 22%   | 83%   | 19%   |

EXAMPLE 60

A compound of the following structure:

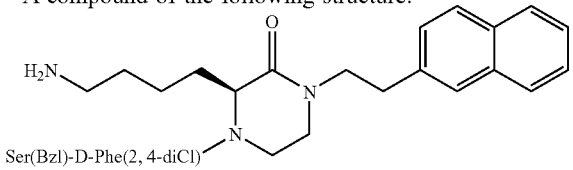

Ser(Bzl)-D-Phe(2, 4-diCl)

was synthesized by the method of Example 1. The molecular weight was determined to be 718.5 ESI-MS(M+1) by the method of Example 13. ($^1$H NMR, CD$_3$OD) δ: 1.0-1.9 (m, 6H), 2.5-3.3 (m, 8H), 3.53-3.8 (m, 4H), 4.1 (m, 3H), 4.5 (m, 2H), 4.7-5.3 (m, 2H), 7.0-7.9 (m, 15H). Competitive inhibition testing of the compound following the methods of Example 7 yielded the following results (average of triplicates with actual mean values described):

EXAMPLE 61

A compound of the following structure:

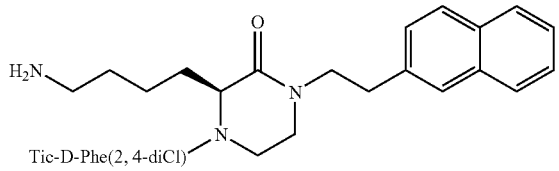

Tic-D-Phe(2, 4-diCl)

was synthesized by the method of Example 1. The molecular weight was determined to be 700.3 ESI-MS(M+1) by the method of Example 13. ($^1$H NMR, CD$_3$OD) δ: 1.0-1.9 (m, 6H), 2.6-3.3 (m, 10H), 3.4-4.7 (m, 5H), 4.4 (m, 2H), 4.7-5.4 (m, 2H), 7.0-7.9 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 63%   | 62%   | 100%  | 80%   |

In a cAMP assay as in Example 9 for determination of agonist/antagonist status, it was determined that the compound was an agonist as to MC1-R, MC4-R and MC5-R.

EXAMPLE 62

A compound of the following structure:

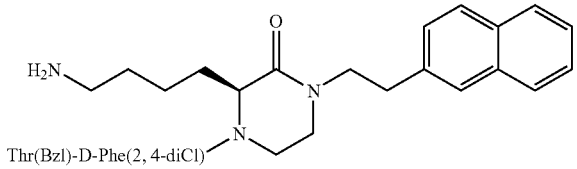

Thr(Bzl)-D-Phe(2, 4-diCl)

was synthesized by the method of Example 1. The molecular weight was determined to be 732.4 ESI-MS (M+1) by the method of Example 13. ($^1$H NMR, CD$_3$OD) δ: 1.0-1.9 (m, 9H), 2.5-3.25 (m, 8H), 3.4-3.9 (m, 4H), 4.05 (m, 1H), 4.15 (m, 1H), 4.25 (m, 1H), 4.5 (m, 1H), 4.7-5.3 (m, 2H), 7.0-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 30%   | 34%   | 99%   | 78%   |

In a cAMP assay as in Example 9 for determination of agonist/antagonist status, it was determined that the compound was an agonist as to MC1-R, MC4-R and MC5-R.

EXAMPLE 63

A compound of the following structure:

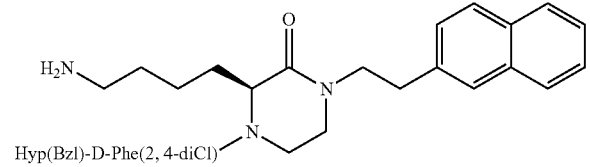

Hyp(Bzl)-D-Phe(2, 4-diCl)

was synthesized by the method of Example 1. The molecular weight was determined to be 744.5 ESI-MS (M+1) by the method of Example 13. ($^1$H NMR, CD$_3$OD) δ: 1.0-1.9 (m, 6H), 2.55-3.3 (m, 10H), 3.4-4.15 (m, 7H), 4.4 (m, 2H), 4.6 (m, 2H), 4.7-5.4 (m, 2H), 7.1-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 21%   | 61%   | 100%  | 83%   |

In a cAMP assay as in Example 9 for determination of agonist/antagonist status, it was determined that the compound was an agonist as to MC1-R, MC4-R and MC5-R.

EXAMPLE 64

A compound of the following structure:

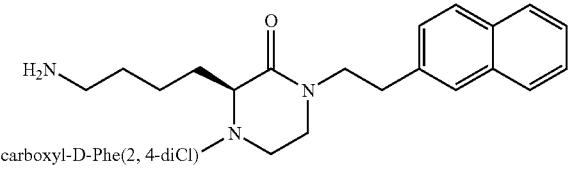

(2S, 5R)-5-Phenylpyrrolidine-2-carboxyl-D-Phe(2, 4-diCl)

was synthesized by the method of Example 1. The molecular weight was determined to be 714.5 ESI-MS (M+1) by the method of Example 13. ($^1$H NMR, CD$_3$OD) δ: 1.0-1.9 (m, 6H), 2.1-3.25 m, 10H), 3.4-4.15 (m, 4H), 4.4 (m, 1H), 4.65 (m, 1H), 4.7-5.3 (m, 2H), 7.1-7.9 (m, 15H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 18% | 92% | 51% |

In a cAMP assay as in Example 9 for determination of agonist/antagonist status, it was determined that the compound was an agonist as to MC1-R, MC4-R and MC5-R. The Ki was determined by the method of Example 8, with the following results:

Ki (nM)

| MC1-R | MC3-R | MC4-R | MC5-R |
|---|---|---|---|
| >1 μM | 855 | 50 | 789 |

In ICV feeding studies as in Example 11 at 1 nmol dose levels, a 24 hour change in food intake of −7.77 g, and change in weight of −5.88 g, was observed.

In PE studies of male rats as in Example 10, IV administration at dose levels of 0.001 to 100 μg/Kg produced no observed effect above baseline, and ICV administration at 0.1 to 10 nmol also produced no observed effect above baseline.

EXAMPLE 65

A compound of the following structure:

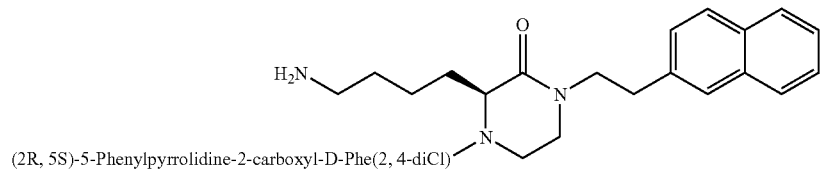

(2R, 5S)-5-Phenylpyrrolidine-2-carboxyl-D-Phe(2, 4-diCl)

was synthesized by the method of Example 1. The molecular weight was determined to be 714.5 ESI-MS(M+1) by the method of Example 13. ($^1$H NMR, CD$_3$OD) δ: 1.0-1.9 (m, 6H), 2.1-3.3 (m, 10H), 3.45-4.1 (m, 4H), 4.45 (m, 1H), 4.7 (m, 1H), 4.75-5.3 (m, 2H), 7.1-7.9 (m, 15H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 9% | 71% | 46% |

In a cAMP assay as in Example 9 for determination of agonist/antagonist status, it was determined that the compound was an agonist as to MC1-R, MC4-R and MC5-R.

EXAMPLE 66

A compound of the following structure:

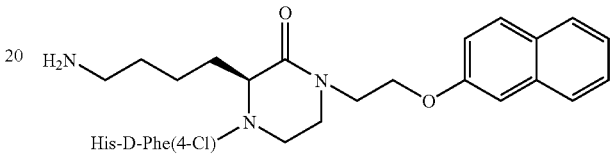

His-D-Phe(4-Cl)

was synthesized by the method of Example 2. The molecular weight was determined to be 660.6 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 97% | 26% | 56% | 21% |

EXAMPLE 67

A compound of the following structure:

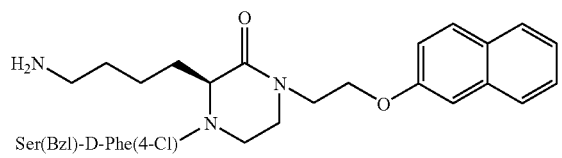

Ser(Bzl)-D-Phe(4-Cl)

was synthesized by the method of Example 2. The molecular weight was determined to be 700.4 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 64%   | 21%   | 64%   | 72%   |

EXAMPLE 68

A compound of the following structure:

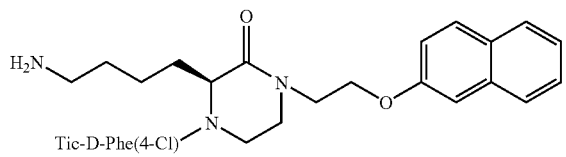

was synthesized by the method of Example 2. The molecular weight was determined to be 682.5 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 88%   | 35%   | 88%   | 65%   |

EXAMPLE 69

A compound of the following structure:

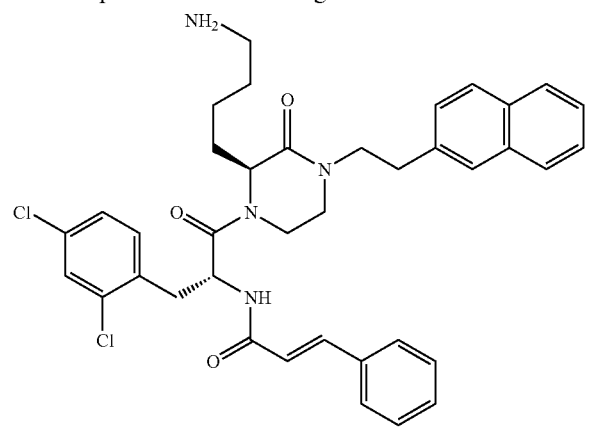

was synthesized by the method of Example 1. The molecular weight was determined to be 671.2 ESI-MS (M+1) by the method of Example 13. ($^1$H NMR, CD$_3$OD) δ: 1.0-1.9 (m, 6H), 2.7-3.25 (m, 8H), 3.45-4.15 (m, 4H), 4.35-5.3 (m, 2H), 6.55-6.75 (m, 2H), 7.1-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 30%   | 46%   | 96%   | 60%   |

In a cAMP assay as in Example 9 for determination of agonist/antagonist status, it was determined that the compound was an antagonist as to MC1-R and MC4-R and an agonist as to MC5-R.

The Ki was determined by the method of Example 8, with the following results:

Ki (nM)

| MC1-R | MC3-R | MC4-R | MC5-R |
|-------|-------|-------|-------|
| 502   | 648   | 6     | 398   |

In ICV feeding studies as in Example 11 at 1 nmol dose levels, a 24 hour change in food intake of −10.1 g, and change in weight of −9.91 g, was observed. In PE studies of male rats as in Example 10, IV administration at a dose level of 1 μg/Kg produced no observed effect above baseline.

EXAMPLE 70

A compound of the following structure:

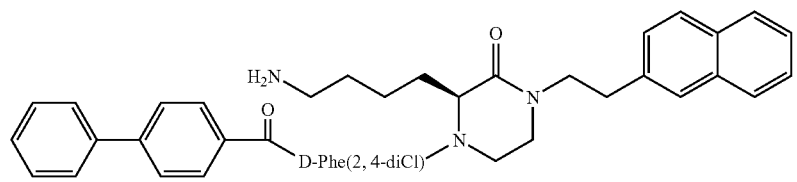

was synthesized by the method of Example 1. The molecular weight was determined to be 735.3 ESI-MS(M+1) by the method of Example 13. ($^1$H NMR, CD$_3$OD) δ: 1.0-1.9 (m, 6H), 2.6-3.25 (m, 8H), 3.4-4.15 (m, 4H), 4.35-5.3 (m, 2H), 7.1-7.9 (m, 19H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|-------|-------|-------|-------|
| 0%    | 4%    | 72%   | 54%   |

EXAMPLE 71

A compound of the following structure:

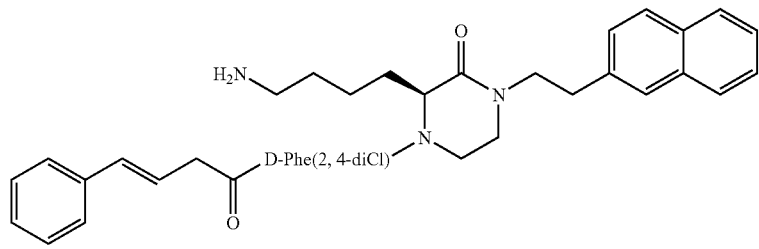

was synthesized by the method of Example 1. The molecular weight was determined to be 685.2 ESI-MS (M+1) by the method of Example 13. ($^1$H NMR, CD$_3$OD) δ: 1.0-1.9 (m, 6H), 2.6-3.25 (m, 10H), 3.4-4.1 (m, 4H), 4.35-5.3 (m, 2H), 6.15 (m, 1H), 6.45 (m, 1H), 7.1-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 14%   | 25%   | 91%   | 61%   |

In a cAMP assay as in Example 9 for determination of agonist/antagonist status, it was determined that the compound was an antagonist as to MC1-R and MC4-R and an agonist as to MC5-R.

EXAMPLE 72

A compound of the following structure:

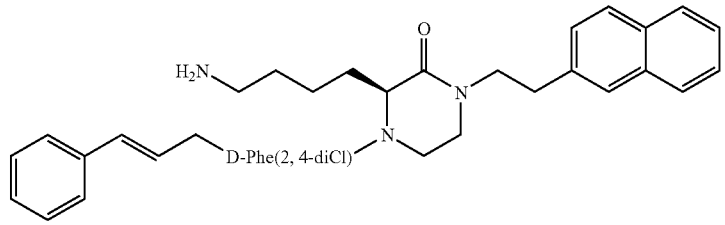

was synthesized by the method of Example 1. The molecular weight was determined to be 657.1 ESI-MS(M+1) by the method of Example 13. ($^1$H NMR, CD$_3$OD) δ: 0.85-1.7 (m, 6H), 2.6-3.3 (m, 10H), 3.4-4.1 (m, 4H), 4.4-4.8 (m, 2H), 6.15 (m, 1H), 6.8 (m, 1H), 7.2-7.9 (m, 15H). Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 7%    | 34%   | 92%   | 30%   |

In a cAMP assay as in Example 9 for determination of agonist/antagonist status, it was determined that the compound was an agonist as to MC1-R, MC4-R and MC5-R.

EXAMPLE 73

A compound of the following structure:

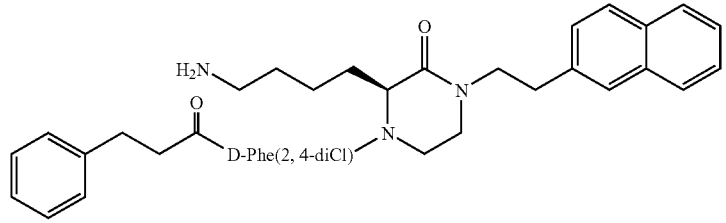

was synthesized by the method of Example 1. The molecular weight was determined to be 673.2 ESI-MS(M+1) by the method of Example 13. Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 72%   | 22%   | 92%   | 34%   |

In a cAMP assay as in Example 9 for determination of agonist/antagonist status, it was determined that the compound was an agonist as to MC1-R and MC5-R and antagonist as to MC4-R.

EXAMPLE 74

A compound of the following structure:

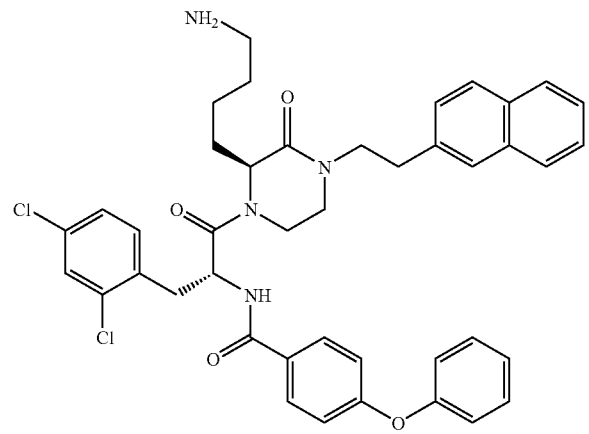

was synthesized by the method of Example 1. The molecular weight was determined to be 737.2 ESI-MS(M+1) by the method of Example 13. ($^1$H NMR, CD$_3$OD) δ: 1.0-2.0 (m, 6H), 2.7-3.3 (m, 8H), 3.4-4.15 (m, 4H), 4.4-5.3 (m, 2H), 7.0-8.0 (m, 19H). Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 35%   | 51%   | 99%   | 51%   |

In a cAMP assay as in Example 9 for determination of agonist/antagonist status, it was determined that the compound was an antagonist as to MC1-R and MC4-R and an agonist as to MC5-R.

The Ki was determined by the method of Example 8, with the following results:

Ki (nM)

| MC1-R | MC3-R | MC4-R | MC5-R |
|-------|-------|-------|-------|
| 915   | 149   | 1     | 282   |

In ICV feeding studies as in Example 11 at 1 nmol dose levels, a 24 hour change in food intake of −0.6 g, and change in weight of −1.73 g, was observed. In PE studies of male rats as in Example 10, IV administration at dose levels of 1 µg/Kg and 50 µg/Kg produced no observed effect above baseline.

EXAMPLE 75

A compound of the following structure:

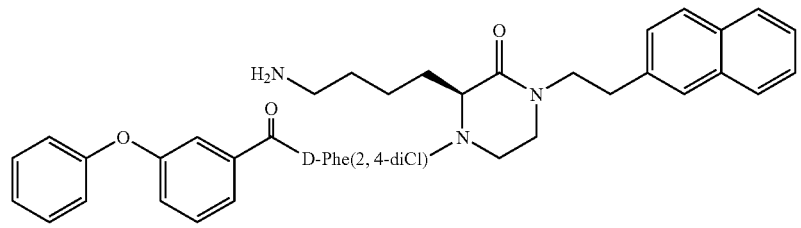

was synthesized by the method of Example 1. The molecular weight was determined to be 737.2 ESI-MS(M+1) by the method of Example 13. ($^1$H NMR, CD$_3$OD) δ: 1.0-2.0 (m, 6H), 2.7-3.3 (m, 8H), 3.4-4.15 (m, 4H), 4.4-5.3 (m, 2H), 7.0-8.0 (m, 19H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 3% | 21% | 97% | 61% |

In a cAMP assay as in Example 9 for determination of agonist/antagonist status, it was determined that the compound was an antagonist as to MC1-R and MC4-R and an agonist as to MC5-R.

EXAMPLE 76

A compound of the following structure:

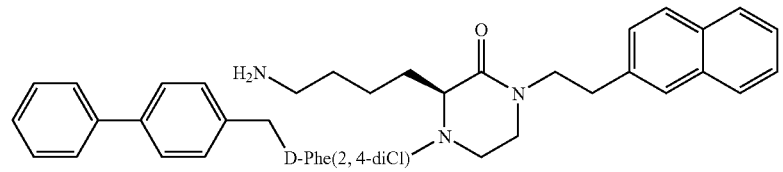

was synthesized by a method similar to that of Example 1. The molecular weight was determined to be 707.1 ESI-MS (M+1) by the method of Example 13. ($^1$H NMR, CD$_3$OD) δ: 0.9-1.7 (m, 6H), 2.6-3.3 (m, 8H), 3.4-4.1 (m, 4H), 4.4-5.1 (m, 4H), 7.2-7.9 (m, 19H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 4% | 85% | 9% |

In a cAMP assay as in Example 9 for determination of agonist/antagonist status, it was determined that the compound was an antagonist as to MC1-R and MC4-R and an agonist as to MC5-R.

EXAMPLE 77

A compound of the following structure:

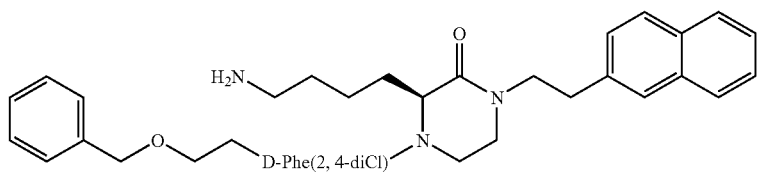

was synthesized by a method similar to that of Example 1. The molecular weight was determined to be 675.3 ESI-MS (M+1) by the method of Example 13. Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 27%   | 17%   | 91%   | 30%   |

In a cAMP assay as in Example 9 for determination of agonist/antagonist status, it was determined that the compound was an antagonist as to MC1-R and MC4-R and an agonist as to MC5-R.

EXAMPLE 78

A compound of the following structure:

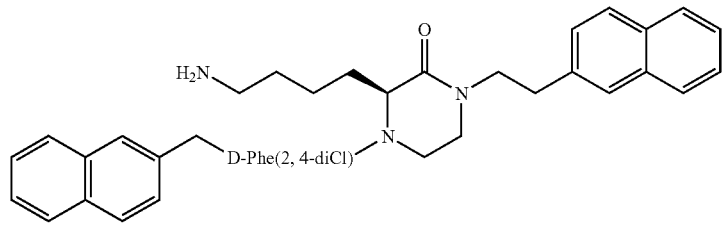

was synthesized by a method similar to that of Example 1. The molecular weight was determined to be 681.2 ESI-MS (M+1) by the method of Example 13. ($^1$H NMR, CD$_3$OD) δ: 0.9-1.7 (m, 6H), 2.6-3.3 (m, 8H), 3.4-4.1 (m, 4H), 4.4-5.1 (m, 4H), 7.2-8.0 (m, 19H). Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 4%    | 4%    | 84%   | 2%    |

In a cAMP assay as in Example 9 for determination of agonist/antagonist status, it was determined that the compound was an antagonist as to MC1-R and MC4-R and an agonist as to MC5-R.

EXAMPLE 79

A compound of the following structure:

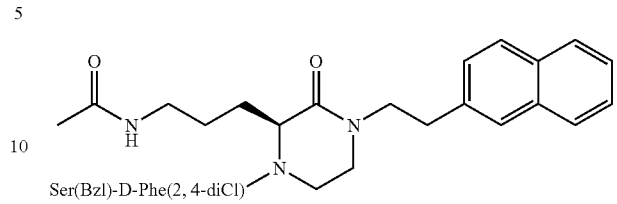

was synthesized by a method similar to that of Example 1. The molecular weight was determined to be 746.4 ESI-MS (M+1) by the method of Example 13. ($^1$H NMR, CD$_3$OD) δ: 1.25-1.85 (m, 4H), 1.95 (d, 3H), 2.5-3.25 (m, 8H), 3.3-4.1 (m, 7H), 4.35-5.3 (m, 4H), 7.1-7.9 (m, 15H). Competitive inhibition testing of the compound following the methods of Example 7 yielded the following results (average of triplicates with actual mean values described):

Inhibition at 1 µM

| MC1-R | MC3-R | MC4-R | MC5-R |
|-------|-------|-------|-------|
| 13%   | 10%   | 61%   | 30%   |

EXAMPLE 80

A compound of the following structure:

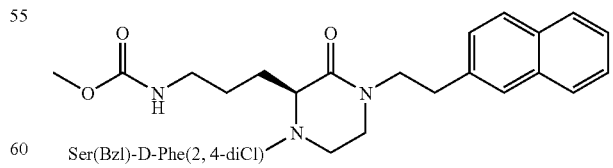

was synthesized by a method similar to that of Example 1. The molecular weight was determined to be 762.3 ESI-MS (M+1) by the method of Example 13. ($^1$H NMR, CD$_3$OD) δ: 1.25-1.85 (m, 4H), 2.5-3.25 (m, 8H), 3.3-4.1 (m, 10H), 4.35-5.3 (m, 4H), 7.1-7.9 (m, 15H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|-------|-------|-------|-------|
| 1%    | 0%    | 43%   | 20%   |

EXAMPLE 81

A compound of the following structure:

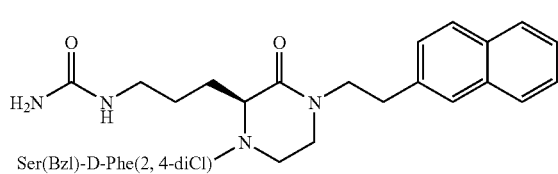

Ser(Bzl)-D-Phe(2, 4-diCl)

was synthesized by a method similar to that of Example 1. The molecular weight was determined to be 747.3 ESI-MS (M+1) by the method of Example 13. ($^1$H NMR, CD$_3$OD) δ: 1.25-1.85 (m, 4H), 2.5-3.25 (m, 8H), 3.3-4.1 (m, 7H), 4.35-5.3 (m, 4H), 7.1-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 8%    | 43%   | 94%   | 66%   |

In a cAMP assay as in Example 9 for determination of agonist/antagonist status, it was determined that the compound was an agonist as to MC1-R, MC4-R and MC5-R.

EXAMPLE 82

A compound of the following structure:

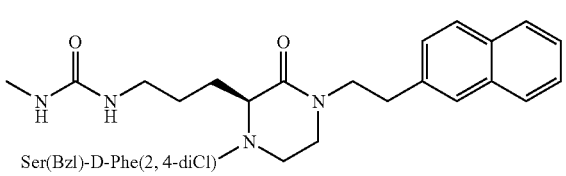

Ser(Bzl)-D-Phe(2, 4-diCl)

was synthesized by a method similar to that of Example 1. The molecular weight was determined to be 761.4 ESI-MS (M+1) by the method of Example 13. ($^1$H NMR, CD$_3$OD) δ: 1.25-1.85 (m, 4H), 2.5-3.25 (m, 11H), 3.3-4.1 (m, 6H), 4.35-5.3 (m, 4H), 7.1-7.9 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 5%    | 11%   | 72%   | 31%   |

EXAMPLE 83

A compound of the following structure:

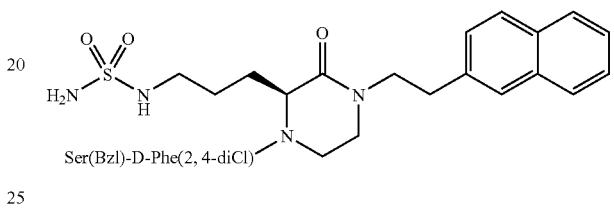

Ser(Bzl)-D-Phe(2, 4-diCl)

was synthesized by a method similar to that of Example 1. The molecular weight was determined to be 783.2 ESI-MS (M+1) by the method of Example 13. ($^1$H NMR, CD$_3$OD) δ: 1.25-1.85 (m, 4H), 2.5-3.25 (m, 8H), 3.3-4.1 (m, 6H), 4.35-5.3 (m, 4H), 7.1-7.9 (m, 15H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|-------|-------|-------|-------|
| 0%    | 12%   | 60%   | 25%   |

EXAMPLE 84

A compound of the following structure:

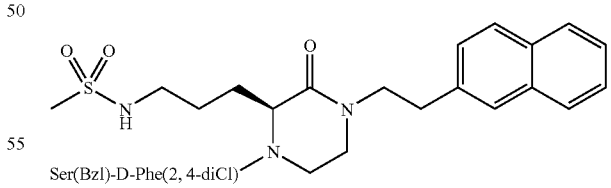

Ser(Bzl)-D-Phe(2, 4-diCl)

was synthesized by a method similar to that of Example 1. The molecular weight was determined to be 782.3 ESI-MS (M+1) by the method of Example 13. ($^1$H NMR, CD$_3$OD) δ: 1.25-1.85 (m, 4H), 2.5-3.25 (m, 8H), 3.3-4.1 (m, 10H), 4.35-5.3 (m, 4H), 7.1-7.9 (m, 15H). Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|---|---|---|---|
| 0% | 9% | 40% | 14% |

EXAMPLE 85

A compound of the following structure:

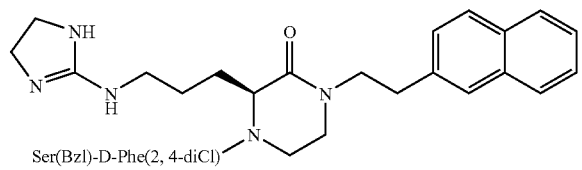

was synthesized by a method similar to that of Example 1. The molecular weight was determined to be 772.4 ESI-MS (M+1) by the method of Example 13. ($^1$H NMR, CD$_3$OD) δ: 1.0-1.8 (m, 6H), 2.4-3.3 (m, 12H), 3.4-4.1 (m, 4H), 4.3-5.3 (m, 2H), 7.1-8.0 (m, 15H). Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 63% | 60% | 99% | 75% |

In a cAMP assay as in Example 9 for determination of agonist/antagonist status, it was determined that the compound was an agonist as to MC1-R, MC4-R and MC5-R. The Ki was determined by the method of Example 8, with the following results:

Ki (nM)

| MC1-R | MC3-R | MC4-R | MC5-R |
|---|---|---|---|
| 216 | 219 | 4 | 104 |

EXAMPLE 86

A compound of the following structure:

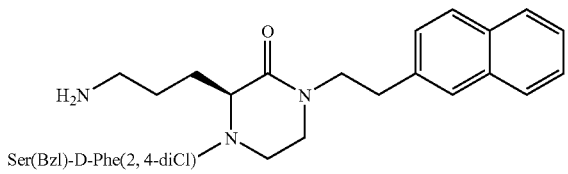

was synthesized by the method of Example 1. The molecular weight was determined to be 704.1 ESI-MS(M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 36% | 25% | 94% | 63% |

In a cAMP assay as in Example 9 for determination of agonist/antagonist status, it was determined that the compound was an agonist as to MC1-R, MC4-R and MC5-R.

EXAMPLE 87

A compound of the following structure:

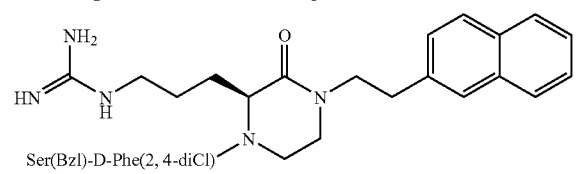

was synthesized by a method similar to that of Example 1. The molecular weight was determined to be 746.1 ESI-MS (M+1) by the method of Example 13. Competitive inhibition testing of the compound following the methods of Example 7 yielded the following results (average of triplicates with actual mean values described):

Inhibition at 1 μM

| MC1-R | MC3-R | MC4-R | MC5-R |
|---|---|---|---|
| 81% | 93% | 99% | 96% |

In a cAMP assay as in Example 9 for determination of agonist/antagonist status, it was determined that the compound was an agonist as to MC1-R, MC4-R and MC5-R.

EXAMPLE 88

A compound of the following structure:

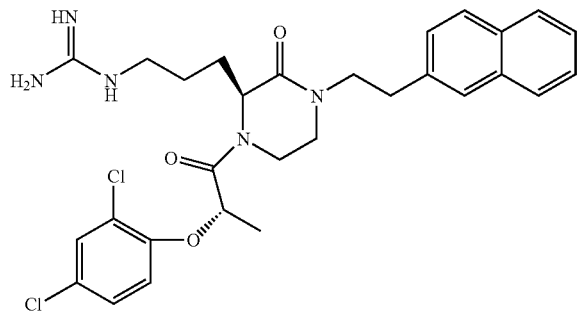

was synthesized by a method similar to that of Example 1. The molecular weight was determined to be 569.5 ESI-MS (M+1) by the method of Example 13. Competitive inhibition testing of the compound following the methods of Example 7 yielded the following results (average of triplicates with actual mean values described):

89

Inhibition at 1 μM

| MC1-R | MC3-R | MC4-R | MC5-R |
|-------|-------|-------|-------|
| 38%   | 24%   | 41%   | 21%   |

EXAMPLE 89

A compound of the following structure:

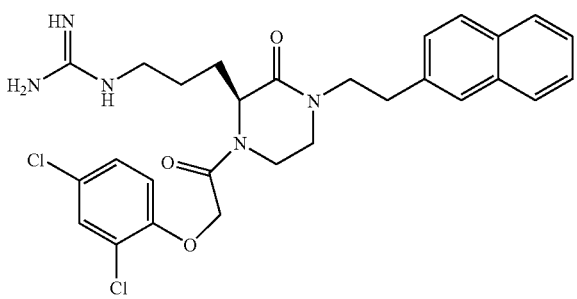

was synthesized by a method similar to that of Example 1. The molecular weight was determined to be 555.6 ESI-MS (M+1) by the method of Example 13. Competitive inhibition testing of the compound following the methods of Example 7 yielded the following results (average of triplicates with actual mean values described; experimental results less than 0% reported as 0%):

Inhibition at 1 μM

| MC1-R | MC3-R | MC4-R | MC5-R |
|-------|-------|-------|-------|
| 15%   | 0%    | 24%   | 20%   |

90

EXAMPLE 90

A compound of the following structure:

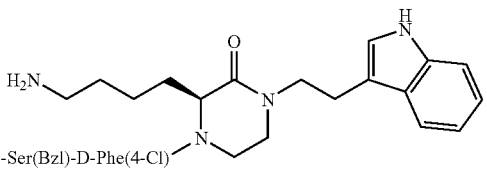

was synthesized by the method of Example 3. The molecular weight was determined to be 785.3 ESI-MS (M+1) by the method of Example 13. ($^1$H NMR, CD$_3$OD) δ: 0.8-1.9 (m, 17H), 2.25 (m, 2H), 2.75-3.25 (m, 8H), 3.35-4.05 (m, 6H), 4.55 (m, 3H), 4.9 (m, 1H), 5.3 (m, 1H), 6.9-7.6 (m, 14H). Competitive inhibition testing of the compound following the methods of Example 7 yielded the following results (average of triplicates with actual mean values described):

Inhibition at 1 μM

| MC1-R | MC3-R | MC4-R | MC5-R |
|-------|-------|-------|-------|
| 96%   | 72%   | 99%   | 99%   |

EXAMPLE 91

Ketopiperazine Compounds

Ketopiperazine compounds were made as set forth in the Examples 1-3 on synthesis. Compounds 91-1 and 91-2 were made by the methods of Example 2, and compounds 91-3 to 91-24 were made according to the methods of Example 1. The molecular weight was determined for each compound by the method of Example 13, and competitive inhibition testing of the compounds following the methods of Example 7 yielded the results shown in Table 1 (average of triplicates with actual mean values described; experimental results less than 0% reported as 0%).

The compounds of this example have the following general formula, with variable assignments as given in Table 1:

TABLE 1

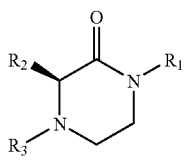

| No. | R$_1$ | R$_2$ | R$_3$ | % Inhibition at 1 μM at Melanocortin Receptor | | | | (M + 1) |
|-----|-------|-------|-------|---|---|---|---|---|
|     |       |       |       | 1 | 3 | 4 | 5 |  |
| 91-1 | (naphthyloxyethyl) | (guanidinobutyl) | (dichlorophenyl-aminomethyl ketone) | 54 | 42 | 91 | 54 | 585.7 |

TABLE 1-continued

| No. | R₁ | R₂ | R₃ | 1 | 3 | 4 | 5 | (M + 1) |
|---|---|---|---|---|---|---|---|---|
| 91-2 | 2-naphthyloxypropyl | guanidinobutyl | 2,4-dichlorobenzyl, NH-Cinnamoyl ketone | 21 | 66 | 99 | 81 | 715.5 |
| 91-3 | cyclohexylpropyl | guanidinobutyl | 2,4-dichlorobenzyl, NH₂ ketone | 18 | 7 | 39 | 22 | 525.6 |
| 91-4 | 3-methylphenylpropyl | guanidinobutyl | 2,4-dichlorobenzyl, NH₂ ketone | 7 | 4 | 64 | 0 | 533.4 |
| 91-5 | 3-methylphenylpropyl | guanidinobutyl | 4-chlorobenzyl, NH₂ ketone | 12 | 9 | 23 | 0 | 499.6 |
| 91-6 | 2-naphthylpropyl | guanidinobutyl | 2-naphthylmethyl, NH₂ ketone | 39 | 44 | 94 | 53 | 551.5 |
| 91-7 | 1-naphthylethyl | guanidinobutyl | 4-chlorobenzyl, NH₂ ketone | 8 | 15 | 12 | 11 | 521.5 |
| 91-8 | 2-naphthylethyl | guanidinobutyl | 4-chlorobenzyl, NH₂ ketone | 5 | 15 | 11 | 11 | 521.4 |
| 91-9 | 1-naphthylethyl | guanidinobutyl | 4-chlorobenzyl, NH₂ ketone | 15 | 17 | 45 | 36 | 535.4 |

TABLE 1-continued
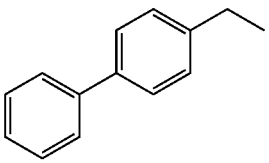
| No. | R₁ | R₂ | R₃ | % Inhibition at 1 μM at Melanocortin Receptor | | | | (M + 1) |
|---|---|---|---|---|---|---|---|---|
| | | | | 1 | 3 | 4 | 5 | |
| 91-10 | 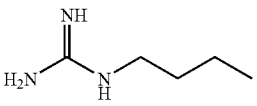 | 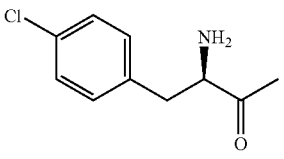 | 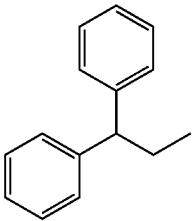 | 0 | 18 | 0 | 22 | 547.4 |
| 91-11 | 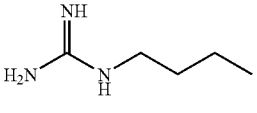 | 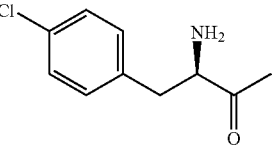 | 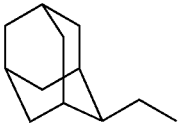 | 16 | 4 | 20 | 19 | 561.4 |
| 91-12 | 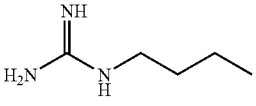 | 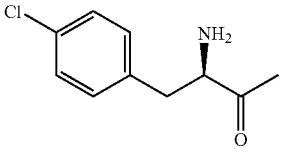 | 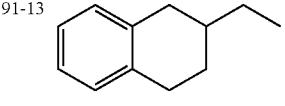 | 7 | 9 | 20 | 14 | 529.6 |
| 91-13 | 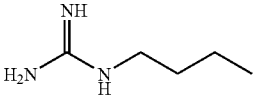 | 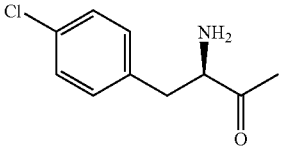 | 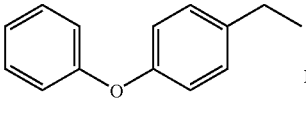 | 3 | 8 | 17 | 3 | 525.5 |
| 91-14 | 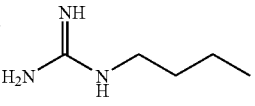 | 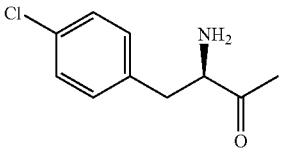 | 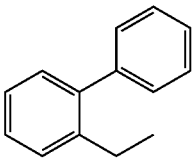 | 0 | 11 | 10 | 14 | 563.6 |
| 91-15 | 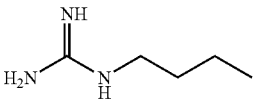 | 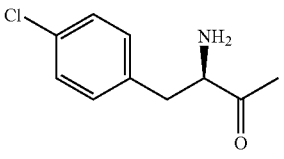 |  | 9 | 8 | 30 | 18 | 547.6 |

TABLE 1-continued
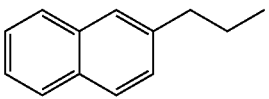
| No. | R₁ | R₂ | R₃ | % Inhibition at 1 μM at Melanocortin Receptor | | | | (M + 1) |
|---|---|---|---|---|---|---|---|---|
| | | | | 1 | 3 | 4 | 5 | |
| 91-16 | 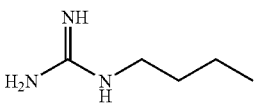 | 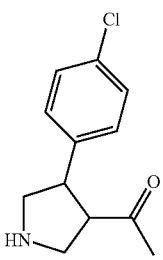 | 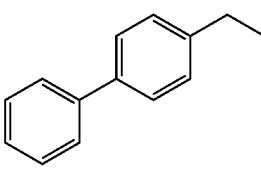 | 13 | 15 | 75 | 45 | 561.6 |
| 91-17 | 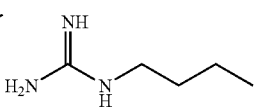 | 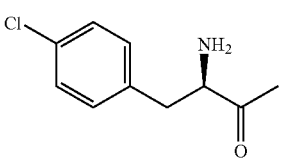 | 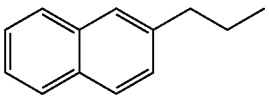 | 62 | 0 | 39 | 22 | 561.6 |
| 91-18 | 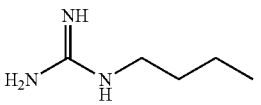 | 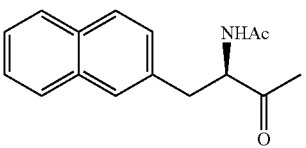 | 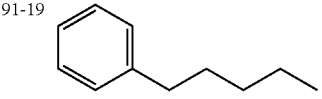 | 73 | 62 | 98 | 62 | 593.7 |
| 91-19 | 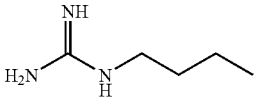 | 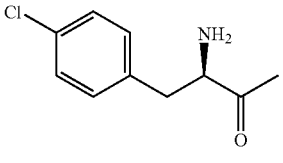 | 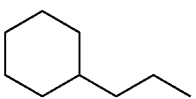 | 64 | 0 | 15 | 4 | 513.6 |
| 91-20 | 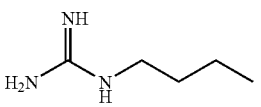 | 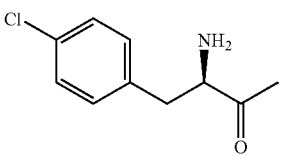 | 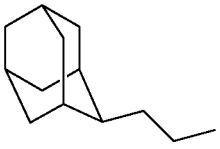 | 10 | 15 | 30 | 14 | 491.9 |
| 91-21 | 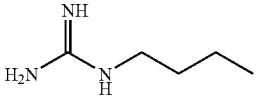 | 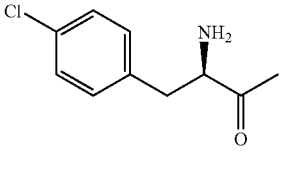 | 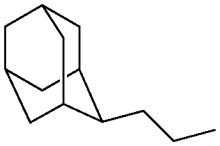 | 11 | 22 | 27 | 1 | 543.9 |
| 91-22 | 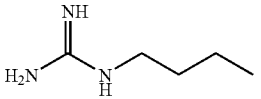 | 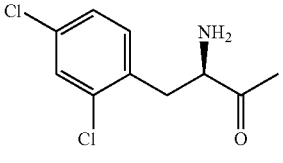 | | 0 | 18 | 35 | 26 | 577.5 |

TABLE 1-continued

| No. | R₁ | R₂ | R₃ | % Inhibition at 1 μM at Melanocortin Receptor | | | | (M + 1) |
|-----|----|----|----|---|---|---|---|---|
| | | | | 1 | 3 | 4 | 5 | |
| 91-23 | (norbornyl-propyl) | (guanidino-butyl) | (4-Cl-phenyl amino ketone) | 14 | 6 | 22 | 16 | 503.6 |
| 91-24 | (norbornyl-propyl) | (guanidino-butyl) | (2,4-diCl-phenyl amino ketone) | 7 | 8 | 42 | 44 | 537.4 |

Compound 91-2

In a cAMP assay as in Example 9 for determination of agonist/antagonist status, it was determined that compound 91-2 was inactive as to MC1-R, MC3-R, MC4-R and MC5-R.

The Ki was determined by the method of Example 8, with the following results:

Ki (nM)

| MC1-R | MC3-R | MC4-R | MC5-R |
|-------|-------|-------|-------|
| 375 | 293 | 7 | 135 |

Compound 91-6

In a cAMP assay as in Example 9 for determination of agonist/antagonist status, it was determined that compound 91-6 was an agonist as to MC1-R, MC4-R and MC5-R.

The Ki was determined by the method of Example 8, with the following results:

Ki (nM)

| MC1-R | MC3-R | MC4-R | MC5-R |
|-------|-------|-------|-------|
| 746 | 484 | 36 | 700 |

Compound 91-18

In a cAMP assay as in Example 9 for determination of agonist/antagonist status, it was determined that compound 91-18 was inactive as to MC1-R and MC4-R and is an agonist as to MC5-R. The Ki was determined by the method of Example 8, with the following results:

Ki (nM)

| MC1-R | MC3-R | MC4-R | MC5-R |
|-------|-------|-------|-------|
| 367 | 138 | 7 | 1107 |

EXAMPLE 92

Piperazine Compounds

Piperazine compounds were made as set forth in the Examples 4 and 5 on synthesis. Compounds 92-1, 92-2, and 92-9 to 92-17 were made the methods of Example 5, and compounds 92-3 to 92-8 were made by the methods of Example 4. The molecular weight was determined for each compound by the method of Example 13, and competitive inhibition testing of the compounds following the methods of Example 7 yielded the results shown in Table 2 (average of triplicates with actual mean values described; experimental results less than 0% reported as 0%).

The compounds of this example have the following general formula, with variable assignments as given in Table 2:

TABLE 2

| No. | R₁ | R₂ |
|---|---|---|
| 92-1 | benzyl ester (PhCH₂-O-C(=O)-CH₂-) | H₂N-C(=NH)-NH-butyl |
| 92-2 | H | H₂N-C(=NH)-NH-butyl |
| 92-3 | 2-naphthyl-CH₂-C(=O)- | H |
| 92-4 | 2-naphthyl-CH₂-C(=O)- | H |
| 92-5 | 2-naphthyl-CH₂-C(=O)- | H |
| 92-6 | 2-naphthyl-propyl | H |
| 92-7 | 2-naphthyl-propyl | H |
| 92-8 | 2-naphthyl-propyl | H |
| 92-9 | 1-naphthyl-NH-C(=O)-CH₂- | H₂N-C(=NH)-NH-butyl |
| 92-10 | 2-naphthyl-propyl | H₂N-butyl |
| 92-11 | 2-naphthyl-CH₂-C(=O)- | H₂N-butyl |

TABLE 2-continued
| No. | | | | | | | | |
|---|---|---|---|---|---|---|---|---|
| 92-12 | H | 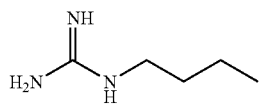 | | | | | | |
| 92-13 | H | 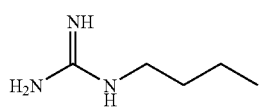 | | | | | | |
| 92-14 | H | 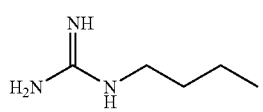 | | | | | | |
| 92-15 | H | 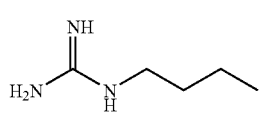 | | | | | | |
| 92-16 | 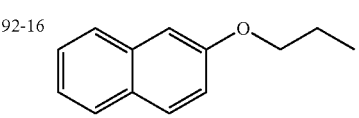 | 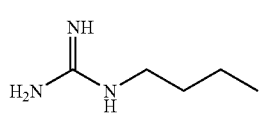 | | | | | | |
| 92-17 | 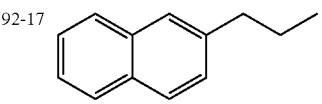 | 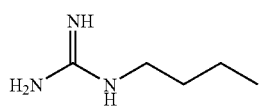 | | | | | | |
| | | % Inhibition at 1 μM at Melanocortin Receptor | | | | |
|---|---|---|---|---|---|---|
| No. | R₃ | 1 | 3 | 4 | 5 | (M + 1) |
| 92-1 | 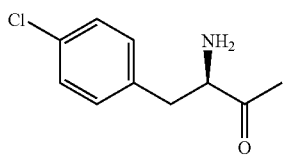 | 43 | 32 | 56 | 36 | 501.4 |
| 92-2 | 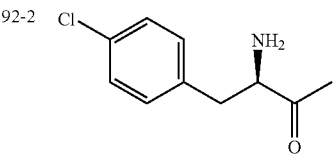 | 40 | 0 | 36 | 0 | 367.5 |
| 92-3 | 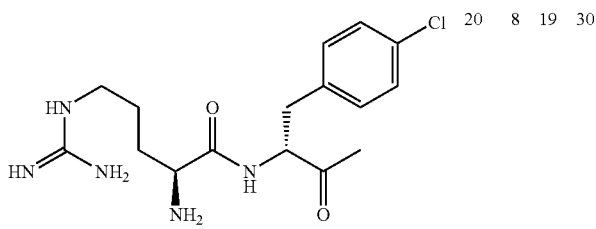 | 20 | 8 | 19 | 30 | 592.8 |

TABLE 2-continued

| ID | Structure | | | | | MW |
|---|---|---|---|---|---|---|
| 92-4 | [tetrahydroisoquinoline-C(O)NH-CH(CH2-C6H4-Cl)-C(O)CH3] | 0 | 0 | 23 | 22 | 595.7 |
| 92-5 | [BnO-CH2-CH(NH2)-C(O)NH-CH(CH2-C6H4-Cl)-C(O)CH3] | 0 | 0 | 10 | 20 | 613.7 |
| 92-6 | [Arg-NH-CH(CH2-C6H4-Cl)-C(O)CH3] | 4 | 16 | 8 | 14 | 578.8 |
| 92-7 | [tetrahydroisoquinoline-C(O)NH-CH(CH2-C6H4-Cl)-C(O)CH3] | 0 | 17 | 20 | 19 | 581.8 |
| 92-8 | [BnO-CH2-CH(NH2)-C(O)NH-CH(CH2-C6H4-Cl)-C(O)CH3] | 0 | 17 | 8 | 16 | 599.8 |
| 92-9 | [4-Cl-C6H4-CH2-CH(NH2)-C(O)CH3] | 59 | 5 | 43 | 1 | 564.7 |
| 92-10 | [4-Cl-C6H4-CH2-CH(NH2)-C(O)CH3] | 5 | 32 | 29 | 25 | 479.4 |

TABLE 2-continued

| ID | Structure | | | | | MW |
|---|---|---|---|---|---|---|
| 92-11 | (2,4-dichlorobenzyl aminomethyl ketone) | 13 | 0 | 26 | 11 | 527.7 |
| 92-12 | (tetrahydroisoquinoline carboxamide derivative) | 2 | 14 | 26 | 40 | 560.4 |
| 92-13 | (O-benzyl serine amide derivative) | 10 | 7 | 16 | 50 | 578.3 |
| 92-14 | (hexanoyl amide derivative) | 43 | 12 | 20 | 59 | 513.4 |
| 92-15 | (2,4-dichlorobenzyl aminomethyl ketone) | 34 | 2 | 12 | 7 | 401.2 |
| 92-16 | (2,4-dichlorobenzyl aminomethyl ketone) | 25 | 33 | 91 | 40 | 571.3 |
| 92-17 | (phenyl amino ketone) | 10 | 35 | 76 | 78 | 541.17 |

EXAMPLE 93

Ketopiperazine Compounds with Substituted $R_1$ Group

The compounds of Table 3 were synthesized by the method of Examples 1 to 3. The molecular weight was determined for each compound by the method of Example 13, and competitive inhibition testing of the compounds following the methods of Example 7 yielded the results shown in Table 3 (average of triplicates with actual mean values described; experimental results less than 0% reported as 0%).

The compounds have the following general structure, wherein $R_1$ is as defined in Table 3:

TABLE 3

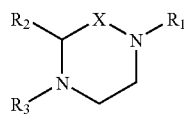

| $R_1$ | MC-1 | MC-3 | MC-4 | MC-5 |
|---|---|---|---|---|
| | % Inhibition at 1 μM | | | |
| Indole-3-ethyl | 10 | 28 | 68 | 43 |
| 2-(4-Methylphenyl)-ethyl | 9 | 9 | 49 | 17 |
| 2-(3-Methylphenyl)-ethyl | 12 | 9 | 23 | 0 |
| 1-Naphthylmethyl | 8 | 15 | 12 | 11 |
| 2-Naphthylmethyl | 5 | 15 | 11 | 11 |
| 1-Naphthylethyl | 15 | 17 | 45 | 36 |
| 4-Biphenylmethyl | 0 | 18 | 0 | 22 |
| 2,2-Diphenylethyl | 16 | 4 | 20 | 19 |
| 1-Adamantanemethyl | 7 | 9 | 20 | 14 |
| 1,2,3,4-Tetrahydro-naphthyl-2-methyl | 3 | 8 | 17 | 3 |
| 4-Phenoxy-benzyl | 0 | 11 | 10 | 14 |
| 2-Phenylbenzyl | 9 | 8 | 30 | 18 |
| 2-(4-Biphenyl)ethyl | 62 | 0 | 39 | 22 |
| 4-Phenylbutyl | 64 | −6 | 15 | 4 |
| Cyclohexylethyl | 10 | 15 | 30 | 14 |
| 1-Adamantaneethyl | 11 | 22 | 27 | 1 |
| 2-Norbornaneethyl | 14 | 6 | 22 | 16 |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound having the structure:

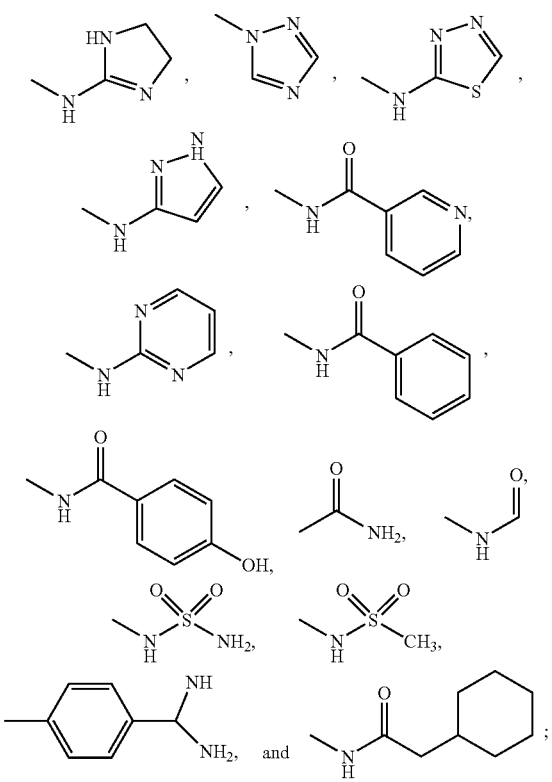

(I)

or a stereoisomer or pharmaceutically acceptable salt thereof,
wherein
$R_1$ is -$L_1$-J or, if X is $CH_2$, is H or -$L_1$-J;
$R_2$ is $(CH_2)_y$—W or, if X is $CH_2$, is H or -$L_1$-J, on the proviso that $R_1$ and $R_2$ are not both H;
$R_3$ is -$L_2$-Q;
$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance each ring in the ring structure consists of 5 or 6 ring atoms;

W is selected from the group consisting of $NH_2$, NH(C=NH)$NH_2$, —$NHCOCH_3$, —$CONHCH_3$, —NH(C=NH)NHMe, —NH(C=NH)NHEt, —NH(C=NH)NHPr, —NH(C=NH)NHPr—I, —NH(C=NH)$NH_2$, —NH(C=O)$OCH_3$, —NH(C=O)$CH_3$, —NH(C=O)$NH_2$, —NH(C=O)$NHCH_3$,

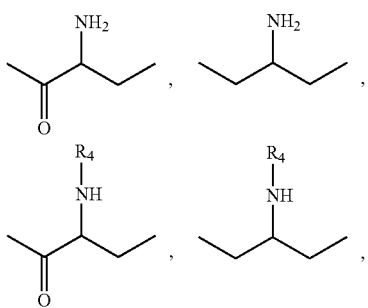

$L_2$ is a linker selected from the group consisting of

Q is an aromatic carbocyclic ring selected from the group consisting of phenyl, substituted phenyl, naphthyl and substituted naphthyl;

$R_4$ is H, —$R_5$ or —$R_5$—$R_6$;

$R_5$ is an amino acid residue or an amine capping group, provided that if $R_6$ is present, $R_5$ is an amino acid residue;

$R_6$ is H or an amine capping group;

X is $CH_2$ or C=O; and y is at each occurrence independently from 1 to 6.

2. The compound of claim 1 wherein J is a substituted or unsubstituted ring structure selected from the group consisting of

3. The compound of claim 1 wherein at least one ring of the group J is substituted with one or more halogen, alkyl or aryl groups.

4. The compound of claim 1 wherein $R_1$ is selected from the group consisting of

5. The compound of claim 1 wherein $R_1$ is selected from the group consisting of

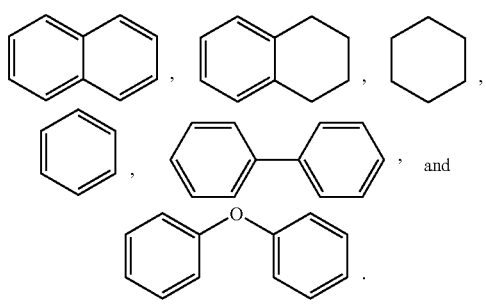

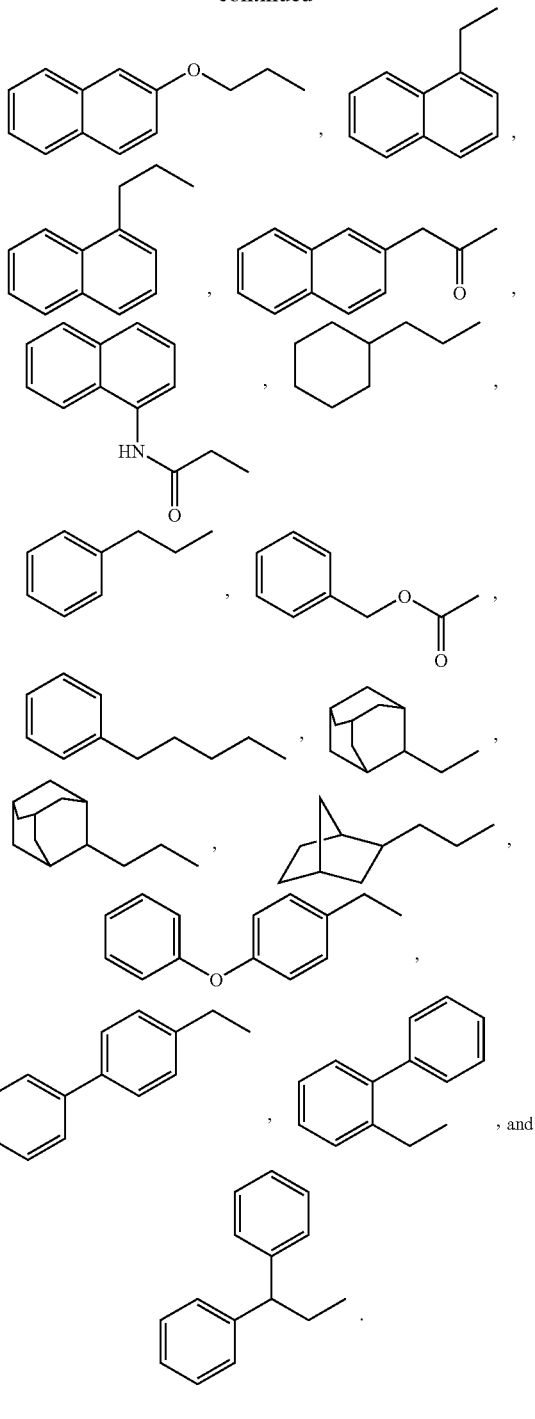

6. The compound of claim 1 wherein $R_2$ is selected from the group consisting of

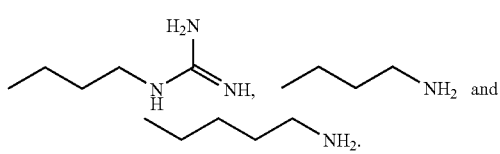

7. The compound of claim 1 where Q is

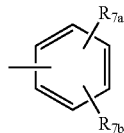

wherein $R_{7a}$ and $R_{7b}$ are optional ring substituents, and when one or both are present, are the same or different and independently hydroxyl, halogen, alkyl, or aryl groups attached directly or through an ether linkage.

8. The compound of claim 7 wherein the alkyl group is —$CH_3$ or —$OCH_3$.

9. The compound of claim 1 wherein $R_5$ or $R_6$ is an amine capping group selected from the group consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc and 8-Aoc.

10. The compound of claim 1 wherein $R_3$ is a D-amino acid with an aromatic carbocyclic ring selected from the group consisting of phenyl, substituted phenyl, naphthyl and substituted naphthyl.

11. The compound of claim 1 wherein $R_3$ is a D-amino acid with an amine capping group and an aromatic carbocyclic ring selected from the group consisting of phenyl, substituted phenyl, naphthyl and substituted naphthyl.

12. The compound of claim 1 wherein $R_3$ is a dipeptide consisting of a D-amino acid including an aromatic carbocyclic ring selected from the group consisting of phenyl, substituted phenyl, naphthyl and substituted naphthyl and a second amino acid residue, wherein the D-amino acid is bonded to the ring nitrogen.

13. The compound of claim 1 wherein $R_3$ is a dipeptide consisting of a D-amino acid including an aromatic carbocyclic ring selected from the group consisting of phenyl, substituted phenyl, naphthyl and substituted naphthyl and a second amino acid residue with an amine capping group.

14. The compound of claim 10, 11, 12 or 13 wherein the D-amino acid is selected from the group consisting of Phe, Phe(2-Cl), Phe(4-Cl), Phe(2,4-diCl), Phe(2,4-diF), Phe(3,4-diCl), Phe(4-N02), Phe(4-Me), Phe(4-Phenyl), HPhe, pF-Phe, Phe(4-Br), Phe(4-$CF_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4$CF_3$), and Phe(3,4di-OMe).

15. The compound of claim 10, 11, 12 or 13 wherein the D-amino acid is selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys(Z-2'Br), Lys(Bz), Thr(Bzl), Tic, Tiq, Cys(Bzl), Tyr(2,6-DiCl-Bzl) and Tyr(Bzl).

16. The compound of claim 12 or 13 wherein the second amino acid residue in the dipeptide is selected from the group of L-amino acids consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBZA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tie, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

17. The compound of claim 11 or 13 wherein the amine capping group is selected from the group consisting of hexyl, hexanoyl, heptanoyl, acetyl, phenylacetyl, cyclohexylacetyl, naphthylacetyl, cinnamoyl, benzyl, benzoyl, 7'-amino heptanoyl, 12-Ado, 6-Ahx, Amc, and 8-Aoc.

18. A compound having the structure:

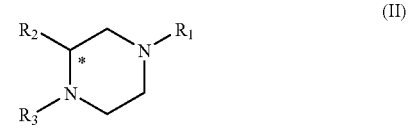

(II)

or a stereoisomer or pharmaceutically acceptable salt thereof,
wherein
$R_1$ is -$L_1$-J;
$R_2$ is $(CH_2)_y$—W;
$R_3$ is -$L_2$-Q;
$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;
J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance each ring in ring structure consists of 5 or 6 ring atoms;
W is selected from the group consisting of $NH_2$, NH(C=NH)$NH_2$, —NHCOC$H_3$, —CONHC$H_3$, —NH(C=NH)NHMe, —NH(C=NH)NHEt, —NH(C=NH)NHPr, —NH(C=NH)NHPr—I, —NH(C=NH)$NH_2$, —NH(C=O)OC$H_3$, —NH(C=O)C$H_3$, —NH(C=O)NHC$H_2$, —NH(C=O)NHC$H_3$,

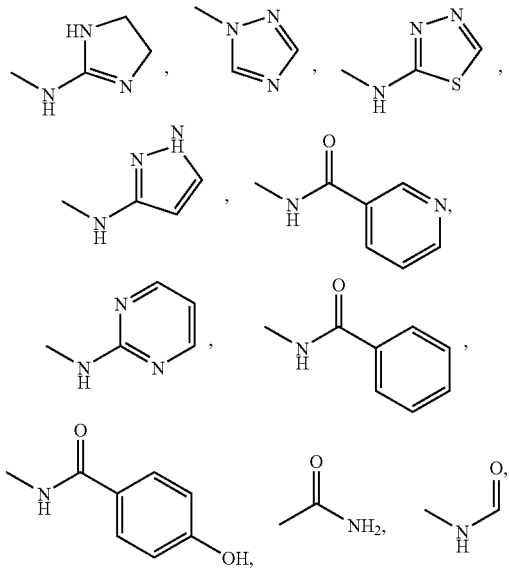

-continued

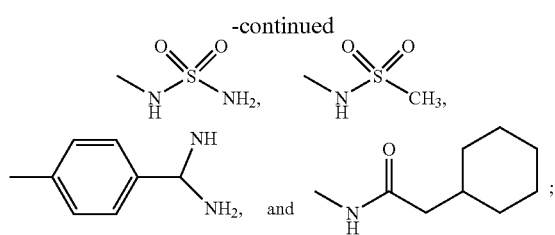

$L_2$ is a linker selected from the group consisting of

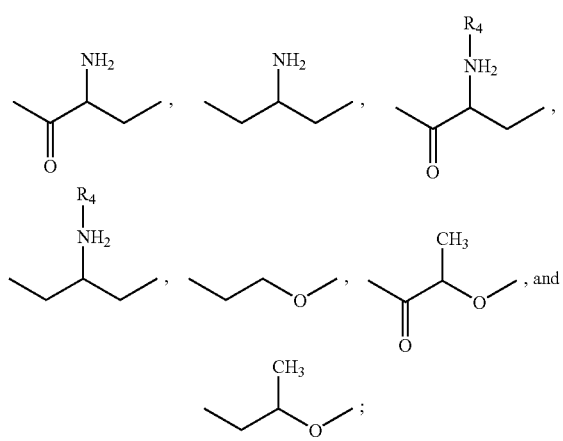

Q is an aromatic carbocyclic ring selected from the group consisting of phenyl, substituted phenyl, naphthyl and substituted naphthyl;

$R_4$ is H, $-R_5$ or $-R_5-R_6$;

$R_5$ is an amino acid residue or an amine capping group, provided that if $R_6$ is present, $R_5$ is an amino acid residue;

$R_6$ is H or an amine capping group; and y is at each occurrence independently from 1 to 6;

wherein the carbon atom marked with an asterisk can have any stereochemical configuration.

19. The compound of claim 18 wherein J is a substituted or unsubstituted ring structure selected from the group consisting of

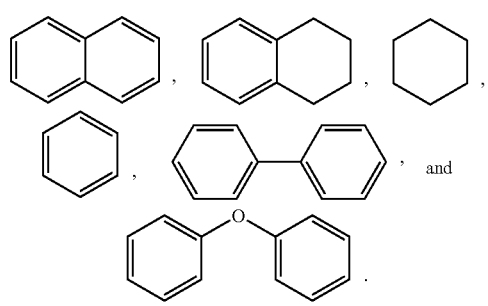

20. The compound of claim 18 wherein at least one ring of the group J is substituted with one or more halogen, alkyl or aryl groups.

21. The compound of claim 18 wherein $R_1$ is selected from the group consisting of

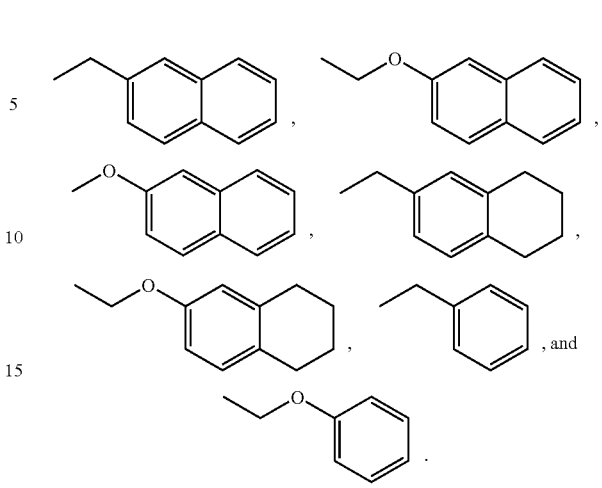

22. The compound of claim 18 wherein $R_1$ is selected from the group consisting of

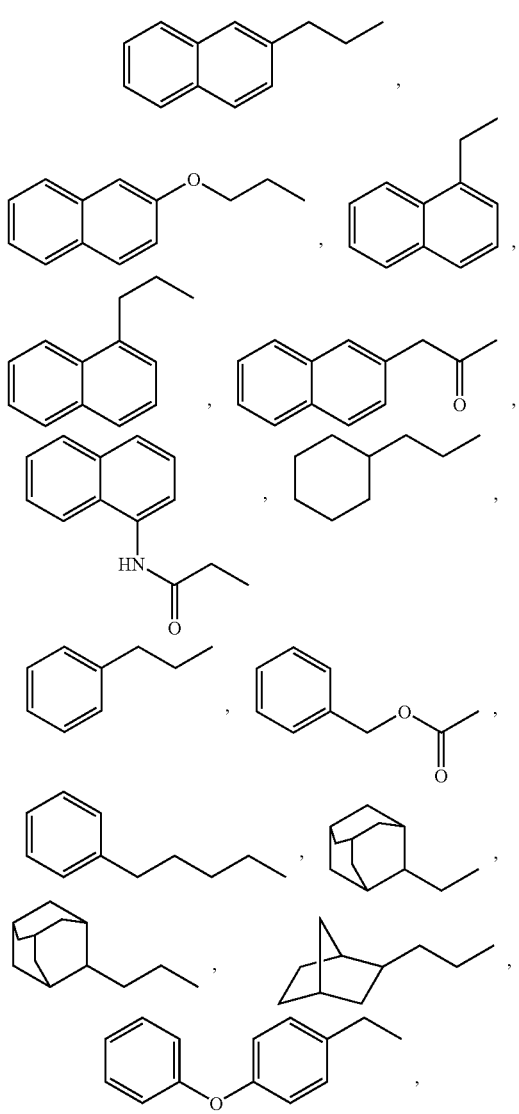

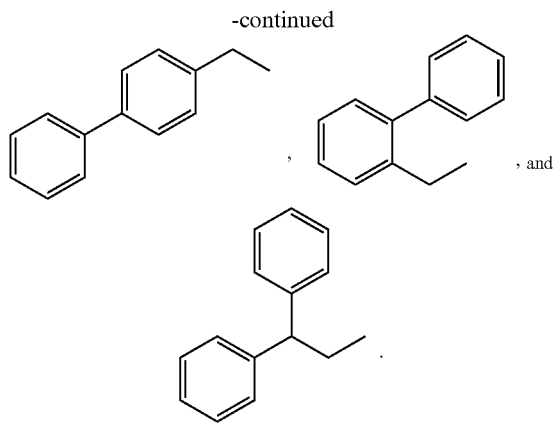, and

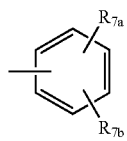

23. The compound of claim 18 wherein $R_2$ is selected from the group consisting of

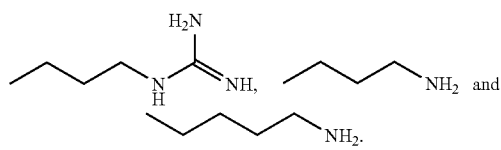

24. The compound of claim 18 where Q is

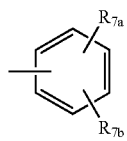

wherein $R_7a$ and $R_7b$ are optional ring substituents, and when one or both are present, are the same or different and independently hydroxyl, halogen, alkyl, or aryl groups attached directly or through an ether linkage.

25. The compound of claim 24 wherein the alkyl group is —$CH_3$ or —$OCH_3$.

26. The compound of claim 18 wherein $R_5$ or $R_6$ is an amine capping group selected from the group consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc and 8-Aoc.

27. The compound of claim 18 wherein $R_3$ is a D-amino acid with an aromatic carbocyclic ring selected from the group consisting of phenyl, substituted phenyl, naphthyl and substituted naphthyl.

28. The compound of claim 18 wherein $R_3$ is a D-amino acid with an amine capping group and an aromatic carbocyclic ring selected from the group consisting of phenyl, substituted phenyl, naphthyl and substituted naphthyl.

29. The compound of claim 18 wherein $R_3$ is a dipeptide consisting of a D-amino acid including an aromatic carbocyclic ring selected from the group consisting of phenyl, substituted phenyl, naphthyl and substituted naphthyl and a second amino acid residue, wherein the D-amino acid is bonded to the ring nitrogen.

30. The compound of claim 18 wherein $R_3$ is a dipeptide consisting of a D-amino acid including an aromatic carbocyclic ring selected from the group consisting of phenyl, substituted phenyl, naphthyl and substituted naphthyl and a second amino acid residue with an amine capping group.

31. The compound of claim 27, 28, 29 or 30 wherein the D-amino acid is selected from the group consisting of Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4Cl), Phe(2-F, 4Cl), Phe(2,4-diMe), Phe(2-Cl, 4-CF$_3$), and Phe(3,4di-OMe).

32. The compound of claim 27, 28, 29 or 30 wherein the D-amino acid is selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys(Z-2'Br), Lys(Bz), Thr(Bzl), Tic, Tiq, Cys(Bzl), Tyr(2,6-DiCl-Bzl) and Tyr(Bzl).

33. The compound of claim 29 or 30 wherein the second amino acid residue is selected from the group of L-amino acids consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBzA, B-Cpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer (Bzl), Ser(O-2-Naphthyl), Ser(O-Phenyl), Ser(O-4-Cl-Phenyl), Ser(O-2-Cl-Phenyl), Thr(Bzl), Tic, Beta-homoThr (Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

34. The compound of claim 28 or 30 wherein the amine capping group selected from the group consisting of hexyl, hexanoyl, heptanoyl, acetyl, phenylacetyl, cyclohexylacetyl, naphithylacetyl, cinnamoyl, benzyl, benzoyl, 7'-amino heptanoyl, 12-Ado, 6-Ahx, Amc, and 8-Aoc.

35. A compound having the structure:

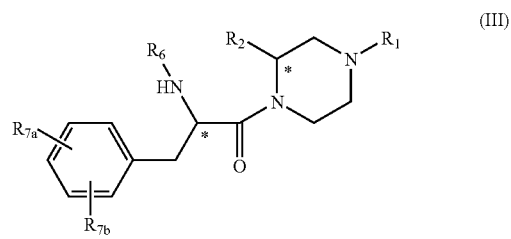

(III)

or a stereoisomer or pharmaceutically acceptable salt thereof,
wherein
R, is -$L_1$-J;
$R_2$ is $(CH_2)_y$—W;
$R_6$ is H or an amine capping group;
$R_{7a}$ and $R_{7b}$ are optional ring substituents, and when one or both are present, are the same or different and independently hydroxyl, halogen, alkyl, or aryl groups attached directly or through an ether linkage;
L, is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;
J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance each ring in the ring structure consists of 5 or 6 ring atoms;

W is selected from the group consisting of $NH_2$, $NH(C=NH)NH_2$, $-NHCOCH_3$, $-CONHCH_3$, $-NH(C=NH)NHMe$, $-NH(C=NH)NHEt$, $-NH(C=NH)NHPr$, $-NH(C=NH)NHPr-I$, $-NH(C=NH)NH_2$, $-NH(C=O)OCH_3$, $-NH(C=O)CH_3$, $-NH(C=O)NH_2$, $-NH(C=O)NHCH_3$,

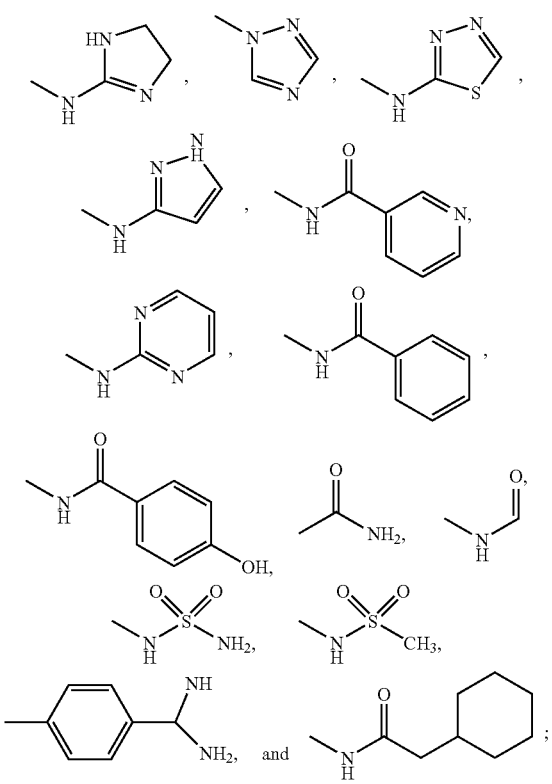

y is at each occurrence independently from 1 to 6;
wherein the carbon atoms marked with an asterisk can have any stereochemical configuration.

36. The compound of claim 35 wherein J is a substituted or unsubstituted ring structure selected from the group consisting of

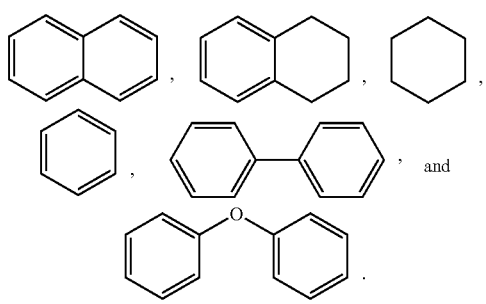

37. The compound of claim 35 wherein at least one ring of the group J is substituted with one or more halogen, alkyl or aryl groups.

38. The compound of claim 35 wherein $R_1$ is selected from the group consisting of

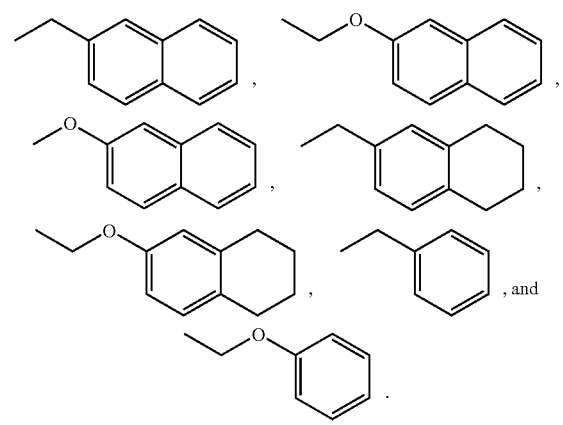

39. The compound of claim 35 wherein $R_1$ is selected from the group consisting of

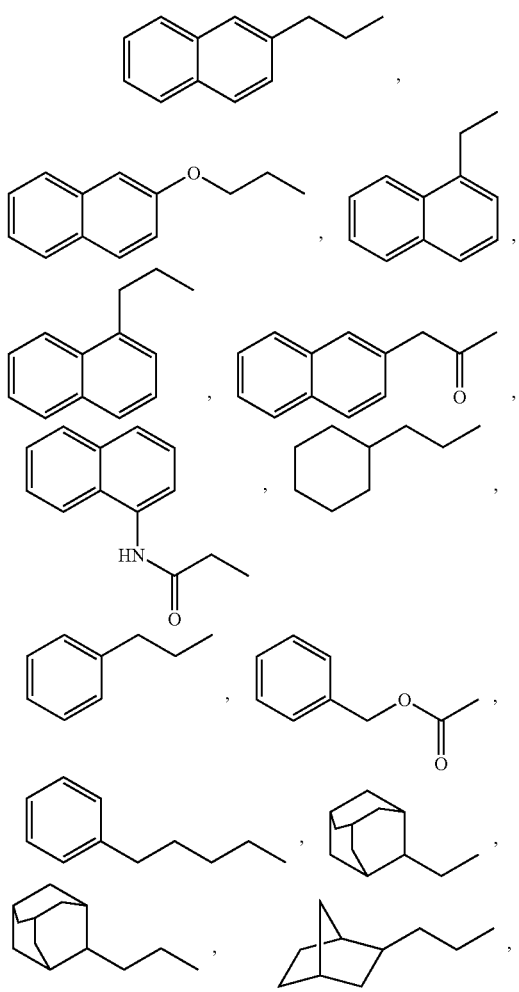

-continued

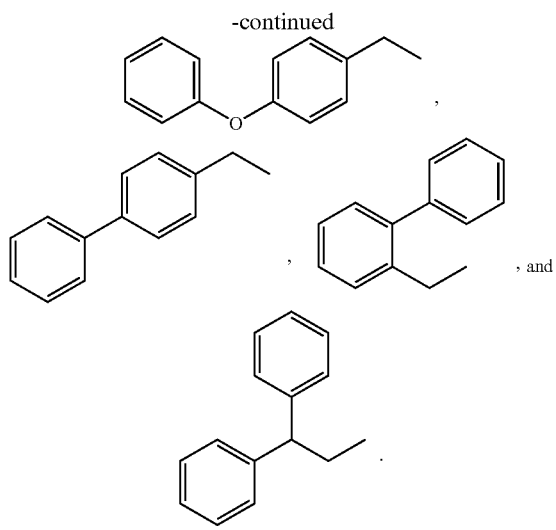

40. The compound of claim 35 wherein $R_2$ is selected from the group consisting of

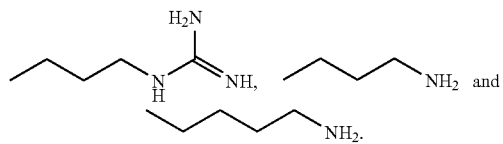

41. The compound of claim 35 wherein $R_6$ is an amine capping group selected from the group consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc and 8-Aoc.

42. A compound having the structure:

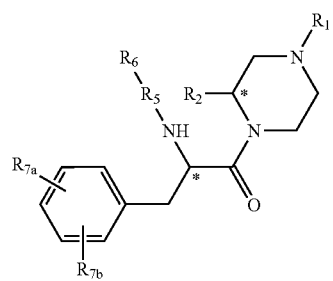

(IV)

or a stereoisomer or pharmaceutically acceptable salt thereof, wherein

R, is -L$_1$-J;

R$_2$ is (CH$_2$)$_y$—W;

R$_5$ is an amino acid residue;

R$_5$ is H or an amine capping group;

R$_{7a}$ and R$_{7b}$ are optional ring substituents, and when one or both are present, are the same or different and independently hydroxyl, halogen, alkyl, or aryl groups attached directly or through an ether linkage;

L$_1$ is a linker selected from the group consisting of —(CH$_2$)$_y$—, —O—(CH$_2$)$_y$—, —O—, —NH—(CH$_2$)$_y$—, —(C=O)(CH$_2$)$_y$—, —(C=O)—O—(CH$_2$)$_y$, and —CH$_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance each ring in the ring structure consists of 5 or 6 ring atoms;

W is selected from the group consisting of NH$_2$, NH(C=NH)NH$_2$, —NHCOCH$_3$, —CONHCH$_3$, —NH(C=NH)NHMe, —NH(C=NH)NHEt, —NH(C=NH)NHPr, —NH(C=NH)NHPr—I, —NH(C=NH)NH$_2$, —NH(C=O)OCH$_3$, —NH(C=O)CH$_3$, —NH(C=O)NH$_2$, —NH(C=O)NHCH$_3$,

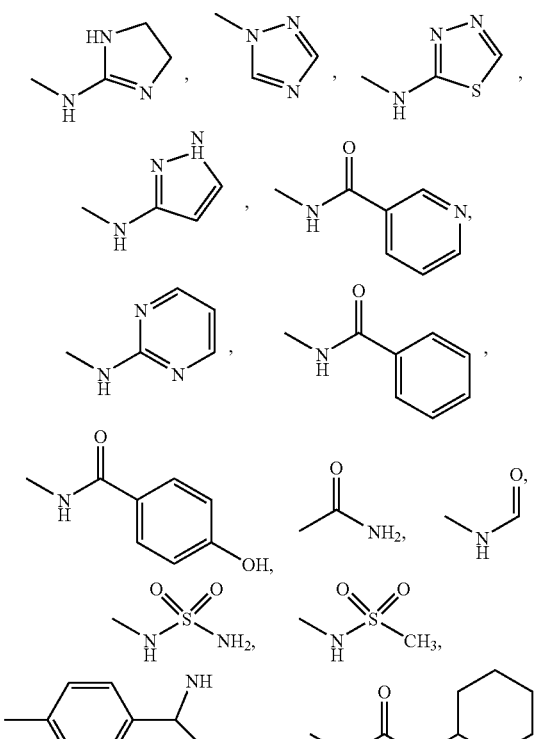

y is at each occurrence independently from 1 to 6;

wherein the carbon atoms marked with an asterisk can have any stereochemical configuration.

43. The compound of claim 42 wherein J is a substituted or unsubstituted ring structure selected from the group consisting of

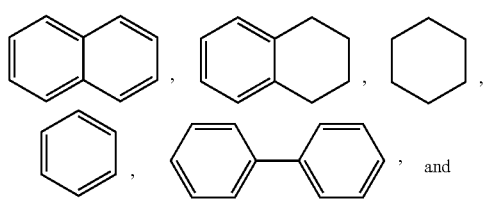

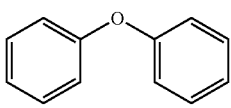

44. The compound of claim 42 wherein at least one ring of the group J is substituted with one or more halogen, alkyl or aryl groups.

45. The compound of claim 42 wherein $R_1$ is selected from the group consisting of

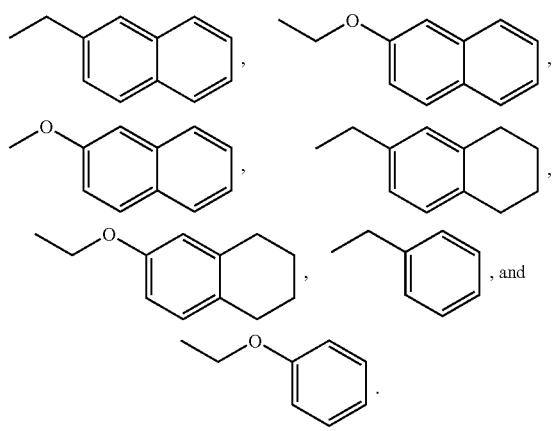

46. The compound of claim 42 wherein $R_1$ is selected from the group consisting of

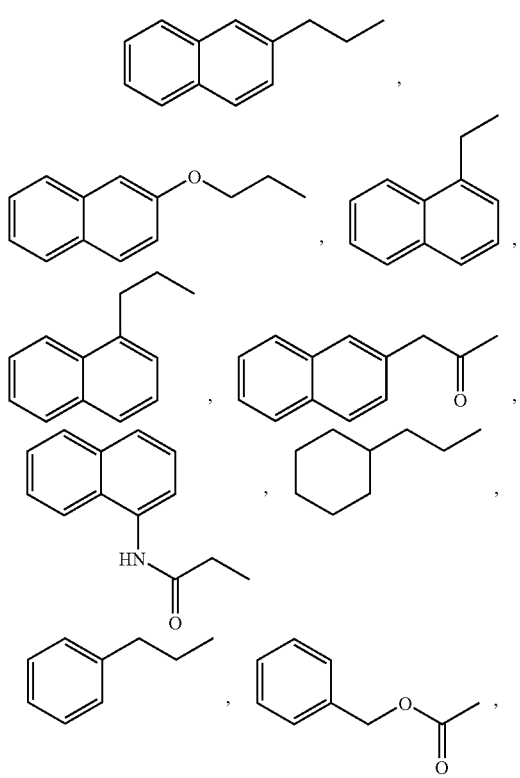

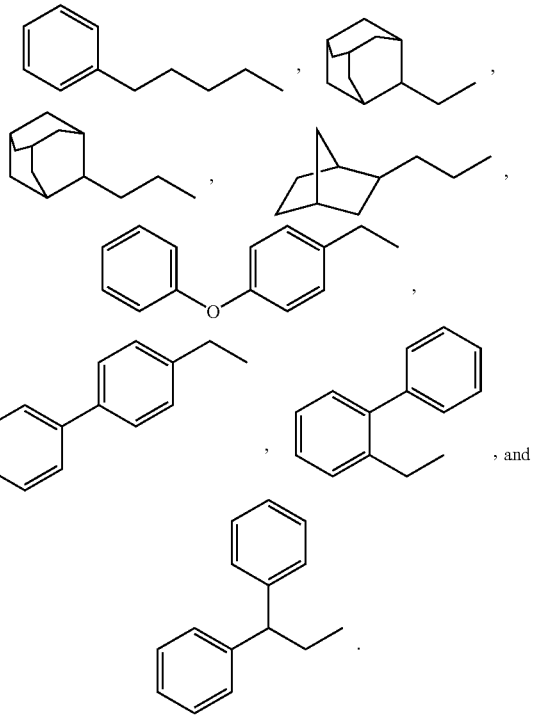

47. The compound of claim 42 wherein $R_2$ is selected from the group consisting of

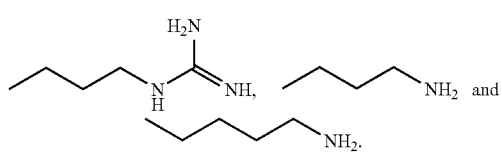

48. The compound of claim 42 wherein $R_6$ is an amine capping group selected from the group consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc and 8-Aoc.

49. The compound of claim 42 wherein $R_5$ is selected from the group of L-amino acids consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBZA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

50. A composition comprising a compound of any one of claims 1, 18, 35 and 42 in combination with a pharmaceutically acceptable carrier.

* * * * *